(12) United States Patent
Choi

(10) Patent No.: US 12,084,405 B2
(45) Date of Patent: Sep. 10, 2024

(54) PHENYLCARBAMATE CRYSTALLINE FORM AND METHOD FOR MANUFACTURING THE SAME

(71) Applicant: BIO-PHARM SOLUTIONS CO., LTD., Suwon-si (KR)

(72) Inventor: Yong Moon Choi, Irvine, CA (US)

(73) Assignee: Bio-Pharm Solutions Co., Ltd., Suwon-si (KR)

( * ) Notice: Subject to any disclaimer, the term of this patent is extended or adjusted under 35 U.S.C. 154(b) by 0 days.

(21) Appl. No.: 18/500,742

(22) Filed: Nov. 2, 2023

(65) Prior Publication Data

US 2024/0076265 A1    Mar. 7, 2024

Related U.S. Application Data

(60) Division of application No. 18/185,830, filed on Mar. 17, 2023, which is a continuation-in-part of application No. 17/837,929, filed on Jun. 10, 2022, now Pat. No. 11,795,139.

(30) Foreign Application Priority Data

Aug. 5, 2021 (KR) .................. 10-2021-0103371

(51) Int. Cl.
*C07C 271/12* (2006.01)
(52) U.S. Cl.
CPC ........ *C07C 271/12* (2013.01); *C07B 2200/13* (2013.01)

(58) Field of Classification Search
CPC .. C07C 271/12; C07C 271/16; C07B 2200/13
See application file for complete search history.

(56) References Cited

U.S. PATENT DOCUMENTS

| | | | |
|---|---|---|---|
| 8,859,817 B2 | 10/2014 | Choi | |
| 9,018,253 B2 | 4/2015 | Choi | |
| 9,034,848 B2 | 5/2015 | Choi | |
| 9,162,975 B2 | 10/2015 | Choi | |
| 9,457,003 B2 | 10/2016 | Choi | |
| 9,566,261 B2 | 2/2017 | Choi | |
| 9,624,164 B2 | 4/2017 | Choi | |
| 9,682,059 B2 | 6/2017 | Choi | |
| 9,872,847 B2 | 1/2018 | Choi | |
| 9,907,776 B2 | 3/2018 | Choi | |
| 9,956,197 B2 | 5/2018 | Choi | |
| 10,525,030 B2 | 1/2020 | Choi | |
| 11,795,139 B2 * | 10/2023 | Choi | C07C 269/08 |

(Continued)

FOREIGN PATENT DOCUMENTS

| | | |
|---|---|---|
| KR | 20090076958 A | 7/2009 |
| KR | 20130098401 A | 9/2013 |

(Continued)

OTHER PUBLICATIONS

Decision to Grant issued on Korean Patent Application No. KR 10-2021-0103371 on Apr. 21, 2022, 3 pages.

(Continued)

*Primary Examiner* — Deborah D Carr
(74) *Attorney, Agent, or Firm* — COOLEY LLP

(57) ABSTRACT

The present invention relates to crystalline forms of a phenyl carbamate derivative compound and compositions and uses thereof.

12 Claims, 48 Drawing Sheets

(56) References Cited

U.S. PATENT DOCUMENTS

| | | |
|---|---|---|
| 2008/0085930 A1 | 4/2008 | Peterson |
| 2013/0005801 A1 | 1/2013 | Choi |
| 2013/0165408 A1 | 6/2013 | Choi |
| 2013/0165409 A1 | 6/2013 | Choi |
| 2013/0165410 A1 | 6/2013 | Choi |
| 2014/0275243 A1 | 9/2014 | Choi |
| 2016/0015678 A1 | 1/2016 | Choi |
| 2016/0015679 A1 | 1/2016 | Choi |
| 2016/0015680 A1 | 1/2016 | Choi |
| 2016/0016896 A1 | 1/2016 | Choi |
| 2016/0023999 A1 | 1/2016 | Choi |
| 2016/0024000 A1 | 1/2016 | Choi |
| 2016/0264526 A1 | 9/2016 | Bio et al. |
| 2016/0296493 A1 | 10/2016 | Choi |
| 2023/0101131 A1 | 3/2023 | Choi |
| 2023/0286910 A1 | 9/2023 | Choi |

FOREIGN PATENT DOCUMENTS

| | | |
|---|---|---|
| KR | 20140108226 A | 9/2014 |
| KR | 20140113918 A | 9/2014 |
| KR | 20140113919 A | 9/2014 |
| KR | 20160018576 A | 2/2016 |
| KR | 20170058447 A | 5/2017 |
| WO | WO-2023014160 A1 | 2/2023 |

OTHER PUBLICATIONS

International Search Report/Written Opinion issued Dec. 2, 2022 for International Application No. PCT/KR2022/011648, with partial English Translation, 22 pgs.

Shah et al., "Analytical techniques for quantification of amorphous/crystalline phases in pharmaceutical solids". Journal of pharmaceutical sciences. Aug. 1, 2006; 95(8):1641-65.

\* cited by examiner

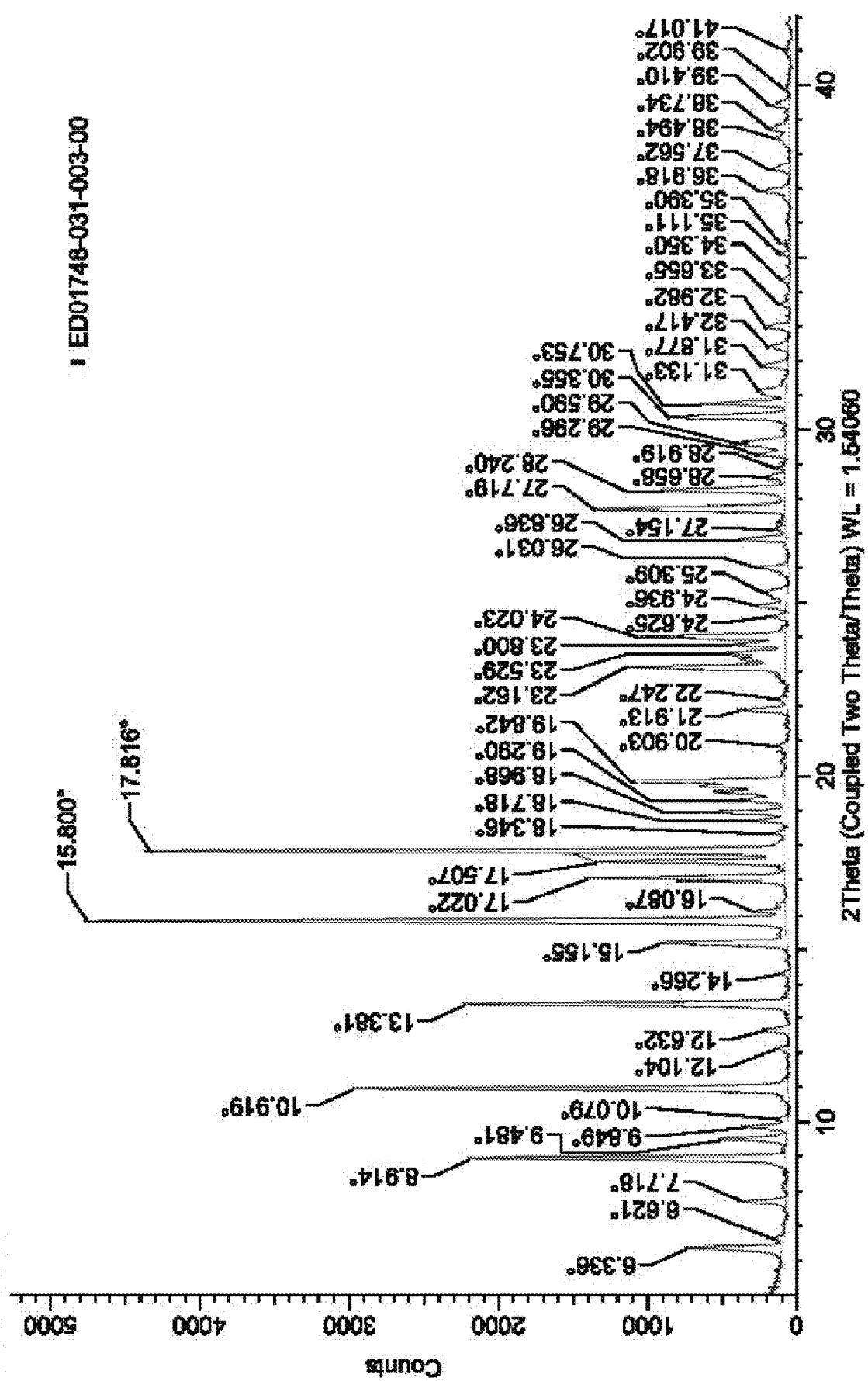

PHENYLCARBAMATE CRYSTALLINE FORM AND METHOD FOR MANUFACTURING THE SAME

CROSS-REFERENCE TO RELATED APPLICATIONS

This application is a Divisional of U.S. application Ser. No. 18/185,830, filed on Mar. 17, 2023, which is a Continuation-In-Part of U.S. application Ser. No. 17/837,929, filed on Jun. 10, 2022, now U.S. Pat. No. 11,795,139, which claims priority to Korean Patent Application No. 10-2021-0103371 filed on Aug. 5, 2021, the disclosures of which are incorporated herein by reference in their entirety.

BACKGROUND

Phenyl carbamate compounds are compounds known to have an effect on various neurological disorders including multiple sclerosis, Lou Gehrig's disease, epilepsy and central nervous system disorders, muscle diseases, stroke, psychiatric disorder and memory loss-related diseases. These compounds have excellent pharmacological effects on various diseases due to its high pharmacological activity, and have been developed and widely used as medicines due to low toxicity.

Among the phenyl carbamate compounds, (1-(2-chlorophenyl)-(S)-1-hydroxypropyl-(S)-2-carbamate (JBPOS0101) is a material that is verified to be particularly effective in treatment or prevention of multiple sclerosis (Korean Patent No. 10-2014-0113919 A) or Lou Gehrig's disease (10-2014-0113918 A), and research is being attempted to synthesize various crystalline forms of the material such that they have more improved stability and can be used in various formulations.

BRIEF SUMMARY OF THE INVENTION

In embodiments, the present provides crystalline forms of a phenyl carbamate derivative compound, 1-(2-chlorophenyl)-(S)-1-hydroxypropyl-(S)-2-carbamate (JBPOS0101).

In embodiments, the present disclosure provides a pharmaceutical composition comprising a crystalline form of 1-(2-chlorophenyl)-(S)-1-hydroxypropyl-(S)-2-carbamate (JBPOS0101).

BRIEF DESCRIPTION OF DRAWINGS

FIG. 24A shows an X-ray powder diffraction (XRPD) pattern of crystalline form Pattern 3 of Formula 1.

DETAILED DESCRIPTION

Definitions

Figure 1:
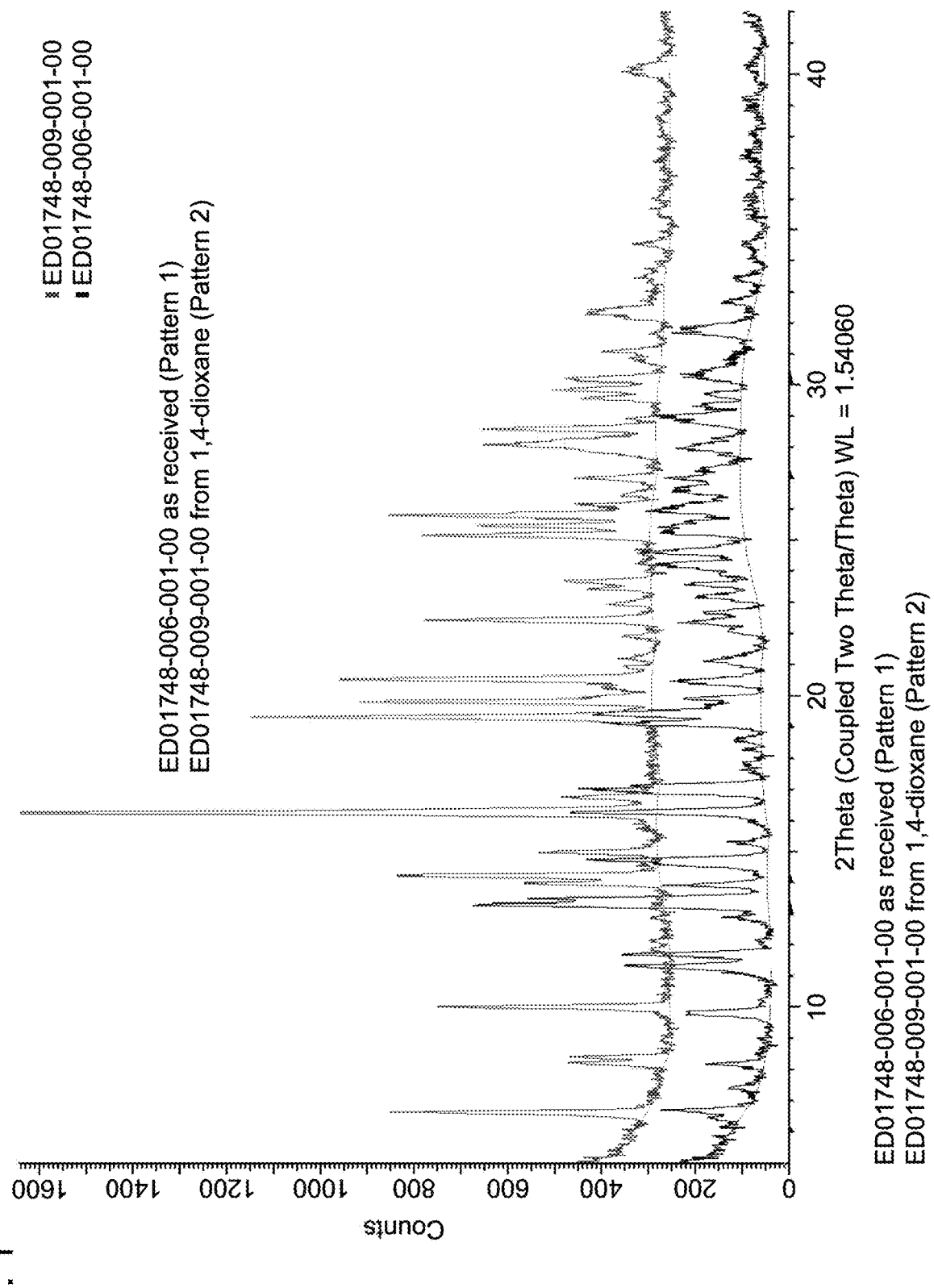
FIG. 1 shows the result of comparing XRPD patterns after 1,4-dioxane treatment (ED01748-009-001-00, Pattern 2) to form amorphous 1-(2-chlorophenyl)-(S)-1-hydroxypropyl-(S)-2-carbamate (JBPOS0101).

Throughout this disclosure, various patents, patent applications and publications (including non-patent publications) are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "effective amount" and "therapeutically effective amount" are used interchangeably in this disclosure and refer to an amount of a compound, or a salt, solvate or ester thereof, that, when administered to a patient, is capable of performing the intended result.

The term "substantially similar" as used herein means an analytical spectrum, such as XRPD pattern, DSC thermogram, etc., which resembles the reference spectrum to a great degree in both the peak locations and their intensity.

The term "treating" as used herein with regard to a patient, refers to improving at least one symptom of the patient's disorder. Treating can be improving, or at least partially ameliorating a disorder.

The term "therapeutic effect" as used herein refers to a desired or beneficial effect provided by the method and/or the composition. For example, the method for treating depression provides a therapeutic effect when the method reduces at least one symptom of depression in a patient.

Crystalline Forms of Formula 1

The present disclosure provides crystalline forms of the compound of Formula 1:

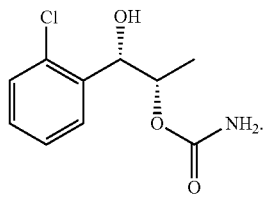

[Formula 1]

In embodiments, the present disclosure provides a mixture of one or more crystalline forms of the compound of Formula 1.

In embodiments, the present disclosure provides a substantially pure crystalline form of the compound of Formula 1 as described herein. Crystalline purity may be determined using methods known to those skilled in the art (including, among others, X-ray powder crystallography as described in Shah, B., et al., Analytical techniques for quantification of amorphous/crystalline phases in pharmaceutical solids, J. Pharm. Sci. 2006, 95(8), pages 1641-1665 which is hereby incorporated by reference in its entirety).

In embodiments, the present disclosure relates to an isolated crystalline form of Formula 1 or a pharmaceutically acceptable solvate salt thereof.

In one embodiment, the crystalline form of Formula 1 is crystalline Form Pattern 1, Pattern 2, Pattern 3, Pattern 4, Pattern 5, Pattern 6, Pattern 7, Pattern 8, Pattern 9, Pattern 10, or Pattern 11. In embodiments, the crystalline form of Formula 1 is crystalline Form Pattern 1. In embodiments, the crystalline form of Formula 1 is crystalline Form Pattern 3.

In embodiments, the crystalline form of Formula 1 or a pharmaceutically acceptable solvate thereof has a purity of at least about 75%, at least about 80%, at least about 85%, at least about 90%, at least about 95%, at least about 97%, at least about 98%, or at least about 99% as determined by HPLC analysis. In embodiments, the crystalline form of Formula 1, or a pharmaceutically acceptable solvate thereof has a purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, or about 90% as determined by HPLC analysis. In embodiments, the crystalline form of Formula 1, or a pharmaceutically acceptable solvate thereof has a purity of about 75% to about 99%. In embodiments, the crystalline form of Formula 1, or a pharmaceutically acceptable solvate thereof has a purity of about 80% to about 99%. In embodiments, the crystalline form of Formula 1, or a pharmaceutically acceptable solvate thereof has a purity of about 85% to about 99% as determined by HPLC analysis. In embodiments, the crystalline form of Formula 1, or a pharmaceutically acceptable solvate thereof has a purity of about 90% to about 99% as determined by HPLC analysis. In embodiments, the crystalline form of Formula 1, or a pharmaceutically acceptable solvate thereof has a purity of about 95% to about 99% as determined by HPLC analysis.

In embodiments, the crystalline form of Formula 1, or a pharmaceutically acceptable solvate thereof has a polymorphic purity of at least about 75%, at least about 80%, at least about 85%, at least about 90%, at least about 95%, at least about 97%, at least about 98%, or at least about 99% with respect to one specific crystalline form of Formula 1 or a pharmaceutically acceptable solvate thereof. In embodiments, the crystalline form of Formula 1, or a pharmaceutically acceptable solvate thereof has a polymorphic purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, or about 90% with respect to one specific crystalline form of Formula 1 or a pharmaceutically acceptable solvate thereof. In embodiments, the crystalline form of Formula 1, or a pharmaceutically acceptable solvate thereof has a polymorphic purity of about 75% to about 99% with respect to one specific crystalline form of Formula 1 or a pharmaceutically acceptable solvate thereof. In embodiments, the crystalline form of Formula 1, or a pharmaceutically acceptable solvate thereof has a polymorphic purity of about 80% to about 99% with respect to one specific crystalline form of Formula 1 or a pharmaceutically acceptable solvate thereof. In embodiments, the crystalline form of Formula 1, or a pharmaceutically acceptable solvate thereof has polymorphic a purity of about 85% to about 99% with respect to one specific crystalline form of Formula 1 or a pharmaceutically acceptable solvate thereof. In embodiments, the crystalline form of Formula 1, or a pharmaceutically acceptable solvate thereof has a polymorphic purity of about 90% to about 99% with respect to one specific crystalline form of Formula 1 or a pharmaceutically acceptable solvate thereof. In embodiments, the crystalline form of Formula 1, or a pharmaceutically acceptable solvate thereof has a polymorphic purity of about 95% to about 99% with respect to one specific crystalline form of Formula 1 or a pharmaceutically acceptable solvate thereof. Polymorphic purity may be determined using methods known to those skilled in the art (including, among others, X-ray powder crystallography as described in Shah, B., et al, Analytical techniques for quantification of amorphous/crystalline phases in pharmaceutical solids, J. Pharm. Sci. 2006, 95(8), pages 1641-1665 which is hereby incorporated by reference in its entirety).

Crystalline Pattern 1 of Formula 1

In embodiments, the present disclosure provides a crystalline Pattern 1 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 1. In embodiments, the crystalline form of Formula 1 comprises greater than about 99%, 98%, 97%, 96%, 95%, 94%, 93%, 92%, 91%, or 90% of Pattern 1. In some embodiments, the crystalline form of Formula 1 comprises greater than about 90%, 85%, 80%, 75%, 70%, 65%, 60%, 55%, 50%, 45%, or 40% of Pattern 1.

In embodiments, the crystalline form of the compound of Formula 1 exhibits an XRPD pattern comprising peaks at 13.3, 13.4, and 16.2 °2θ with the margin of error of about ±0.2; about ±0.1; or about ±0.05. In embodiments, the XRPD of the crystalline form of the compound of Formula 1 further comprises peaks at 11.7 and 14.7±0.2 °2θ with the margin of error of about ±0.2; about ±0.1; or about ±0.05. In embodiments, the XRPD of the crystalline form of the compound of Formula 1 further comprises peaks at 11.3 and 17.0 °2θ with the margin of error of about ±0.2; about ±0.1; or about ±0.05. In embodiments, the XRPD of the crystalline form of the compound of Formula 1 further comprises at least one peak selected from 6.7, 8.2, 9.8, 13.9, 19.1, 19.4, 24.6, or 27.0 °2θ with the margin of error of about ±0.2; about ±0.1; or about ±0.05. In embodiments, the XRPD of the crystalline form of the compound of Formula 1 further comprises at least two peaks selected from 6.7, 8.2, 9.8, 13.9, 19.1, 19.4, 24.6, or 27.0 °2θ with the margin of error of about ±0.2; about ±0.1; or about ±0.05. In embodiments, the XRPD of the crystalline form of the compound of Formula 1 further comprises at least three peaks selected from 6.7, 8.2, 9.8, 13.9, 19.1, 19.4, 24.6, or 27.0 °2θ with the margin of error of about ±0.2; about ±0.1; or about ±0.05. In embodiments, the XRPD of the crystalline form of the compound of Formula 1 further comprises at least four peaks selected from 6.7, 8.2, 9.8, 13.9, 19.1, 19.4, 24.6, or 27.0 °2θ with the margin of error of about ±0.2; about ±0.1; or about ±0.05. In embodiments, the XRPD of the crystalline form of the compound of Formula 1 further comprises at least five peaks selected from 6.7, 8.2, 9.8, 13.9, 19.1, 19.4, 24.6, or 27.0 °2θ with the margin of error of about ±0.2; about ±0.1; or about ±0.05. In embodiments, the XRPD of the crystalline form of the compound of Formula 1 further comprises at least six peaks selected from 6.7, 8.2, 9.8, 13.9, 19.1, 19.4, 24.6, or 27.0 °2θ with the margin of error of about ±0.2; about ±0.1; or about ±0.05. In embodiments, the XRPD of the crystalline form of the compound of Formula 1 further comprises at least seven peaks selected from 6.7, 8.2, 9.8, 13.9, 19.1, 19.4, 24.6, or 27.0 °2θ with the margin of error of about ±0.2; about ±0.1; or about ±0.05. In embodiments, the XRPD of the crystalline form of the compound of Formula 1 further comprises peaks at 6.7, 8.2, 9.8, 13.9, 19.1, 19.4, 24.6, and 27.0 °2θ with the margin of error of about ±0.2; about ±0.1; or about ±0.05.

In embodiments, the crystalline form of the compound of Formula 1 exhibits an XRPD pattern comprising peaks at 13.3±0.2, 13.4±0.2, and 16.2±0.2 °2θ. In embodiments, the crystalline form of the compound of Formula 1 exhibits an XRPD pattern comprising peaks at 11.3±0.2 and 17.0±0.2 °2θ. In embodiments, the crystalline form of the compound of Formula 1 exhibits an XRPD pattern comprising at least one peak selected from 6.7±0.2, 8.2±0.2, 9.8±0.2, 13.9±0.2, 19.1±0.2, 19.4±0.2, 24.6±0.2, or 27.0±0.2 °2θ. In embodiments, the crystalline form of the compound of Formula 1 exhibits an XRPD pattern comprising at least two peaks selected from 6.7±0.2, 8.2±0.2, 9.8±0.2, 13.9±0.2, 19.1±0.2, 19.4±0.2, 24.6±0.2, or 27.0±0.2 °2θ. In embodiments, the crystalline form of the compound of Formula 1 exhibits an XRPD pattern comprising at least three peaks selected from 6.7±0.2, 8.2±0.2, 9.8±0.2, 13.9±0.2, 19.1±0.2, 19.4±0.2, 24.6±0.2, or 27.0±0.2 °2θ. In embodiments, the crystalline form of the compound of Formula 1 exhibits an XRPD pattern comprising at least four peaks selected from 6.7±0.2, 8.2±0.2, 9.8±0.2, 13.9±0.2, 19.1±0.2, 19.4±0.2, 24.6±0.2, or 27.0±0.2 °2θ. In embodiments, the crystalline form of the compound of Formula 1 exhibits an XRPD pattern comprising at least five peaks selected from 6.7±0.2, 8.2±0.2, 9.8±0.2, 13.9±0.2, 19.1±0.2, 19.4±0.2, 24.6±0.2, or 27.0±0.2 °2θ. In embodiments, the crystalline form of the compound of Formula 1 exhibits an XRPD pattern comprising at least six peaks selected from 6.7±0.2, 8.2±0.2, 9.8±0.2, 13.9±0.2, 19.1±0.2, 19.4±0.2, 24.6±0.2, or 27.0±0.2 °2θ. In embodiments, the crystalline form of the compound of Formula 1 exhibits an XRPD pattern comprising at least seven peaks selected from 6.7±0.2, 8.2±0.2, 9.8±0.2, 13.9±0.2, 19.1±0.2, 19.4±0.2, 24.6±0.2, or 27.0±0.2 °2θ. In embodiments, the crystalline form of the compound of Formula 1 exhibits an XRPD pattern comprising peaks at 6.7±0.2, 8.2±0.2, 9.8±0.2, 13.9±0.2, 19.1±0.2, 19.4±0.2, 24.6±0.2, and 27.0±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 2.

In embodiments, the crystalline form of the compound of Formula 1 exhibits an XRPD comprising peaks shown in Table 2.

In embodiments, the crystalline form of the compound of Formula 1 exhibits an XRPD pattern comprising one or more peaks from Table 2 having intensity of at least 5%. In embodiments, the crystalline form of the compound of Formula 1 exhibits an XRPD pattern comprising one or more peaks from Table 2 having intensity of at least 10%. In embodiments, the crystalline form of the compound of Formula 1 exhibits an XRPD pattern comprising one or more peaks from Table 2 having intensity of at least 20%. In embodiments, the crystalline form of the compound of Formula 1 exhibits an XRPD pattern comprising one or more peaks from Table 2 having intensity of at least 25%. In embodiments, the crystalline form of the compound of Formula 1 exhibits an XRPD pattern comprising one or more peaks from Table 2 having intensity of at least 30%. In embodiments, the crystalline form of the compound of Formula 1 exhibits an XRPD pattern comprising one or more peaks from Table 2 having intensity of at least 35%. In embodiments, the crystalline form of the compound of Formula 1 exhibits an XRPD pattern comprising one or more peaks from Table 2 having intensity of at least 40%. In embodiments, the crystalline form of the compound of Formula 1 exhibits an XRPD pattern comprising one or more peaks from Table 2 having intensity of at least 45%. In embodiments, the crystalline form of the compound of Formula 1 exhibits an XRPD pattern comprising one or more peaks from Table 2 having intensity of at least 50%. In embodiments, the crystalline form of the compound of Formula 1 exhibits an XRPD pattern comprising one or more peaks from Table 2 having intensity of at least 60%. In embodiments, the crystalline form of the compound of Formula 1 exhibits an XRPD pattern comprising one or more peaks from Table 2 having intensity of at least 70%. In embodiments, the crystalline form of the compound of Formula 1 exhibits an XRPD pattern comprising one or more peaks from Table 2 having intensity of at least 80%. In embodiments, the crystalline form of the compound of Formula 1 exhibits an XRPD pattern comprising one or more peaks from Table 2 having intensity of at least 90%.

Figure 10:
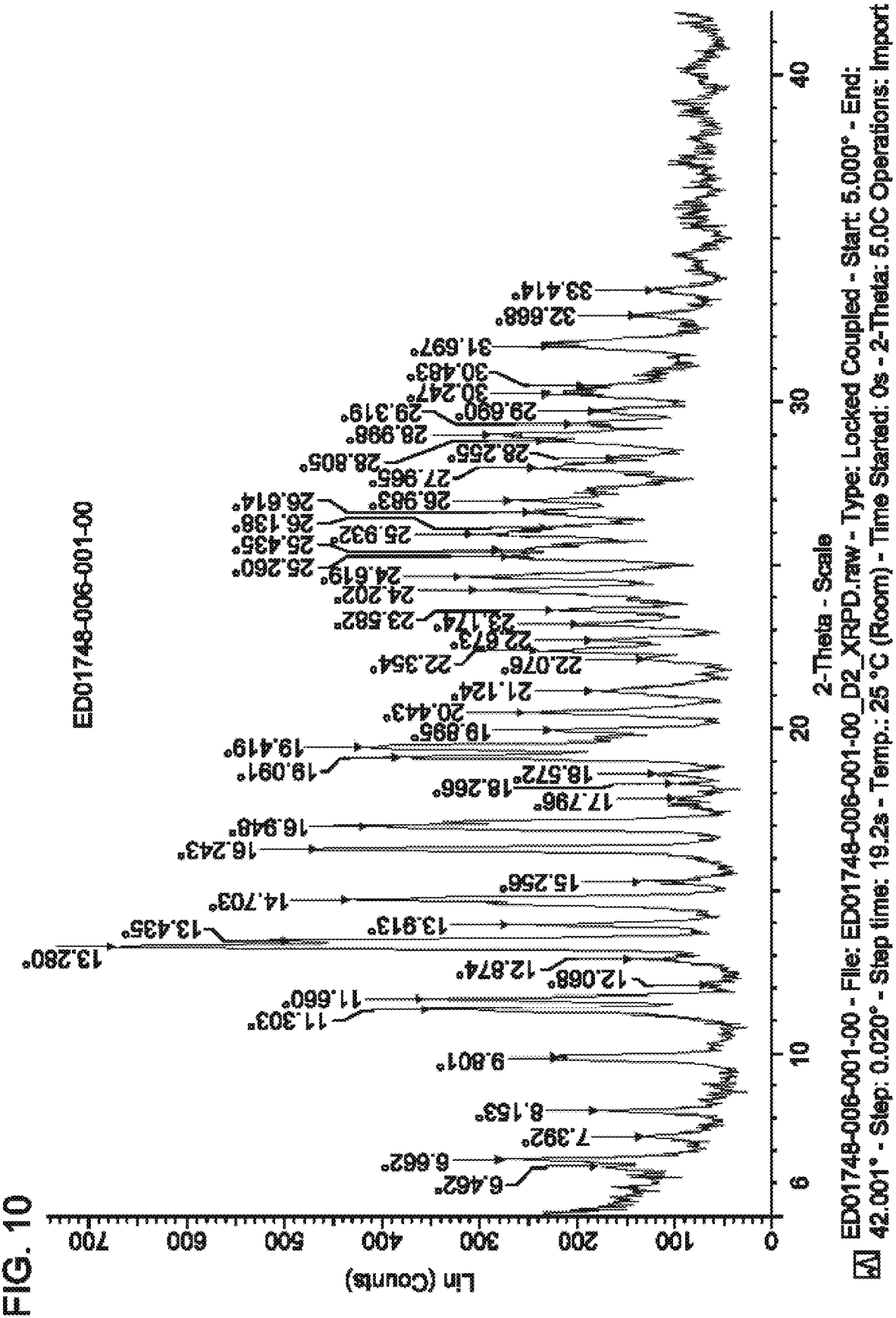
FIG. 10 shows the XRPD diffractogram result of the crystalline form of 1-(2-chlorophenyl)-(S)-1-hydroxypropyl-(S)-2-carbamate (7BPOS0101) Pattern 1.

In one specific embodiment, the crystalline form of Formula 1 exhibits an XRPD pattern that is substantially similar to FIG. 10.

In embodiments, the crystalline form of Formula 1 exhibits an about 5% (wt %) loss between about 39° C. to about 237° C. as determined by thermogravimetric analysis (TGA).

In embodiments, the crystalline form of Formula 1 exhibits a DSC thermogram comprising an endotherm peak at about 81° C. (onset) with the error of margin of about ±2.5; about ±2.0; about ±1.5; about ±1.0; about ±0.5; or less.

In embodiments, the crystalline form of Formula 1 exhibits a DSC thermogram comprising an endotherm peak at about 89° C. (onset) with the error of margin of about ±2.5; about ±2.0; about ±1.5; about ±1.0; about ±0.5; or less.

In embodiments, the crystalline form of Formula 1 exhibits a DSC thermogram comprising an endotherm peak at about 229° C. (onset) with the error of margin of about ±2.5; about ±2.0; about ±1.5; about ±1.0; about ±0.5; or less.

Figure 14:
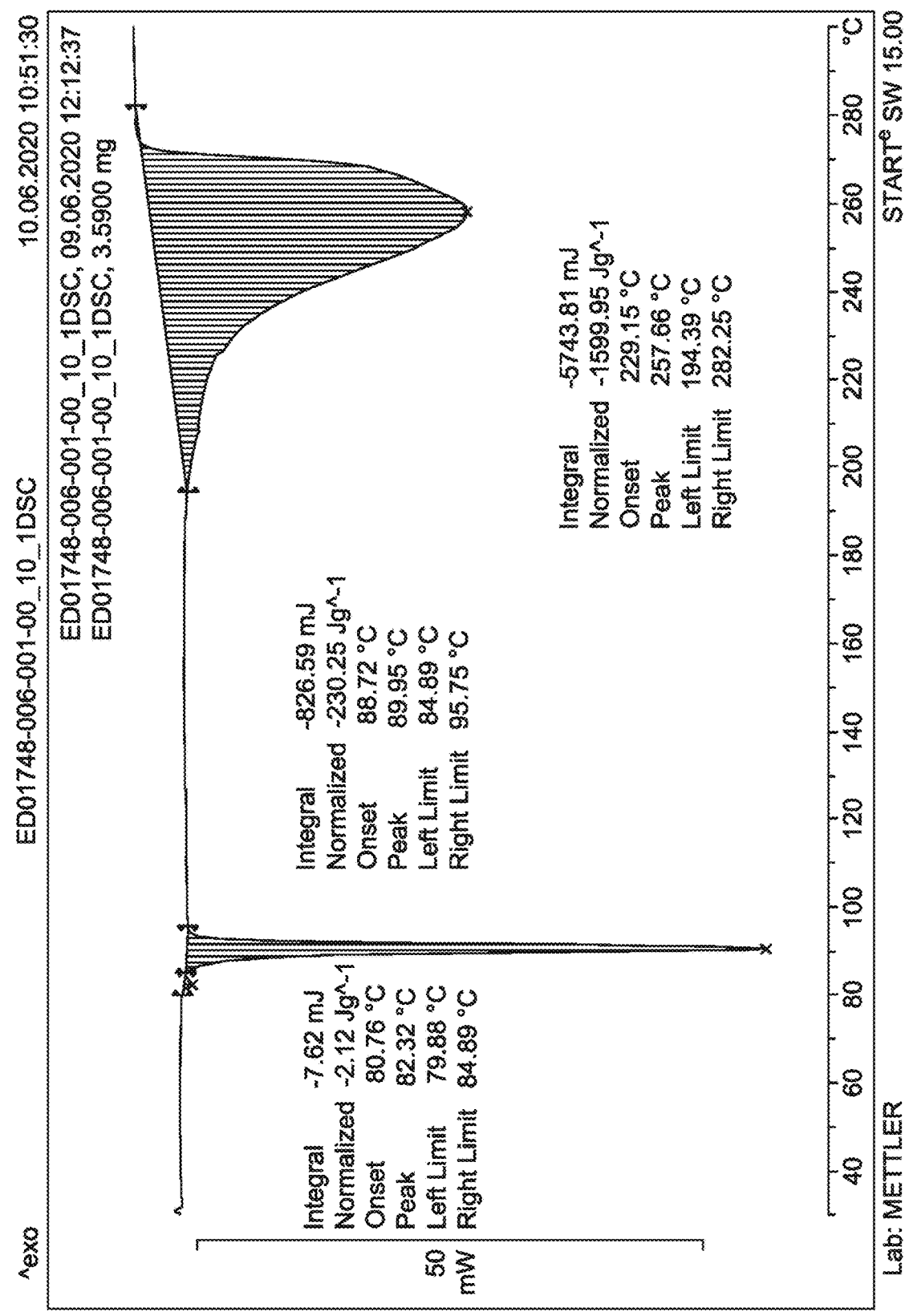
FIG. 14 is the DSC thermogram of the crystalline form of 1-(2-chlorophenyl)-(5)-1-hydroxypropyl-(S)-2-carbamate (JBPOS0101) Pattern 1.

In embodiments, the crystalline form of Formula 1 exhibits a DSC thermogram that is substantially similar to the DSC thermogram of FIG. 14.

Figure 15:
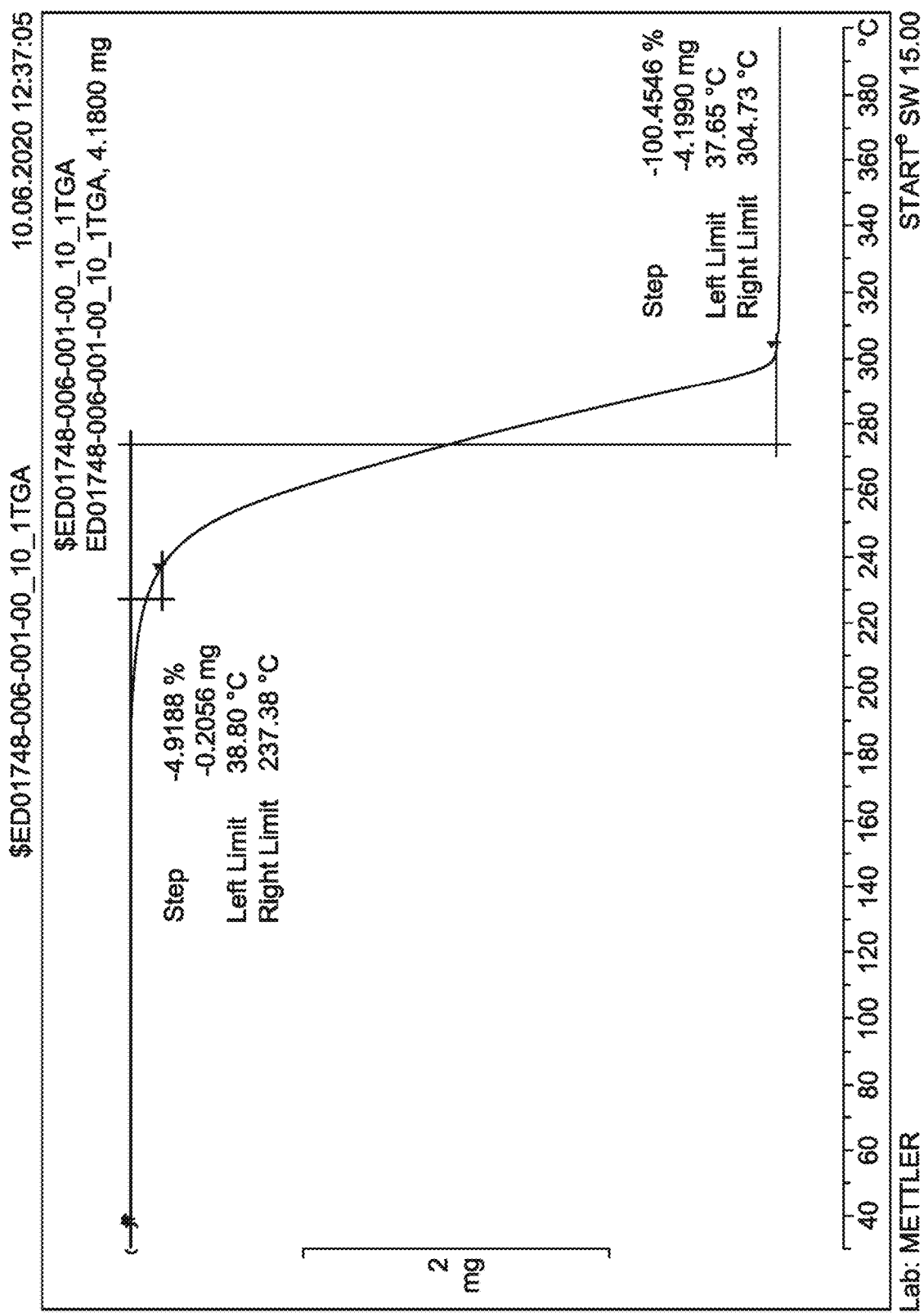
FIG. 15 is the TGA thermogram of the crystalline form of 1-(2-chlorophenyl)-(5)-1-hydroxypropyl-(S)-2-carbamate (JBPOS0101) Pattern 1 at a temperature of 200° C. or more.

In embodiments, the crystalline form of Formula 1 exhibits a TGA thermogram that is substantially similar to the TGA thermogram of FIG. 15.

In embodiments, Pattern 1 crystalline form has a melting point of 89° C., and has no considerable mass loss in TGA until decomposed at about 200° C. or more. During a GVS experiment, it was confirmed that there is almost no mass increase within a 0-90% RH range (0.14%), and after the GVS experiment, it was confirmed by XRPD that even when exposed to a high humidity at 40° C./75% RH or RT/97% RH, the Pattern 1 crystalline form has no morphological change.

In embodiments, the pattern I crystalline form of (1-(2-chlorophenyl)-(S)-1-hydroxypropyl-(S)-2-carbamate) has peaks at diffraction angles (2θ) of 6.662°, 8.153°, 9.801°, 11.303°, 11.660°, 13.280°, 13.435°, 14.703°, 16.243°, 16.948°, 19.091°, 19.419°, 20.443°, 21.124°, 24.202°, 24.619°, 28.998° and 31.697° in X-ray powder diffraction (XRPD) patterns. Additional peaks may also be shown at one or more diffraction angles (2θ) of 7.392°, 12.068°, 12.874°, 13.913°, 15.256°, 17.796°, 18.266°, 18.572°, 19.895°, 22.076°, 22.354°, 22.673°, 23.174°, 23.582°, 25.260°, 25.435°, 25.932°, 26.138°, 26.614°, 26.983°, 27.965°, 28.256°, 28.805°, 29.319°, 29.690°, 30.247°, 30.483°, 32.668° and 33.414°.

In some embodiments, the crystalline form of Formula 1 is at least about 90% Pattern 1 by weight. In some embodiments, the crystalline form of Formula 1 is at least about 95% Pattern 1 by weight. In some embodiments, the crystalline form of Formula 1 is at least about 95% Pattern 1 by weight. In some embodiments, the crystalline form of Formula 1 is at least about 99% Pattern 1 by weight. In some embodiments, the crystalline form of Formula 1 is at least about 90%, about 91%, about 92%, about 93%, about 94%, about 95%, about 96%, about 97%, about 98%, or about 99% Pattern 1 by weight.

In some embodiments, the crystalline form of Formula 1 is about 70% to about 100%, about 85.0% to 100%, or about 95.0% to 100% Pattern 1 by weight. In some embodiments, the crystalline form of Formula 1 is about 98.0% to 100% Pattern 1 by weight.

Crystalline Pattern 2 of Formula 1

In embodiments, the present disclosure provides a crystalline Pattern 2 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 2. In embodiments, the crystalline form of Formula 1 comprises greater than about 99%, 98%, 97%, 96%, 95%, 94%, 93%, 92%, 91%, or 90% of Pattern 2. In some embodiments, the crystalline form of Formula 1 comprises greater than about 90%, 85%, 80%, 75%, 70%, 65%, 60%, 55%, 50%, 45%, or 40% of Pattern 2.

In embodiments, the crystalline form of Formula 1 exhibits an XRPD pattern comprising peaks at 16.3, 19.3, and 20.6 °2θ with the margin of error of about ±0.2; about ±0.1; or about ±0.05. In embodiments, the XRPD of the crystalline form of Formula 1 further comprises peaks at 19.8 or 25.8 °2θ with the margin of error of about ±0.2; about ±0.1; or about ±0.05. In embodiments, the XRPD of the crystalline form of Formula 1 further comprises peaks at 14.3 and 25.5 °2θ with the margin of error of about ±0.2; about ±0.1; or about ±0.05. In embodiments, the XRPD of the crystalline form of Formula 1 further comprises at least one peak selected from 6.7, 10.0, 14.0, 22.4, 25.2, 28.1, or 28.6 °2θ with the margin of error of about ±0.2; about ±0.1; or about ±0.05. In embodiments, the XRPD of the crystalline form of Formula 1 further comprises at least two peaks selected from 6.7, 10.0, 14.0, 22.4, 25.2, 28.1, or 28.6 °2θ with the margin of error of about ±0.2; about ±0.1; or about ±0.05. In embodiments, the XRPD of the crystalline form of Formula 1 further comprises at least three peaks selected from 6.7, 10.0, 14.0, 22.4, 25.2, 28.1, or 28.6 °2θ with the margin of error of about ±0.2; about ±0.1; or about ±0.05. In embodiments, the XRPD of the crystalline form of Formula 1 further comprises at least four peaks selected from 6.7, 10.0, 14.0, 22.4, 25.2, 28.1, or 28.6 °2θ with the margin of error of about ±0.2; about ±0.1; or about ±0.05. In embodiments, the XRPD of the crystalline form of Formula 1 further comprises at least five peaks selected from 6.7, 10.0, 14.0, 22.4, 25.2, 28.1, or 28.6 °2θ with the margin of error of about ±0.2; about ±0.1; or about ±0.05. In embodiments, the XRPD of the crystalline form of Formula 1 further comprises at least one, at least two, at least six peaks selected from 6.7, 10.0, 14.0, 22.4, 25.2, 28.1, or 28.6 °2θ with the margin of error of about ±0.2; about ±0.1; or about ±0.05. In embodiments, the XRPD of the crystalline form of Formula 1 further comprises peaks at 6.7, 10.0, 14.0, 22.4, 25.2, 28.1, and 28.6 °2θ with the margin of error of about ±0.2; about ±0.1; or about ±0.05. In embodiments, the XRPD of the crystalline form of Formula 1 further comprises at least 1, at least 2, at least 3, at least 4, at least 5, at least 6, at least 7, at least 8, at least 9, at least 10, at least 11, at least 12, at least 13, at least 14, at least 15, at least 16, or at least 17 peaks selected from 8.2, 8.4, 12.9, 13.2, 14.6, 16.8, 22.0, 23.0, 23.7, 26.2, 27.0, 31.7, 34.6, 35.6, 36.0, 37.3, 38.6, or 40.1 °2θ with the margin of error of about ±0.2; about ±0.1; or about ±0.05. In embodiments, the XRPD of the crystalline form of Formula 1 further comprises peaks at 8.2, 8.4, 12.9, 13.2, 14.6, 16.8, 22.0, 23.0, 23.7, 26.2, 27.0, 31.7, 34.6, 35.6, 36.0, 37.3, 38.6, and 40.1 °2θ with the margin of error of about ±0.2; about ±0.1; or about ±0.05.

In embodiments, the crystalline form of the compound of Formula 1 exhibits an XRPD pattern comprising peaks at 16.3±0.2, 19.3±0.2, and 20.6±0.2 °2θ. In embodiments, the crystalline form of the compound of Formula 1 exhibits an XRPD pattern comprising peaks at 19.8±0.2 or 25.8±0.2 °2θ. In embodiments, the crystalline form of the compound of Formula 1 exhibits an XRPD pattern comprising peaks at 14.3±0.2 and 25.5±0.2 °2θ. In embodiments, the crystalline form of the compound of Formula 1 exhibits an XRPD pattern comprising at least one peak selected from 6.7±0.2, 10.0±0.2, 14.0±0.2, 22.4±0.2, 25.2±0.2, 28.1±0.2, or 28.6±0.2 °2θ. In embodiments, the crystalline form of the compound of Formula 1 exhibits an XRPD pattern comprising at least two peaks selected from 6.7±0.2, 10.0±0.2, 14.0±0.2, 22.4±0.2, 25.2±0.2, 28.1±0.2, or 28.6±0.2 °2θ. In embodiments, the crystalline form of the compound of Formula 1 exhibits an XRPD pattern comprising at least three peaks selected from 6.7±0.2, 10.0±0.2, 14.0±0.2, 22.4±0.2, 25.2±0.2, 28.1±0.2, or 28.6±0.2 °2θ. In embodiments, the crystalline form of the compound of Formula 1 exhibits an XRPD pattern comprising at least four peaks selected from 6.7±0.2, 10.0±0.2, 14.0±0.2, 22.4±0.2, 25.2±0.2, 28.1±0.2, or 28.6±0.2 °2θ. In embodiments, the crystalline form of the compound of Formula 1 exhibits an XRPD pattern comprising at least five peaks selected from 6.7±0.2, 10.0±0.2, 14.0±0.2, 22.4±0.2, 25.2±0.2, 28.1±0.2, or 28.6±0.2 °2θ. In embodiments, the crystalline form of the compound of Formula 1 exhibits an XRPD pattern comprising at least six peaks selected from 6.7±0.2, 10.0±0.2, 14.0±0.2, 22.4±0.2, 25.2±0.2, 28.1±0.2, or 28.6±0.2 °2θ. In embodiments, the crystalline form of the compound of Formula 1 exhibits an XRPD pattern comprising peaks at 6.7±0.2, 10.0±0.2, 14.0±0.2, 22.4±0.2, 25.2±0.2, 28.1±0.2, and 28.6±0.2 °2θ. In embodiments, the XRPD of the crystalline form of Formula 1 further comprises at least 1, at least 2, at least 3, at least 4, at least 5, at least 6, at least 7, at least 8, at least 9, at least 10, at least 11, at least 12, at least 13, at least 14, at least 15, at least 16, or at least 17 peaks selected from 8.2±0.2, 8.4±0.2, 12.9±0.2, 13.2±0.2, 14.6±0.2, 16.8±0.2, 22.0±0.2, 23.0±0.2, 23.7±0.2, 26.2±0.2, 27.0±0.2, 31.7±0.2, 34.6±0.2, 35.6±0.2, 36.0±0.2, 37.3±0.2, 38.6±0.2, or 40.1±0.2 °2θ. In embodiments, the XRPD of the crystalline form of Formula 1 further comprises peaks at 8.2±0.2, 8.4±0.2, 12.9±0.2, 13.2±0.2, 14.6±0.2, 16.8±0.2, 22.0±0.2, 23.0±0.2, 23.7±0.2, 26.2±0.2, 27.0±0.2, 31.7±0.2, 34.6±0.2, 35.6±0.2, 36.0±0.2, 37.3±0.2, 38.6±0.2, and 40.1±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 7.

In embodiments, the crystalline form of the compound of Formula 1 exhibits an XRPD comprising peaks shown in Table 7.

In embodiments, the crystalline form of the compound of Formula 1 exhibits an XRPD pattern comprising one or more peaks from Table 7 having intensity of at least 5%. In embodiments, the crystalline form of the compound of Formula 1 exhibits an XRPD pattern comprising one or more peaks from Table 7 having intensity of at least 10%. In embodiments, the crystalline form of the compound of Formula 1 exhibits an XRPD pattern comprising one or more peaks from Table 7 having intensity of at least 20%. In embodiments, the crystalline form of the compound of Formula 1 exhibits an XRPD pattern comprising one or more peaks from Table 7 having intensity of at least 25%. In embodiments, the crystalline form of the compound of Formula 1 exhibits an XRPD pattern comprising one or more peaks from Table 7 having intensity of at least 30%. In embodiments, the crystalline form of the compound of Formula 1 exhibits an XRPD pattern comprising one or more peaks from Table 7 having intensity of at least 35%. In embodiments, the crystalline form of the compound of Formula 1 exhibits an XRPD pattern comprising one or more peaks from Table 7 having intensity of at least 40%. In embodiments, the crystalline form of the compound of Formula 1 exhibits an XRPD pattern comprising one or more peaks from Table 7 having intensity of at least 45%. In embodiments, the crystalline form of the compound of Formula 1 exhibits an XRPD pattern comprising one or more peaks from Table 7 having intensity of at least 50%. In embodiments, the crystalline form of the compound of Formula 1 exhibits an XRPD pattern comprising one or more peaks from Table 7 having intensity of at least 60%. In embodiments, the crystalline form of the compound of Formula 1 exhibits an XRPD pattern comprising one or more peaks from Table 7 having intensity of at least 70%. In embodiments, the crystalline form of the compound of Formula 1 exhibits an XRPD pattern comprising one or more peaks from Table 7 having intensity of at least 80%. In embodiments, the crystalline form of the compound of Formula 1 exhibits an XRPD pattern comprising one or more peaks from Table 7 having intensity of at least 90%.

Figure 23A:
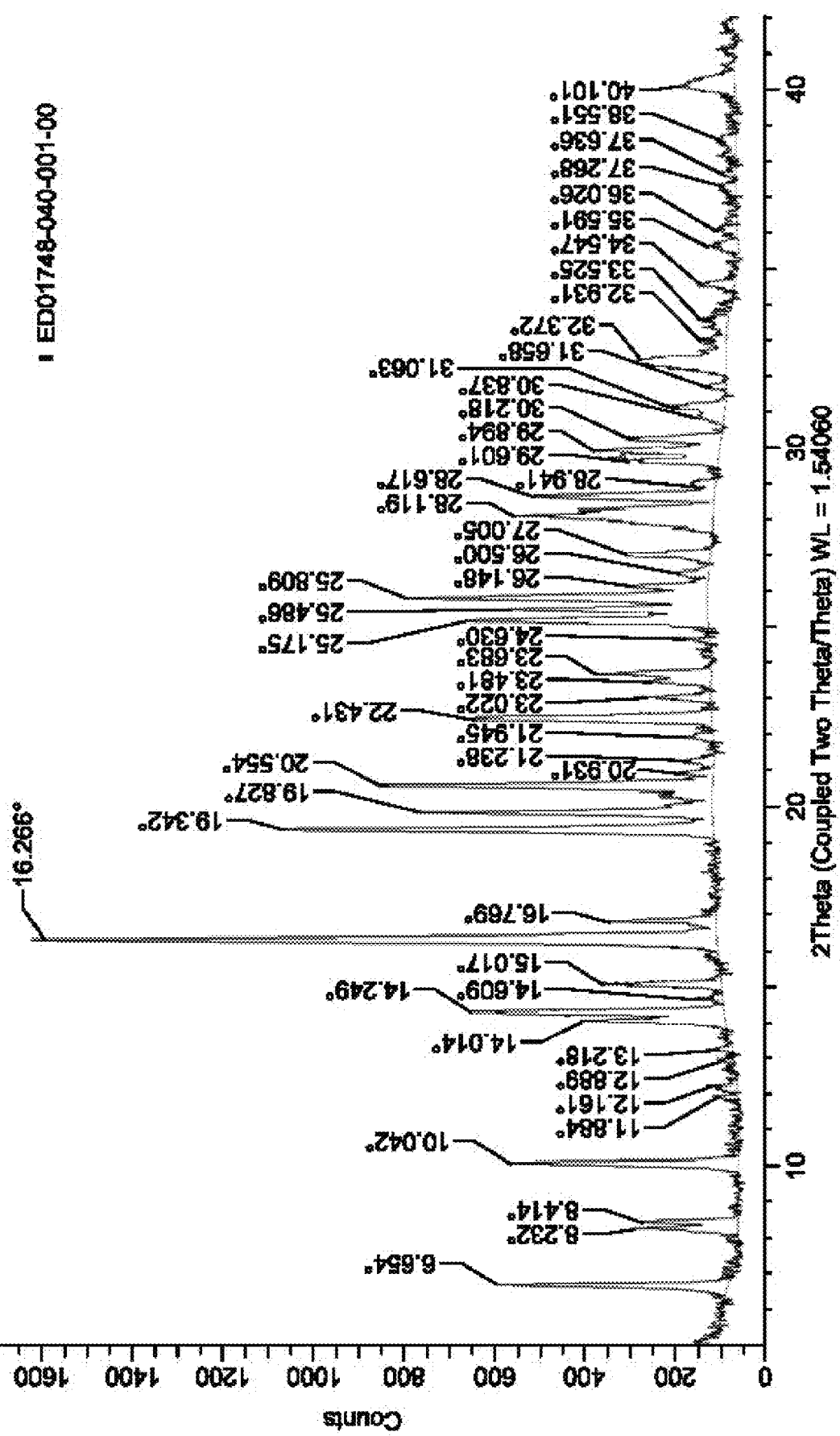
FIG. 23A shows an X-ray powder diffraction (XRPD) pattern of crystalline form Pattern 2 of Formula 1.

In one specific embodiment, the crystalline form of Formula 1 exhibits an XRPD pattern that is substantially similar to FIG. 23A.

In embodiments, the crystalline form of Formula 1 exhibits a differential scanning calorimetry (DSC) thermogram comprising an endothermic peak with an onset at about 49° C.

In embodiments, the crystalline form of Formula 1 exhibits an about 9% (wt %) loss between about 58° C. to about 191° C. as determined by thermogravimetric analysis (TGA).

Figure 23B:
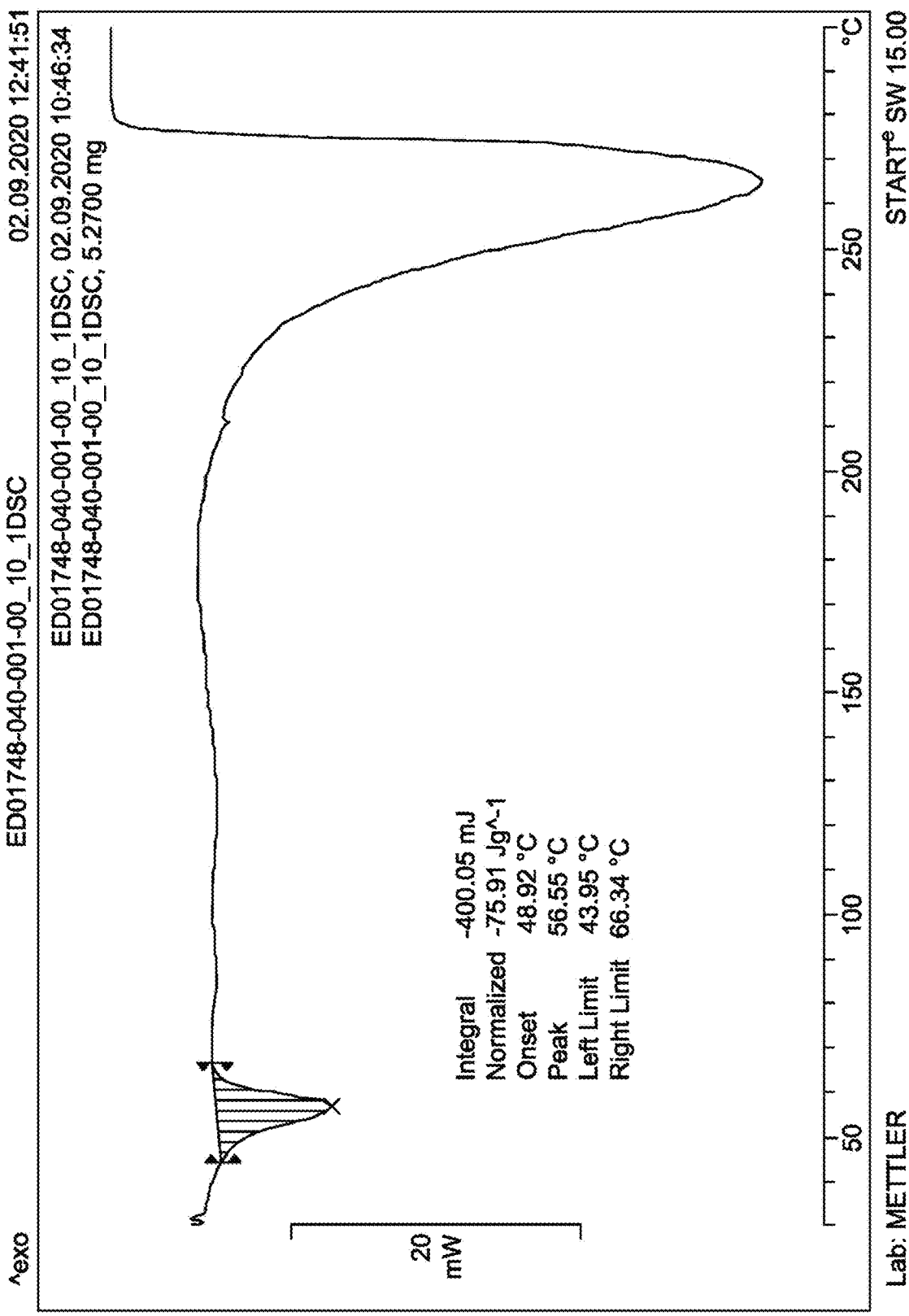
FIG. 23B shows a differential scanning calorimetry (DSC) thermogram of crystalline form Pattern 2 of Formula 1.

In embodiments, the crystalline form of Formula 1 exhibits a DSC thermogram that is substantially similar to the DSC thermogram of FIG. 23B.

Figure 23C:
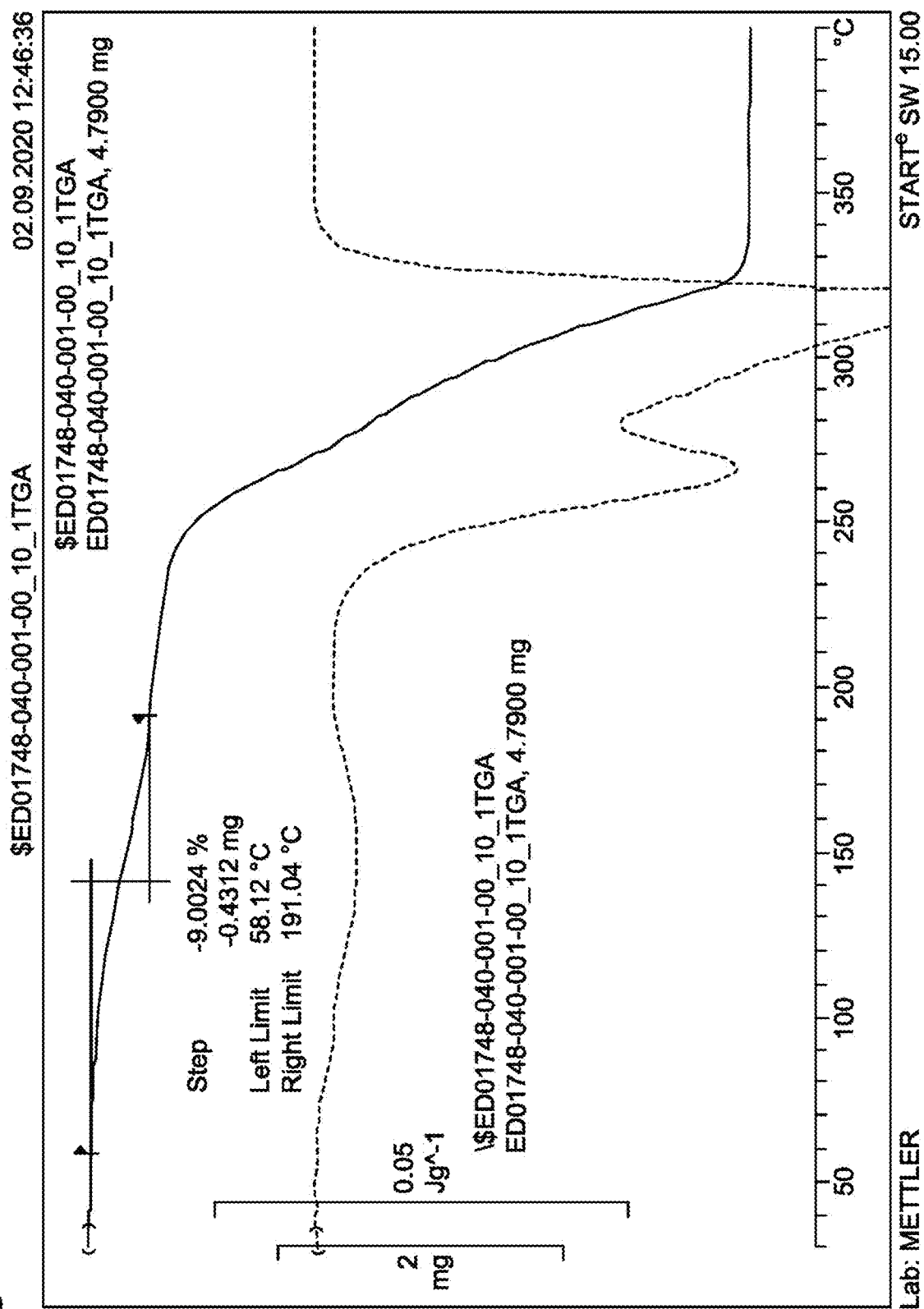
FIG. 23C shows a thermogravimetric analysis (TGA) thermogram of crystalline form Pattern 2 of Formula 1.

In embodiments, the crystalline form of Formula 1 exhibits a TGA thermogram that is substantially similar to the TGA thermogram of FIG. 23C.

In some embodiments, the crystalline form of Formula 1 is at least about 90% Pattern 2 by weight. In some embodiments, the crystalline form of Formula 1 is at least about 95% Pattern 2 by weight. In some embodiments, the crystalline form of Formula 1 is at least about 95% Pattern 2 by weight. In some embodiments, the crystalline form of Formula 1 is at least about 99% Pattern 2 by weight. In some embodiments, the crystalline form of Formula 1 is at least about 90%, about 91%, about 92%, about 93%, about 94%, about 95%, about 96%, about 97%, about 98%, or about 99% Pattern 2 by weight.

In some embodiments, the crystalline form of Formula 1 is about 70% to about 100%, about 85.0% to 100%, about 95.0% to 100% Pattern 2 by weight. In some embodiments, the crystalline form of Formula 1 is about 98.0% to 100% Pattern 2 by weight.

Crystalline Pattern 3 of Formula 1

In embodiments, the present disclosure provides a crystalline Pattern 3 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 3. In embodiments, the crystalline form of Formula 1 comprises greater than about 99%, 98%, 97%, 96%, 95%, 94%, 93%, 92%, 91%, or 90% of Pattern 3. In some embodiments, the crystalline form of Formula 1 comprises greater than about 90%, 85%, 80%, 75%, 70%, 65%, 60%, 55%, 50%, 45%, or 40% of Pattern 3.

In embodiments, the crystalline form of Formula 1 exhibits an XRPD pattern comprising peaks at 10.9, 15.8, and 17.8 °2θ with the margin of error of about ±0.2; about ±0.1; or about ±0.05. In embodiments, the XRPD of the crystalline form of Formula 1 further comprises peaks at 8.9 and 13.4 °2θ with the margin of error of about ±0.2; about ±0.1; or about ±0.05. In embodiments, the XRPD of the crystalline form of Formula 1 further comprises peaks at 17.0 and 17.5 °2θ with the margin of error of about ±0.2; about ±0.1; or about ±0.05. In embodiments, the XRPD of the crystalline form of Formula 1 further comprises at least one peak selected from 15.2, 19.8, 23.2, 24.0, 28.2, 30.4, or 30.8 °2θ with the margin of error of about ±0.2; about ±0.1; or about ±0.05. In embodiments, the XRPD of the crystalline form of Formula 1 further comprises at least two peaks selected from 15.2, 19.8, 23.2, 24.0, 28.2, 30.4, or 30.8 °2θ with the margin of error of about ±0.2; about ±0.1; or about ±0.05. In embodiments, the XRPD of the crystalline form of Formula 1 further comprises at least three peaks selected from 15.2, 19.8, 23.2, 24.0, 28.2, 30.4, or 30.8 °2θ with the margin of error of about ±0.2; about ±0.1; or about ±0.05. In embodiments, the XRPD of the crystalline form of Formula 1 further comprises at least four peaks selected from 15.2, 19.8, 23.2, 24.0, 28.2, 30.4, or 30.8 °2θ with the margin of error of about ±0.2; about ±0.1; or about ±0.05. In embodiments, the XRPD of the crystalline form of Formula 1 further comprises at least five peaks selected from 15.2, 19.8, 23.2, 24.0, 28.2, 30.4, or 30.8 °2θ with the margin of error of about ±0.2; about ±0.1; or about ±0.05. In embodiments, the XRPD of the crystalline form of Formula 1 further comprises at least six peaks selected from 15.2, 19.8, 23.2, 24.0, 28.2, 30.4, or 30.8 °2θ with the margin of error of about ±0.2; about ±0.1; or about ±0.05. In embodiments, the XRPD of the crystalline form of Formula 1 further comprises peaks at 15.2, 19.8, 23.2, 24.0, 28.2, 30.4, and 30.8 °2θ with the margin of error of about ±0.2; about ±0.1; or about ±0.05.

In embodiments, the crystalline form of the compound of Formula 1 exhibits an XRPD pattern comprising peaks at 10.9±0.2, 15.8±0.2, and 17.8±0.2 °2θ. In embodiments, the crystalline form of the compound of Formula 1 exhibits an XRPD pattern comprising peaks at 8.9±0.2 and 13.4±0.2 °2θ. In embodiments, the crystalline form of the compound of Formula 1 exhibits an XRPD pattern comprising peaks at 17.0±0.2 and 17.5±0.2 °2θ. In embodiments, the crystalline form of the compound of Formula 1 exhibits an XRPD pattern further comprising at least one peak selected from 15.2±0.2, 19.8±0.2, 23.2±0.2, 24.0±0.2, 28.2±0.2, 30.4±0.2, or 30.8±0.2 °2θ. In embodiments, the crystalline form of the compound of Formula 1 exhibits an XRPD pattern further comprising at least two peaks at 15.2±0.2, 19.8±0.2, 23.2±0.2, 24.0±0.2, 28.2±0.2, 30.4±0.2, or 30.8±0.2 °2θ. In embodiments, the crystalline form of the compound of Formula 1 exhibits an XRPD pattern further comprising at least three peaks at 15.2±0.2, 19.8±0.2, 23.2±0.2, 24.0±0.2, 28.2±0.2, 30.4±0.2, or 30.8±0.2 °2θ. In embodiments, the crystalline form of the compound of Formula 1 exhibits an XRPD pattern further comprising at least four peaks at 15.2±0.2, 19.8±0.2, 23.2±0.2, 24.0±0.2, 28.2±0.2, 30.4±0.2, or 30.8±0.2 °2θ. In embodiments, the crystalline form of the compound of Formula 1 exhibits an XRPD pattern further comprising at least five peaks at 15.2±0.2, 19.8±0.2, 23.2±0.2, 24.0±0.2, 28.2±0.2, 30.4±0.2, or 30.8±0.2 °2θ. In embodiments, the crystalline form of the compound of Formula 1 exhibits an XRPD pattern further comprising at least six peaks at 15.2±0.2, 19.8±0.2, 23.2±0.2, 24.0±0.2, 28.2±0.2, 30.4±0.2, or 30.8±0.2 °2θ. In embodiments, the crystalline form of the compound of Formula 1 exhibits an XRPD pattern further comprising peaks at 15.2±0.2, 19.8±0.2, 23.2±0.2, 24.0±0.2, 28.2±0.2, 30.4±0.2, and 30.8±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 8.

In embodiments, the crystalline form of the compound of Formula 1 exhibits an XRPD comprising peaks shown in Table 8.

In embodiments, the crystalline form of the compound of Formula 1 exhibits an XRPD pattern comprising one or more peaks from Table 8 having intensity of at least 5%. In embodiments, the crystalline form of the compound of Formula 1 exhibits an XRPD pattern comprising one or more peaks from Table 8 having intensity of at least 10%. In embodiments, the crystalline form of the compound of Formula 1 exhibits an XRPD pattern comprising one or more peaks from Table 8 having intensity of at least 20%. In embodiments, the crystalline form of the compound of Formula 1 exhibits an XRPD pattern comprising one or more peaks from Table 8 having intensity of at least 25%. In embodiments, the crystalline form of the compound of Formula 1 exhibits an XRPD pattern comprising one or more peaks from Table 8 having intensity of at least 30%. In embodiments, the crystalline form of the compound of Formula 1 exhibits an XRPD pattern comprising one or more peaks from Table 8 having intensity of at least 35%. In embodiments, the crystalline form of the compound of Formula 1 exhibits an XRPD pattern comprising one or more peaks from Table 8 having intensity of at least 40%. In embodiments, the crystalline form of the compound of Formula 1 exhibits an XRPD pattern comprising one or more peaks from Table 8 having intensity of at least 45%. In embodiments, the crystalline form of the compound of Formula 1 exhibits an XRPD pattern comprising one or more peaks from Table 8 having intensity of at least 50%. In embodiments, the crystalline form of the compound of Formula 1 exhibits an XRPD pattern comprising one or more peaks from Table 8 having intensity of at least 60%. In embodiments, the crystalline form of the compound of Formula 1 exhibits an XRPD pattern comprising one or more peaks from Table 8 having intensity of at least 70%. In embodiments, the crystalline form of the compound of Formula 1 exhibits an XRPD pattern comprising one or more peaks from Table 8 having intensity of at least 80%. In embodiments, the crystalline form of the compound of Formula 1 exhibits an XRPD pattern comprising one or more peaks from Table 8 having intensity of at least 90%.

In one specific embodiment, the crystalline form of Formula 1 exhibits an XRPD pattern that is substantially similar to the XRPD pattern of FIG. 24A.

In embodiments, the crystalline form of Formula 1 exhibits a differential scanning calorimetry (DSC) thermogram comprising an endothermic peak with an onset at about 82° C.

Figure 24B:
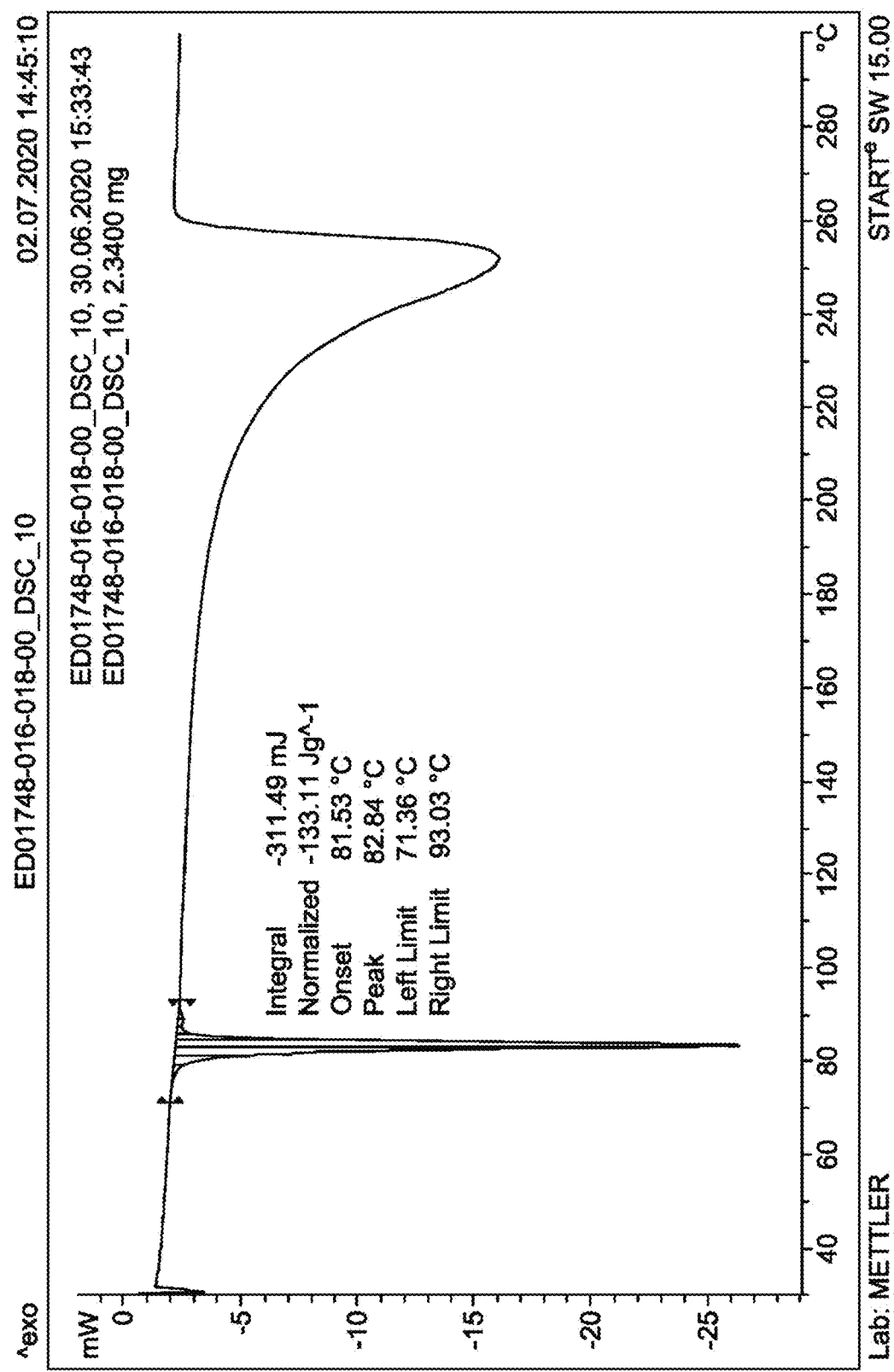
FIG. 24B shows a differential scanning calorimetry (DSC) thermogram of crystalline form Pattern 3 of Formula 1.

In embodiments, the crystalline form of Formula 1 exhibits a DSC thermogram that is substantially similar to the DSC thermogram of FIG. 24B.

Figure 24C:
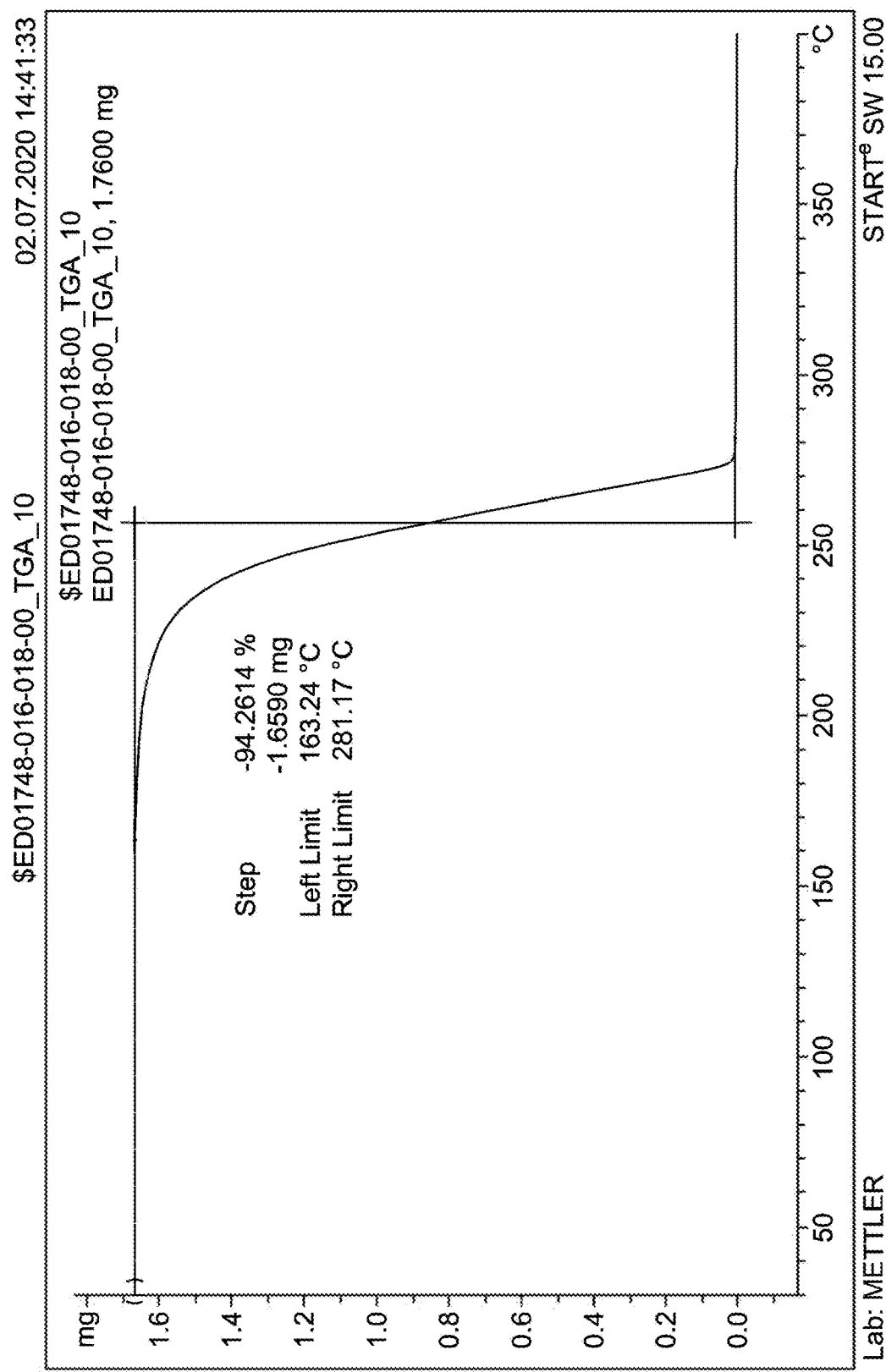
FIG. 24C shows a thermogravimetric analysis (TGA) thermogram of crystalline form Pattern 3 of Formula 1.

In embodiments, the crystalline form of Formula 1 exhibits a TGA thermogram that is substantially similar to the TGA thermogram of FIG. 24C.

In some embodiments, the crystalline form of Formula 1 is at least about 90% Pattern 3 by weight. In some embodiments, the crystalline form of Formula 1 is at least about 95% Pattern 3 by weight. In some embodiments, the crystalline form of Formula 1 is at least about 95% Pattern 3 by weight. In some embodiments, the crystalline form of Formula 1 is at least about 99% Pattern 3 by weight. In some embodiments, the crystalline form of Formula 1 is at least about 90%, about 91%, about 92%, about 93%, about 94%, about 95%, about 96%, about 97%, about 98%, or about 99% Pattern 3 by weight.

In some embodiments, the crystalline form of Formula 1 is about 70% to about 100%, about 85.0% to 100%, or about 95.0% to 100% Pattern 3 by weight. In some embodiments, the crystalline form of Formula 1 is about 98.0% to 100% Pattern 3 by weight.

Crystalline Pattern 4 of Formula 1

In embodiments, the present disclosure provides a crystalline Pattern 4 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 4. In embodiments, the crystalline form of Formula 1 comprises greater than about 99%, 98%, 97%, 96%, 95%, 94%, 93%, 92%, 91%, or 90% of Pattern 4. In some embodiments, the crystalline form of Formula 1 comprises greater than about 90%, 85%, 80%, 75%, 70%, 65%, 60%, 55%, 50%, 45%, or 40% of Pattern 4.

In embodiments, the crystalline form of Formula 1 exhibits an XRPD pattern comprising peaks at 8.6, 17.3, and 17.4 °2θ with the margin of error of about ±0.2; about ±0.1; or about ±0.05. In embodiments, the XRPD of the crystalline form Formula 1 further comprises peaks at 13.7 or 28.5 °2θ with the margin of error of about ±0.2; about ±0.1; or about ±0.05. In embodiments, the XRPD of the crystalline form of Formula 1 further comprises peaks at 13.4 or 20.1 °2θ with the margin of error of about ±0.2; about ±0.1; or about ±0.05. In embodiments, the XRPD of the crystalline form of Formula 1 further comprises at least one peak at 6.9, 17.0, 19.6, 25.4, 26.1, 26.8, or 32.1 °2θ with the margin of error of about ±0.2; about ±0.1; or about ±0.05. In embodiments, the XRPD of the crystalline form of Formula 1 further comprises at least two peaks selected from 6.9, 17.0, 19.6, 25.4, 26.1, 26.8, or 32.1 °2θ with the margin of error of about ±0.2; about ±0.1; or about ±0.05. In embodiments, the XRPD of the crystalline form of Formula 1 further comprises at least three peaks selected from 6.9, 17.0, 19.6, 25.4, 26.1, 26.8, or 32.1 °2θ with the margin of error of about ±0.2; about ±0.1; or about ±0.05. In embodiments, the XRPD of the crystalline form of Formula 1 further comprises at least four peaks selected from 6.9, 17.0, 19.6, 25.4, 26.1, 26.8, or 32.1 °2θ with the margin of error of about ±0.2; about ±0.1; or about ±0.05. In embodiments, the XRPD of the crystalline form of Formula 1 further comprises at least five peaks selected from 6.9, 17.0, 19.6, 25.4, 26.1, 26.8, or 32.1 °2θ with the margin of error of about ±0.2; about ±0.1; or about ±0.05. In embodiments, the XRPD of the crystalline form of Formula 1 further comprises at least six peaks selected from 6.9, 17.0, 19.6, 25.4, 26.1, 26.8, or 32.1 °2θ with the margin of error of about ±0.2; about ±0.1; or about ±0.05. In embodiments, the XRPD of the crystalline form of Formula 1 further comprises peaks at 6.9, 17.0, 19.6, 25.4, 26.1, 26.8, and 32.1 °2θ with the margin of error of about ±0.2; about ±0.1; or about ±0.05.

In embodiments, the crystalline form of the compound of Formula 1 exhibits an XRPD pattern comprising peaks at 8.6±0.2, 17.3±0.2, and 17.4±0.2 °2θ. In embodiments, the crystalline form of the compound of Formula 1 exhibits an XRPD pattern comprising peaks at 13.7±0.2 or 28.5±0.2 °2θ. In embodiments, the crystalline form of the compound of Formula 1 exhibits an XRPD pattern comprising peaks at 13.4±0.2 or 20.1±0.2 °2θ. In embodiments, the crystalline form of the compound of Formula 1 exhibits an XRPD pattern comprising at least one peak at 6.9±0.2, 17.0±0.2, 19.6±0.2, 25.4±0.2, 26.1±0.2, 26.8±0.2, or 32.1±0.2 °2θ. In embodiments, the crystalline form of the compound of Formula 1 exhibits an XRPD pattern comprising at least two peaks selected from 6.9±0.2, 17.0±0.2, 19.6±0.2, 25.4±0.2, 26.1±0.2, 26.8±0.2, or 32.1±0.2 °2θ. In embodiments, the crystalline form of the compound of Formula 1 exhibits an XRPD pattern comprising at least three peaks selected from 6.9±0.2, 17.0±0.2, 19.6±0.2, 25.4±0.2, 26.1±0.2, 26.8±0.2, or 32.1±0.2 °2θ. In embodiments, the crystalline form of the compound of Formula 1 exhibits an XRPD pattern comprising at least four peaks selected from 6.9±0.2, 17.0±0.2, 19.6±0.2, 25.4±0.2, 26.1±0.2, 26.8±0.2, or 32.1±0.2 °2θ. In embodiments, the crystalline form of the compound of Formula 1 exhibits an XRPD pattern comprising at least five peaks selected from 6.9±0.2, 17.0±0.2, 19.6±0.2, 25.4±0.2, 26.1±0.2, 26.8±0.2, or 32.1±0.2 °2θ. In embodiments, the crystalline form of the compound of Formula 1 exhibits an XRPD pattern comprising at least six peaks selected from 6.9±0.2, 17.0±0.2, 19.6±0.2, 25.4±0.2, 26.1±0.2, 26.8±0.2, or 32.1±0.2 °2θ. In embodiments, the crystalline form of the compound of Formula 1 exhibits an XRPD pattern comprising peaks at 6.9±0.2, 17.0±0.2, 19.6±0.2, 25.4±0.2, 26.1±0.2, 26.8±0.2, and 32.1±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 9.

In embodiments, the crystalline form of the compound of Formula 1 exhibits an XRPD comprising peaks shown in Table 9.

In embodiments, the crystalline form of the compound of Formula 1 exhibits an XRPD pattern comprising one or more peaks from Table 9 having intensity of at least 5%. In embodiments, the crystalline form of the compound of Formula 1 exhibits an XRPD pattern comprising one or more peaks from Table 9 having intensity of at least 10%. In embodiments, the crystalline form of the compound of Formula 1 exhibits an XRPD pattern comprising one or more peaks from Table 9 having intensity of at least 20%. In embodiments, the crystalline form of the compound of Formula 1 exhibits an XRPD pattern comprising one or more peaks from Table 9 having intensity of at least 25%. In embodiments, the crystalline form of the compound of Formula 1 exhibits an XRPD pattern comprising one or more peaks from Table 9 having intensity of at least 30%. In embodiments, the crystalline form of the compound of Formula 1 exhibits an XRPD pattern comprising one or more peaks from Table 9 having intensity of at least 35%. In embodiments, the crystalline form of the compound of Formula 1 exhibits an XRPD pattern comprising one or more peaks from Table 9 having intensity of at least 40%. In embodiments, the crystalline form of the compound of Formula 1 exhibits an XRPD pattern comprising one or more peaks from Table 9 having intensity of at least 45%. In embodiments, the crystalline form of the compound of Formula 1 exhibits an XRPD pattern comprising one or more peaks from Table 9 having intensity of at least 50%. In embodiments, the crystalline form of the compound of Formula 1 exhibits an XRPD pattern comprising one or more peaks from Table 9 having intensity of at least 60%. In embodiments, the crystalline form of the compound of Formula 1 exhibits an XRPD pattern comprising one or more peaks from Table 9 having intensity of at least 70%. In embodiments, the crystalline form of the compound of Formula 1 exhibits an XRPD pattern comprising one or more peaks from Table 9 having intensity of at least 80%. In embodiments, the crystalline form of the compound of Formula 1 exhibits an XRPD pattern comprising one or more peaks from Table 9 having intensity of at least 90%.

Figure 25A:
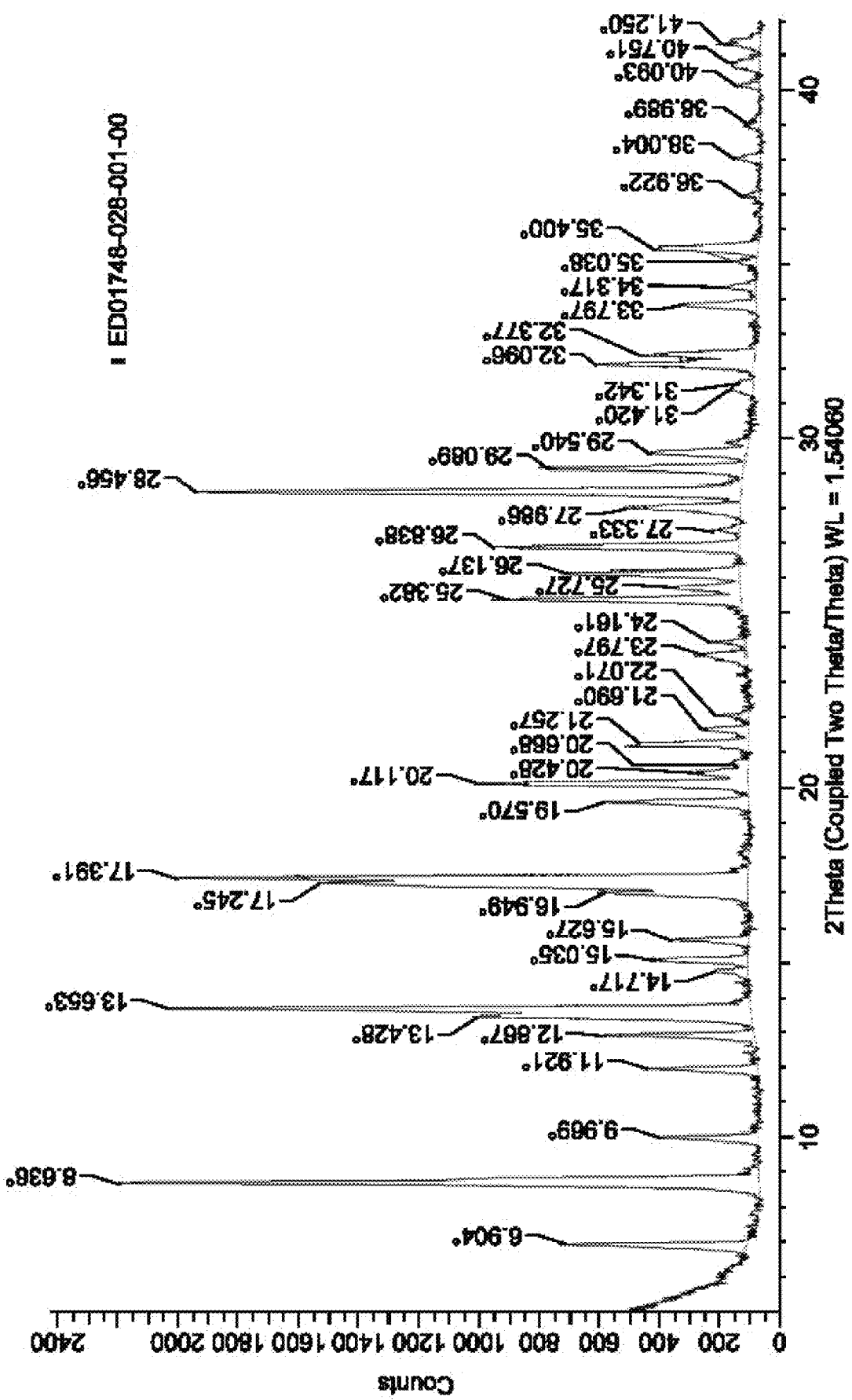
FIG. 25A shows an X-ray powder diffraction (XRPD) pattern of crystalline form Pattern 4 of Formula 1.

In one specific embodiment, the crystalline form of Formula 1 exhibits an XRPD pattern that is substantially similar to FIG. 25A.

In some embodiments, the crystalline form of Formula 1 is at least about 90% Pattern 4 by weight. In some embodiments, the crystalline form of Formula 1 is at least about 95% Pattern 4 by weight. In some embodiments, the crystalline form of Formula 1 is at least about 95% Pattern 4 by weight. In some embodiments, the crystalline form of Formula 1 is at least about 99% Pattern 4 by weight. In some embodiments, the crystalline form of Formula 1 is at least about 90%, about 91%, about 92%, about 93%, about 94%, about 95%, about 96%, about 97%, about 98%, or about 99% Pattern 4 by weight.

In some embodiments, the crystalline form of Formula 1 is about 70% to about 100%, about 85.0% to 100%, or about 95.0% to 100% Pattern 4 by weight. In some embodiments, the crystalline form of Formula 1 is about 98.0% to 100% Pattern 4 by weight.

Crystalline Pattern 5 of Formula 1

In embodiments, the present disclosure provides a crystalline Pattern 5 of the compound of Formula 1.

In embodiments, the crystalline form of Formula 5 comprises greater than about 99.9%, about 99.8%, about 99.7%, about 99.6%, about 99.5%, about 99.4%, about 99.3%, about 99.2%, about 99.1%, or about 99.0% of Pattern 5. In embodiments, the crystalline form of Formula 1 comprises greater than about 99%, 98%, 97%, 96%, 95%, 94%, 93%, 92%, 91%, or 90% of Pattern 5. In some embodiments, the crystalline form of Formula 1 comprises greater than about 90%, 85%, 80%, 75%, 70%, 65%, 60%, 55%, 50%, 45%, or 40% of Pattern 5.

In embodiments, the crystalline form of Formula 1 exhibits an XRPD pattern comprising peaks at 13.3, 15.8 and 17.8 °2θ with the margin of error of about ±0.2; about ±0.1; or about ±0.05. In embodiments, the crystalline form of Formula 1 exhibits an XRPD pattern further comprising peaks at 10.9 and 19.8 °2θ with the margin of error of about ±0.2; about ±0.1; or about ±0.05. In embodiments, the crystalline form of Formula 1 exhibits an XRPD pattern further comprising at least one peak at 6.6, 8.9, 13.2, 16.2, 17.0, 17.5, or 19.4 °2θ with the margin of error of about ±0.2; about ±0.1; or about ±0.05. In embodiments, the crystalline form of Formula 1 exhibits an XRPD pattern further comprising at least two peaks selected from 6.6, 8.9, 13.2, 16.2, 17.0, 17.5, or 19.4 °2θ with the margin of error of about ±0.2; about ±0.1; or about ±0.05. In embodiments, the crystalline form of Formula 1 exhibits an XRPD pattern further comprising at least three peaks selected from 6.6, 8.9, 13.2, 16.2, 17.0, 17.5, or 19.4 °2θ with the margin of error of about ±0.2; about ±0.1; or about ±0.05. In embodiments, the crystalline form of Formula 1 exhibits an XRPD pattern further comprising at least four peaks selected from 6.6, 8.9, 13.2, 16.2, 17.0, 17.5, or 19.4 °2θ with the margin of error of about ±0.2; about ±0.1; or about ±0.05. In embodiments, the crystalline form of Formula 1 exhibits an XRPD pattern further comprising at least five peaks selected from 6.6, 8.9, 13.2, 16.2, 17.0, 17.5, or 19.4 °2θ with the margin of error of about ±0.2; about ±0.1; or about ±0.05. In embodiments, the crystalline form of Formula 1 exhibits an XRPD pattern further comprising at least six peaks selected from 6.6, 8.9, 13.2, 16.2, 17.0, 17.5, or 19.4 °2θ with the margin of error of about ±0.2; about ±0.1; or about ±0.05. In embodiments, the crystalline form of Formula 1 exhibits an XRPD pattern further comprising peaks at 6.6, 8.9, 13.2, 16.2, 17.0, 17.5, and 19.4 °2θ with the margin of error of about ±0.2; about ±0.1; or about ±0.05.

In embodiments, the crystalline form of Formula 1 exhibits an XRPD pattern comprising peaks at 13.3±0.2, 15.8±0.2 and 17.8±0.2 °2θ. In embodiments, the crystalline form of Formula 1 exhibits an XRPD pattern further comprising peaks at 10.9±0.2 and 19.8±0.2 °2θ. In embodiments, the crystalline form of Formula 1 exhibits an XRPD pattern further comprising at least one peak at 6.6±0.2, 8.9±0.2, 13.2±0.2, 16.2±0.2, 17.0±0.2, 17.5±0.2, or 19.4±0.2 °2θ. In embodiments, the crystalline form of Formula 1 exhibits an XRPD pattern further comprising at least two peaks selected from 6.6±0.2, 8.9±0.2, 13.2±0.2, 16.2±0.2, 17.0±0.2, 17.5±0.2, or 19.4±0.2 °2θ. In embodiments, the crystalline form of Formula 1 exhibits an XRPD pattern further comprising at least three peaks selected from 6.6±0.2, 8.9±0.2, 13.2±0.2, 16.2±0.2, 17.0±0.2, 17.5±0.2, or 19.4±0.2 °2θ. In embodiments, the crystalline form of Formula 1 exhibits an XRPD pattern further comprising at least four peaks selected from 6.6±0.2, 8.9±0.2, 13.2±0.2, 16.2±0.2, 17.0±0.2, 17.5±0.2, or 19.4±0.2 °2θ. In embodiments, the crystalline form of Formula 1 exhibits an XRPD pattern further comprising at least five peaks selected from 6.6±0.2, 8.9±0.2, 13.2±0.2, 16.2±0.2, 17.0±0.2, 17.5±0.2, or 19.4±0.2 °2θ. In embodiments, the crystalline form of Formula 1 exhibits an XRPD pattern further comprising at least six peaks selected from 6.6±0.2, 8.9±0.2, 13.2±0.2, 16.2±0.2, 17.0±0.2, 17.5±0.2, or 19.4±0.2 °2θ. In embodiments, the crystalline form of Formula 1 exhibits an XRPD pattern further comprising peaks at 6.6±0.2, 8.9±0.2, 13.2±0.2, 16.2±0.2, 17.0±0.2, 17.5±0.2, and 19.4±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks Table 10.

In embodiments, the crystalline form of the compound of Formula 1 exhibits an XRPD comprising peaks shown in Table 10.

In embodiments, the crystalline form of the compound of Formula 1 exhibits an XRPD pattern comprising one or more peaks from Table 10 having intensity of at least 5%. In embodiments, the crystalline form of the compound of Formula 1 exhibits an XRPD pattern comprising one or more peaks from Table 10 having intensity of at least 10%. In embodiments, the crystalline form of the compound of Formula 1 exhibits an XRPD pattern comprising one or more peaks from Table 10 having intensity of at least 20%. In embodiments, the crystalline form of the compound of Formula 1 exhibits an XRPD pattern comprising one or more peaks from Table 10 having intensity of at least 25%. In embodiments, the crystalline form of the compound of Formula 1 exhibits an XRPD pattern comprising one or more peaks from Table 10 having intensity of at least 30%. In embodiments, the crystalline form of the compound of Formula 1 exhibits an XRPD pattern comprising one or more peaks from Table 10 having intensity of at least 35%. In embodiments, the crystalline form of the compound of Formula 1 exhibits an XRPD pattern comprising one or more peaks from Table 10 having intensity of at least 40%. In embodiments, the crystalline form of the compound of Formula 1 exhibits an XRPD pattern comprising one or more peaks from Table 10 having intensity of at least 45%. In embodiments, the crystalline form of the compound of Formula 1 exhibits an XRPD pattern comprising one or more peaks from Table 10 having intensity of at least 50%. In embodiments, the crystalline form of the compound of Formula 1 exhibits an XRPD pattern comprising one or more peaks from Table 10 having intensity of at least 60%. In embodiments, the crystalline form of the compound of Formula 1 exhibits an XRPD pattern comprising one or more peaks from Table 10 having intensity of at least 70%. In embodiments, the crystalline form of the compound of Formula 1 exhibits an XRPD pattern comprising one or more peaks from Table 10 having intensity of at least 80%. In embodiments, the crystalline form of the compound of Formula 1 exhibits an XRPD pattern comprising one or more peaks from Table 10 having intensity of at least 90%.

Figure 26A:
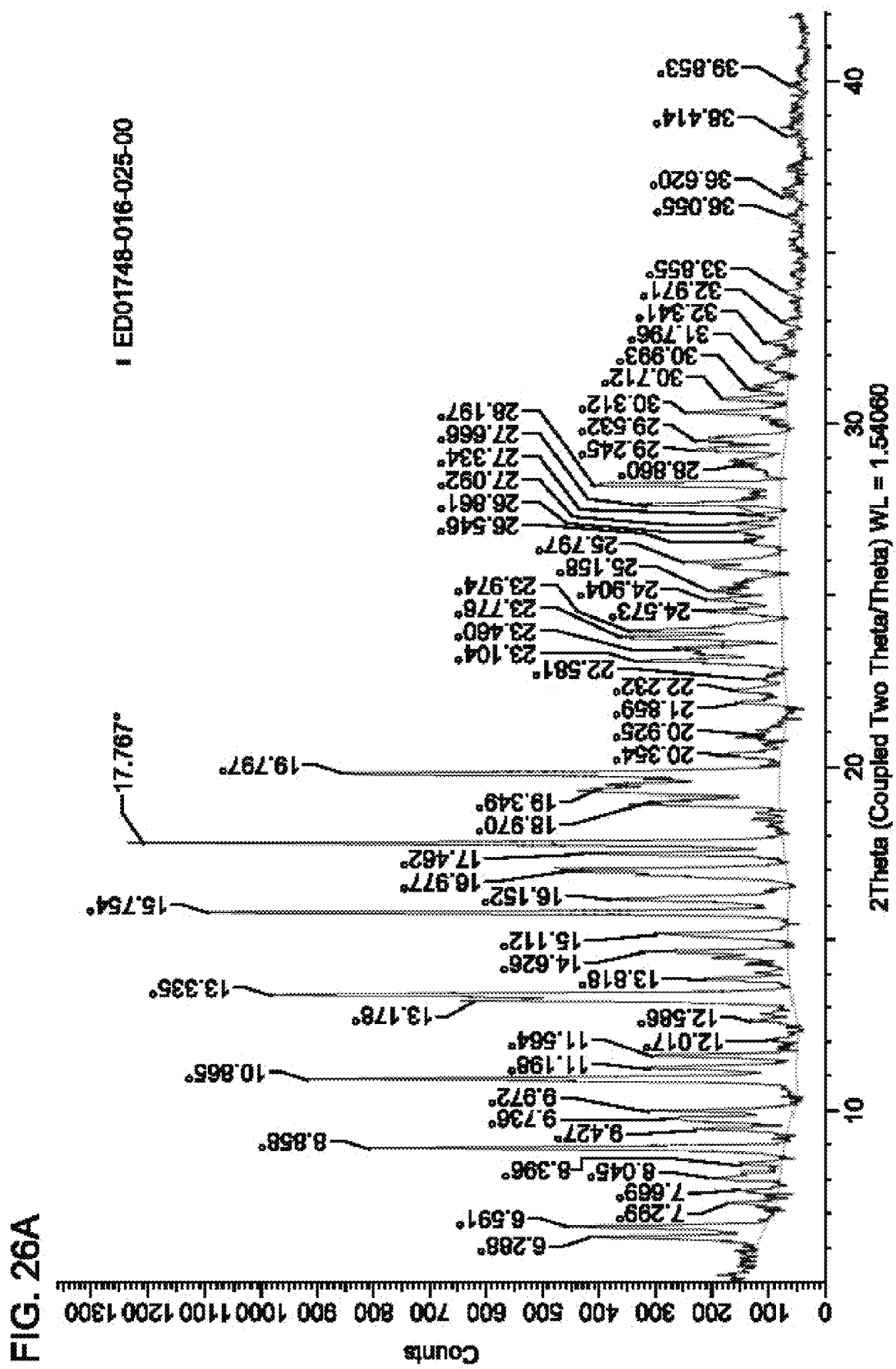
FIG. 26A shows an X-ray powder diffraction (XRPD) pattern of crystalline form Pattern 5 of Formula 1.

In one specific embodiment, the crystalline form of Formula 1 exhibits an XRPD pattern that is substantially similar to FIG. 26A.

In some embodiments, the crystalline form of Formula 1 is at least about 90% Pattern 5 by weight. In some embodiments, the crystalline form of Formula 1 is at least about 95% Pattern 5 by weight. In some embodiments, the crystalline form of Formula 1 is at least about 95% Pattern 5 by weight. In some embodiments, the crystalline form of Formula 1 is at least about 99% Pattern 5 by weight. In some embodiments, the crystalline form of Formula 1 is at least about 90%, about 91%, about 92%, about 93%, about 94%, about 95%, about 96%, about 97%, about 98%, or about 99% Pattern 5 by weight.

In some embodiments, the crystalline form of Formula 1 is about 70% to about 100%, about 85.0% to 100%, or about 95.0% to 100% Pattern 5 by weight. In some embodiments, the crystalline form of Formula 1 is about 98.0% to 100% Pattern 5 by weight.

Crystalline Pattern 6 of Formula 1

In embodiments, the present disclosure provides a crystalline Pattern 6 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 6. In embodiments, the crystalline form of Formula 1 comprises greater than about 99%, 98%, 97%, 96%, 95%, 94%, 93%, 92%, 91%, or 90% of Pattern 6. In some embodiments, the crystalline form of Formula 1 comprises greater than about 90%, 85%, 80%, 75%, 70%, 65%, 60%, 55%, 50%, 45%, or 40% of Pattern 6.

In embodiments, the crystalline form of Formula 1 exhibits an XRPD pattern comprising peaks at 6.6, 14.1, and 16.4 °2θ with the margin of error of about ±0.2; about ±0.1; or about ±0.05. In embodiments, the crystalline form of Formula 1 exhibits an XRPD pattern further comprising peaks at 10.0 and 19.9 °2θ with the margin of error of about ±0.2; about ±0.1; or about ±0.05. In embodiments, the crystalline form of Formula 1 exhibits an XRPD pattern further comprising peaks at 8.3, and 28.4 °2θ with the margin of error of about ±0.2; about ±0.1; or about ±0.05. In embodiments, the crystalline form of the compound of Formula 1 exhibits an XRPD pattern comprising peaks at 16.4, 16.6, 20.5, and 25.6 °2θ with the margin of error of about ±0.2; about ±0.1; or about ±0.05. In embodiments, the crystalline form of the compound of Formula 1 exhibits an XRPD pattern comprising peaks at 6.6 and 14.1 °2θ with the margin of error of about ±0.2; about ±0.1; or about ±0.05. In embodiments, the crystalline form of the compound of Formula 1 exhibits an XRPD pattern comprising peaks at 10.0 and 19.9 °2θ with the margin of error of about ±0.2; about ±0.1; or about ±0.05. In embodiments, the crystalline form of the compound of Formula 1 exhibits an XRPD pattern comprising at least one peak at 8.3, 19.3, 22.5, 25.6, 25.9, or 28.4 °2θ with the margin of error of about ±0.2; about ±0.1; or about ±0.05. In embodiments, the crystalline form of the compound of Formula 1 exhibits an XRPD pattern comprising at least two peaks selected from 8.3, 19.3, 22.5, 25.6, 25.9, or 28.4 °2θ with the margin of error of about ±0.2; about ±0.1; or about ±0.05. In embodiments, the crystalline form of the compound of Formula 1 exhibits an XRPD pattern comprising at least three peaks selected from 8.3, 19.3, 22.5, 25.6, 25.9, or 28.4 °2θ with the margin of error of about ±0.2; about ±0.1; or about ±0.05. In embodiments, the crystalline form of the compound of Formula 1 exhibits an XRPD pattern comprising at least four peaks selected from 8.3, 19.3, 22.5, 25.6, 25.9, or 28.4 °2θ with the margin of error of about ±0.2; about ±0.1; or about ±0.05. In embodiments, the crystalline form of the compound of Formula 1 exhibits an XRPD pattern comprising at least five peaks selected from 8.3, 19.3, 22.5, 25.6, 25.9, or 28.4 °2θ with the margin of error of about ±0.2; about ±0.1; or about ±0.05. In embodiments, the crystalline form of the compound of Formula 1 exhibits an XRPD pattern comprising peaks at 8.3, 19.3, 22.5, 25.6, 25.9, and 28.4 °2θ with the margin of error of about ±0.2; about ±0.1; or about ±0.05.

In embodiments, the crystalline form of the compound of Formula 1 exhibits an XRPD pattern comprising peaks at 6.6±0.2, 14.1±0.2, and 16.4±0.2 °2θ. In embodiments, the crystalline form of the compound of Formula 1 exhibits an XRPD pattern comprising peaks at 10.0±0.2, and 19.9±0.2 °2θ. In embodiments, the crystalline form of the compound of Formula 1 exhibits an XRPD pattern comprising peaks at 8.3±0.2, and 28.4±0.2 °2θ.

In embodiments, the crystalline form of the compound of Formula 1 exhibits an XRPD pattern comprising peaks at 16.4±0.2, 16.6±0.2, 20.5±0.2, and 25.6±0.2 °2θ. In embodiments, the crystalline form of the compound of Formula 1 exhibits an XRPD pattern comprising peaks at 6.6±0.2 and 14.1±0.2 °2θ. In embodiments, the crystalline form of the compound of Formula 1 exhibits an XRPD pattern comprising peaks at 10.0±0.2 and 19.9±0.2 °2θ. In embodiments, the crystalline form of the compound of Formula 1 exhibits an XRPD pattern comprising at least one peak at 8.3±0.2, 19.3±0.2, 22.5±0.2, 25.6±0.2, 25.9±0.2, or 28.4±0.2 °2θ. In embodiments, the crystalline form of the compound of Formula 1 exhibits an XRPD pattern comprising at least two peaks selected from 8.3±0.2, 19.3±0.2, 22.5±0.2, 25.6±0.2, 25.9±0.2, or 28.4±0.2 °2θ. In embodiments, the crystalline form of the compound of Formula 1 exhibits an XRPD pattern comprising at least three peaks selected from 8.3±0.2, 19.3±0.2, 22.5±0.2, 25.6±0.2, 25.9±0.2, or 28.4±0.2 °2θ. In embodiments, the crystalline form of the compound of Formula 1 exhibits an XRPD pattern comprising at least four peaks selected from 8.3±0.2, 19.3±0.2, 22.5±0.2, 25.6±0.2, 25.9±0.2, or 28.4±0.2 °2θ. In embodiments, the crystalline form of the compound of Formula 1 exhibits an XRPD pattern comprising at least five peaks selected from 8.3±0.2, 19.3±0.2, 22.5±0.2, 25.6±0.2, 25.9±0.2, or 28.4±0.2 °2θ. In embodiments, the crystalline form of the compound of Formula 1 exhibits an XRPD pattern comprising peaks selected from 8.3±0.2, 19.3±0.2, 22.5±0.2, 25.6±0.2, 25.9±0.2, and 28.4±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 11.

In embodiments, the crystalline form of the compound of Formula 1 exhibits an XRPD comprising peaks shown in Table 11.

In embodiments, the crystalline form of the compound of Formula 1 exhibits an XRPD pattern comprising one or more peaks from Table 11 having intensity of at least 5%. In embodiments, the crystalline form of the compound of Formula 1 exhibits an XRPD pattern comprising one or more peaks from Table 11 having intensity of at least 10%. In embodiments, the crystalline form of the compound of Formula 1 exhibits an XRPD pattern comprising one or more peaks from Table 11 having intensity of at least 20%. In embodiments, the crystalline form of the compound of Formula 1 exhibits an XRPD pattern comprising one or more peaks from Table 11 having intensity of at least 25%. In embodiments, the crystalline form of the compound of Formula 1 exhibits an XRPD pattern comprising one or more peaks from Table 11 having intensity of at least 30%. In embodiments, the crystalline form of the compound of Formula 1 exhibits an XRPD pattern comprising one or more peaks from Table 11 having intensity of at least 35%. In embodiments, the crystalline form of the compound of Formula 1 exhibits an XRPD pattern comprising one or more peaks from Table 11 having intensity of at least 40%. In embodiments, the crystalline form of the compound of Formula 1 exhibits an XRPD pattern comprising one or more peaks from Table 11 having intensity of at least 45%. In embodiments, the crystalline form of the compound of Formula 1 exhibits an XRPD pattern comprising one or more peaks from Table 11 having intensity of at least 50%. In embodiments, the crystalline form of the compound of Formula 1 exhibits an XRPD pattern comprising one or more peaks from Table 11 having intensity of at least 60%. In embodiments, the crystalline form of the compound of Formula 1 exhibits an XRPD pattern comprising one or more peaks from Table 11 having intensity of at least 70%. In embodiments, the crystalline form of the compound of Formula 1 exhibits an XRPD pattern comprising one or more peaks from Table 11 having intensity of at least 80%. In embodiments, the crystalline form of the compound of Formula 1 exhibits an XRPD pattern comprising one or more peaks from Table 11 having intensity of at least 90%.

Figure 27A:
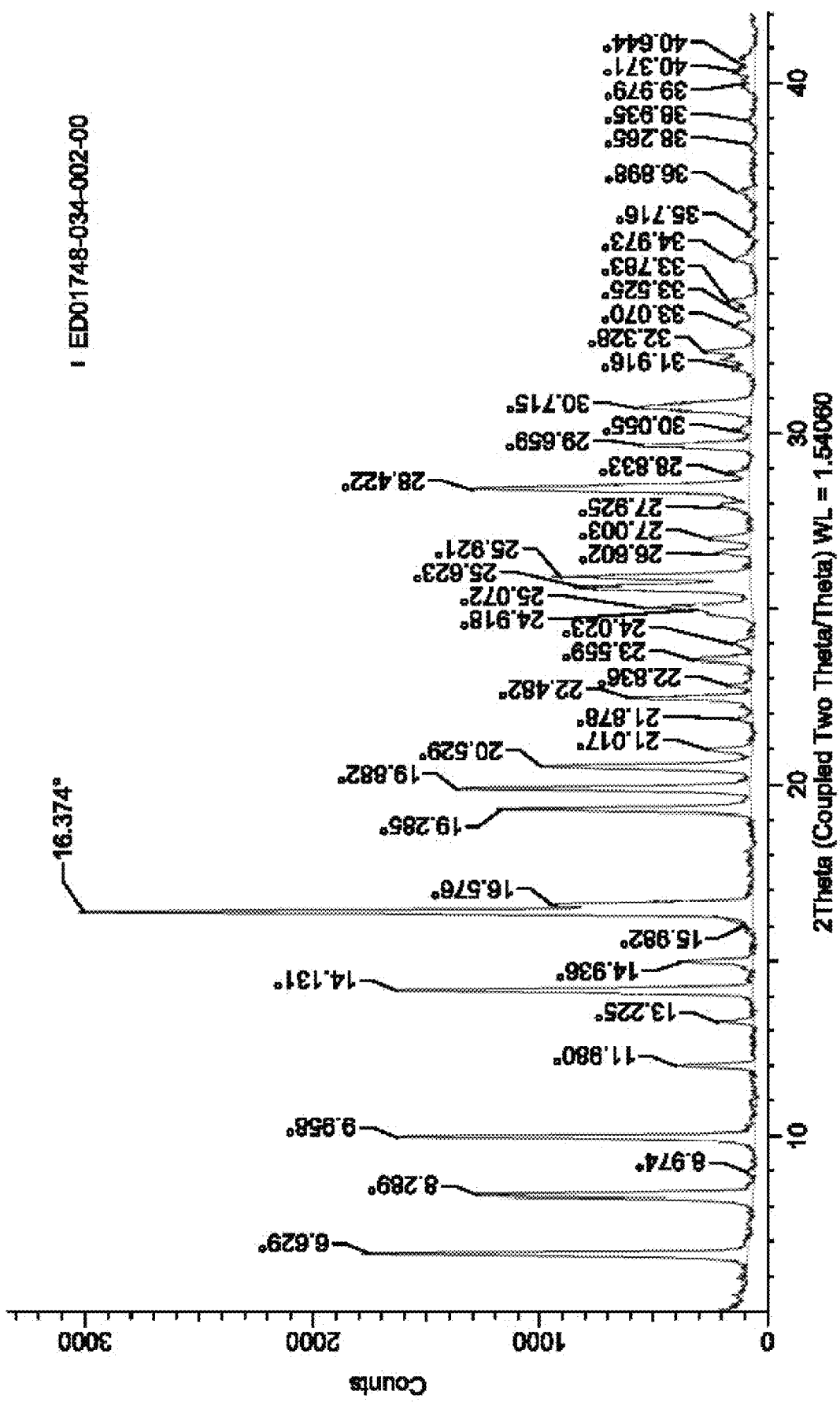
FIG. 27A shows an X-ray powder diffraction (XRPD) pattern of crystalline form Pattern 6 of Formula 1.

In one specific embodiment, the crystalline form of Formula 1 exhibits an XRPD pattern that is substantially similar to FIG. 27A.

In embodiments, the crystalline form of Formula 1 exhibits a differential scanning calorimetry (DSC) thermogram comprising an endothermic peak with an onset at about 72° C.

In embodiments, the crystalline form of Formula 1 exhibits an about 4.8% (wt %) loss between about 70° C. to about 161° C. as determined by thermogravimetric analysis (TGA).

Figure 27B:
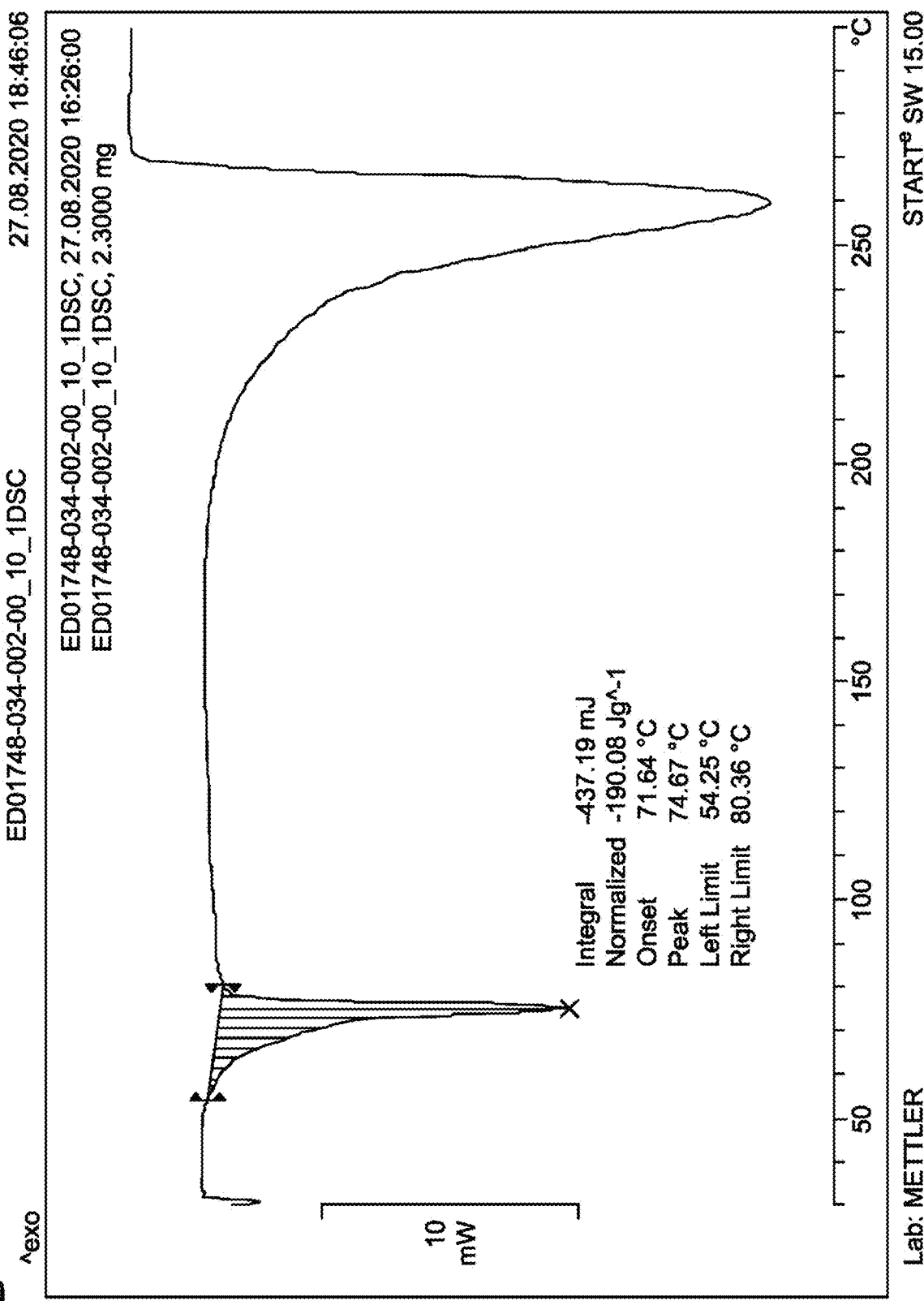
FIG. 27B shows a differential scanning calorimetry (DSC) thermogram of crystalline form Pattern 6 of Formula 1.

In embodiments, the crystalline form of Formula 1 exhibits a DSC thermogram that is substantially similar to the DSC thermogram of FIG. 27B.

Figure 27C:
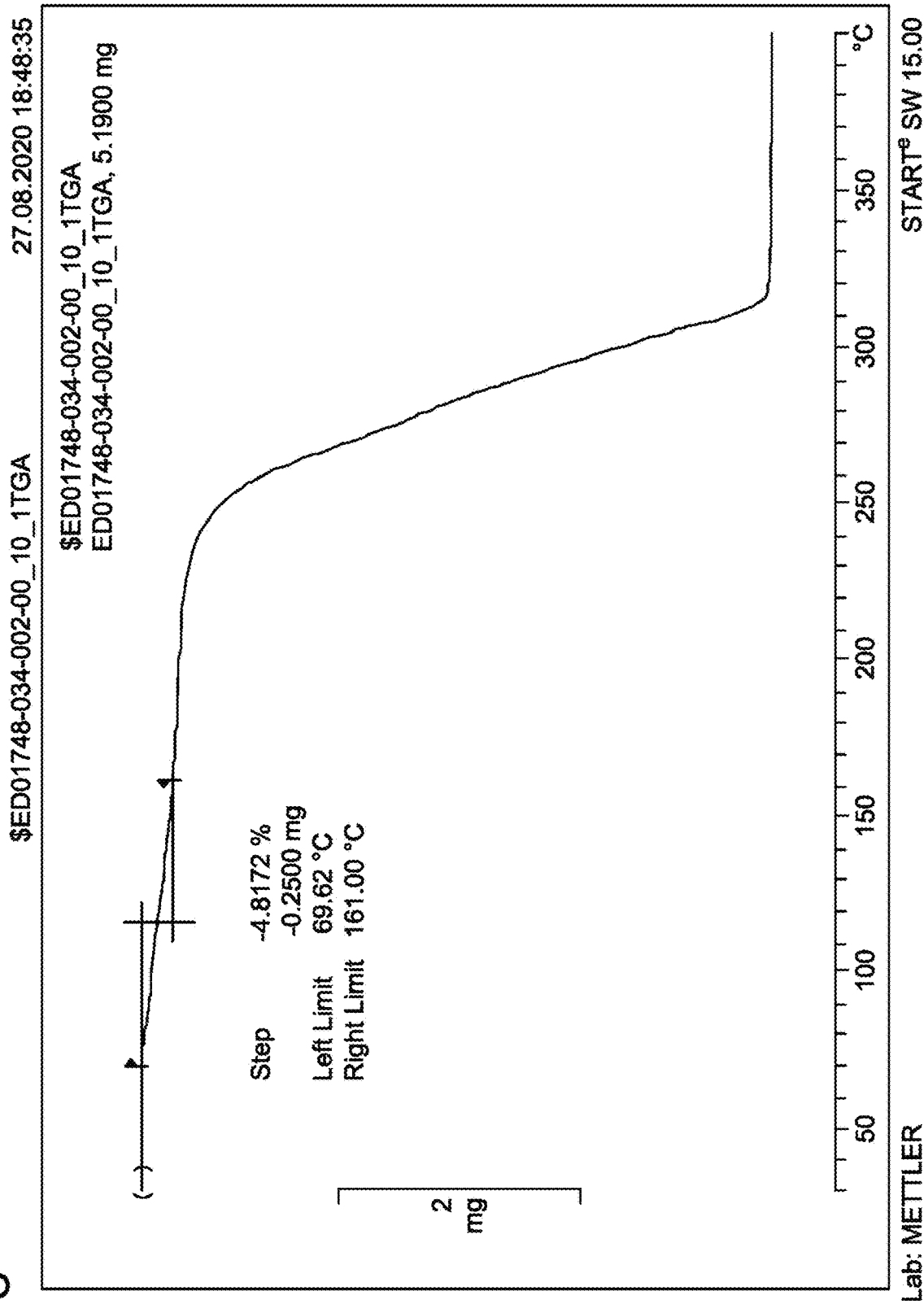
FIG. 27C shows a thermogravimetric analysis (TGA) thermogram of crystalline form Pattern 6 of Formula 1.

In embodiments, the crystalline form of Formula 1 exhibits a TGA thermogram that is substantially similar to the TGA thermogram of FIG. 27C.

In some embodiments, the crystalline form of Formula 1 is at least about 90% Pattern 6 by weight. In some embodiments, the crystalline form of Formula 1 is at least about 95% Pattern 6 by weight. In some embodiments, the crystalline form of Formula 1 is at least about 95% Pattern 6 by weight. In some embodiments, the crystalline form of Formula 1 is at least about 99% Pattern 6 by weight. In some embodiments, the crystalline form of Formula 1 is at least about 90%, about 91%, about 92%, about 93%, about 94%, about 95%, about 96%, about 97%, about 98%, or about 99% Pattern 6 by weight.

In some embodiments, the crystalline form of Formula 1 is about 70% to about 100%, about 85.0% to 100%, or about 95.0% to 100% Pattern 6 by weight. In some embodiments, the crystalline form of Formula 1 is about 98.0% to 100% Pattern 6 by weight.

Crystalline Pattern 7 of Formula 1

In embodiments, the present disclosure provides a crystalline Pattern 7 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 7. In embodiments, the crystalline form of Formula 1 comprises greater than about 99%, 98%, 97%, 96%, 95%, 94%, 93%, 92%, 91%, or 90% of Pattern 7. In some embodiments, the crystalline form of Formula 1 comprises greater than about 90%, 85%, 80%, 75%, 70%, 65%, 60%, 55%, 50%, 45%, or 40% of Pattern 7.

In embodiments, the crystalline form of Formula 1 exhibits an XRPD pattern comprising peaks at 10.0, 15.0, and 16.3 °2θ with the margin of error of about ±0.2; about ±0.1; or about ±0.05. In embodiments, the crystalline form of Formula 1 exhibits an XRPD pattern comprising peaks at 10.0, 15.0, 16.3, and 21.3 °2θ with the margin of error of about ±0.2; about ±0.1; or about ±0.05. In embodiments, the crystalline form of Formula 1 exhibits an XRPD pattern further comprising peaks at 25.8 and 31.1 with the margin of error of about ±0.2; about ±0.1; or about ±0.05. In embodiments, the crystalline form of Formula 1 exhibits an XRPD pattern further comprising at least one peak at 25.1, 28.2, or 30.2 °2θ with the margin of error of about ±0.2; about ±0.1; or about ±0.05. In embodiments, the crystalline form of Formula 1 exhibits an XRPD pattern further comprising at least two peaks selected from 25.1, 28.2, or 30.2 °2θ with the margin of error of about ±0.2; about ±0.1; or about ±0.05. In embodiments, the crystalline form of Formula 1 exhibits an XRPD pattern further comprising peaks at 25.1, 28.2, and 30.2 °2θ with the margin of error of about ±0.2; about ±0.1; or about ±0.05.

In embodiments, the crystalline form of Formula 1 exhibits an XRPD pattern comprising peaks at 10.0±0.2, 15.0±0.2, and 16.3±0.2 °2θ. In embodiments, the crystalline form of Formula 1 exhibits an XRPD pattern comprising peaks at 10.0±0.2, 15.0±0.2, 16.3±0.2, and 21.3±0.2 °2θ. In embodiments, the crystalline form of Formula 1 exhibits an XRPD pattern comprising peaks at 25.8±0.2 and 31.1±0.2 °2θ. In embodiments, the crystalline form of Formula 1 exhibits an XRPD pattern further comprising at least one peak at 25.1±0.2, 28.2±0.2, or 30.2±0.2 °2θ. In embodiments, the crystalline form of Formula 1 exhibits an XRPD pattern further comprising at least two peaks selected from 25.1±0.2, 28.2±0.2, or 30.2±0.2 °2θ. In embodiments, the crystalline form of Formula 1 exhibits an XRPD pattern further comprising peaks at 25.1±0.2, 28.2±0.2, and 30.2±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 12.

In embodiments, the crystalline form of the compound of Formula 1 exhibits an XRPD comprising peaks shown in Table 12.

In embodiments, the crystalline form of the compound of Formula 1 exhibits an XRPD pattern comprising one or more peaks from Table 12 having intensity of at least 5%. In embodiments, the crystalline form of the compound of Formula 1 exhibits an XRPD pattern comprising one or more peaks from Table 12 having intensity of at least 10%. In embodiments, the crystalline form of the compound of Formula 1 exhibits an XRPD pattern comprising one or more peaks from Table 12 having intensity of at least 20%. In embodiments, the crystalline form of the compound of Formula 1 exhibits an XRPD pattern comprising one or more peaks from Table 12 having intensity of at least 25%. In embodiments, the crystalline form of the compound of Formula 1 exhibits an XRPD pattern comprising one or more peaks from Table 12 having intensity of at least 30%. In embodiments, the crystalline form of the compound of Formula 1 exhibits an XRPD pattern comprising one or more peaks from Table 12 having intensity of at least 35%. In embodiments, the crystalline form of the compound of Formula 1 exhibits an XRPD pattern comprising one or more peaks from Table 12 having intensity of at least 40%. In embodiments, the crystalline form of the compound of Formula 1 exhibits an XRPD pattern comprising one or more peaks from Table 12 having intensity of at least 45%. In embodiments, the crystalline form of the compound of Formula 1 exhibits an XRPD pattern comprising one or more peaks from Table 12 having intensity of at least 50%. In embodiments, the crystalline form of the compound of Formula 1 exhibits an XRPD pattern comprising one or more peaks from Table 12 having intensity of at least 60%. In embodiments, the crystalline form of the compound of Formula 1 exhibits an XRPD pattern comprising one or more peaks from Table 12 having intensity of at least 70%. In embodiments, the crystalline form of the compound of Formula 1 exhibits an XRPD pattern comprising one or more peaks from Table 12 having intensity of at least 80%. In embodiments, the crystalline form of the compound of Formula 1 exhibits an XRPD pattern comprising one or more peaks from Table 12 having intensity of at least 90%.

Figure 28A:
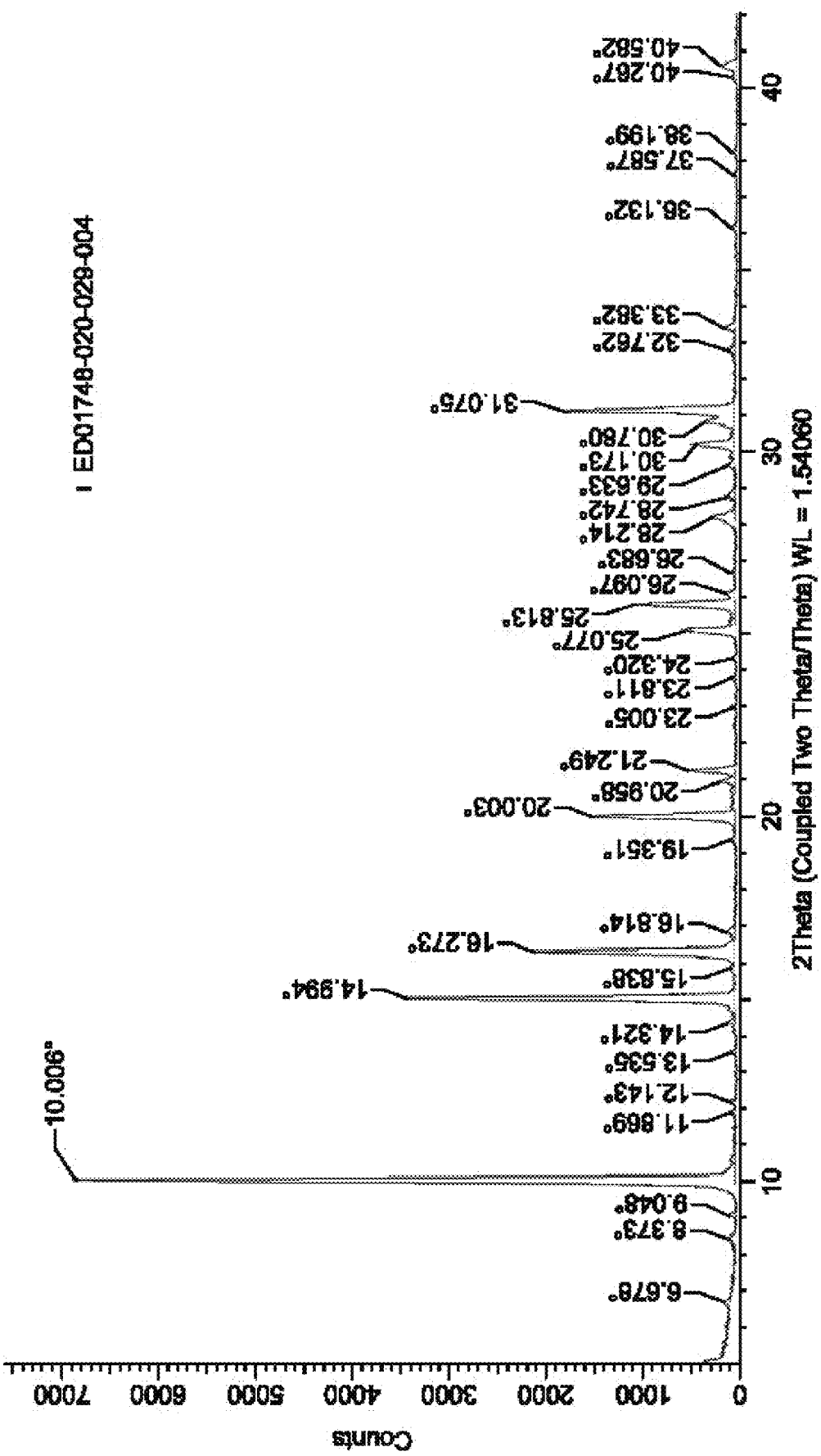
FIG. 28A shows an X-ray powder diffraction (XRPD) pattern of crystalline Pattern 7 of Formula 1.

In one specific embodiment, the crystalline form of Formula 1 exhibits an XRPD pattern that is substantially similar to FIG. 28A.

In some embodiments, the crystalline form of Formula 1 is at least about 90% Pattern 7 by weight. In some embodiments, the crystalline form of Formula 1 is at least about 95% Pattern 7 by weight. In some embodiments, the crystalline form of Formula 1 is at least about 95% Pattern 7 by weight. In some embodiments, the crystalline form of Formula 1 is at least about 99% Pattern 7 by weight. In some embodiments, the crystalline form of Formula 1 is at least about 90%, about 91%, about 92%, about 93%, about 94%, about 95%, about 96%, about 97%, about 98%, or about 99% Pattern 7 by weight.

In some embodiments, the crystalline form of Formula 1 is about 70% to about 100%, about 85.0% to 100%, or about 95.0% to 100% Pattern 7 by weight. In some embodiments, the crystalline form of Formula 1 is about 98.0% to 100% Pattern 7 by weight.

Crystalline Pattern 8 of Formula 1

In embodiments, the present disclosure provides a crystalline Pattern 8 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 8. In embodiments, the crystalline form of Formula 1 comprises greater than about 99%, 98%, 97%, 96%, 95%, 94%, 93%, 92%, 91%, or 90% of Pattern 8. In some embodiments, the crystalline form of Formula 1 comprises greater than about 90%, 85%, 80%, 75%, 70%, 65%, 60%, 55%, 50%, 45%, or 40% of Pattern 8.

In embodiments, the crystalline form of Formula 1 exhibits an XRPD pattern comprising peaks at 10.0, 15.0, and 16.2 °2θ, with the margin of error of about ±0.2; about ±0.1;

or about ±0.05. In embodiments, the crystalline form of Formula 1 exhibits an XRPD pattern further comprising peaks at 20.0 and 31.1 °2θ, with the margin of error of about ±0.2; about ±0.1; or about ±0.05. In embodiments, the crystalline form of Formula 1 exhibits an XRPD pattern further comprising at least one peak at 21.3, 25.1. 28.1, 30.2, or 31.1, with the margin of error of about ±0.2; about ±0.1; or about ±0.05. In embodiments, the crystalline form of Formula 1 exhibits an XRPD pattern further comprising at least two peaks selected from 21.3, 25.1. 28.1, 30.2, or 31.1, with the margin of error of about ±0.2; about ±0.1; or about ±0.05. In embodiments, the crystalline form of Formula 1 exhibits an XRPD pattern further comprising at least three peaks selected from 21.3, 25.1. 28.1, 30.2, or 31.1, with the margin of error of about ±0.2; about ±0.1; or about ±0.05. In embodiments, the crystalline form of Formula 1 exhibits an XRPD pattern further comprising at least four peaks selected from 21.3, 25.1. 28.1, 30.2, or 31.1 with the margin of error of about ±0.2; about ±0.1; or about ±0.05. In embodiments, the crystalline form of Formula 1 exhibits an XRPD pattern further comprising peaks selected at 21.3, 25.1. 28.1, 30.2, and 31.1, with the margin of error of about ±0.2; about ±0.1; or about ±0.05.

In embodiments, the crystalline form of Formula 1 exhibits an XRPD pattern comprising peaks at 10.0±0.2, 15.0±0.2, and 16.2±0.2 °2θ. In embodiments, the crystalline form of Formula 1 exhibits an XRPD pattern further comprising peaks at 20.0±0.2 and 31.1±0.2 °2θ. In embodiments, the crystalline form of Formula 1 exhibits an XRPD pattern further comprising at least one peak at 21.3±0.2, 25.1±0.2. 28.1±0.2, 30.2±0.2, or 31.1±0.2 °2θ. In embodiments, the crystalline form of Formula 1 exhibits an XRPD pattern further comprising at least two peaks selected from 21.3±0.2, 25.1±0.2. 28.1±0.2, 30.2±0.2, or 31.1±0.2 °2θ. In embodiments, the crystalline form of Formula 1 exhibits an XRPD pattern further comprising at least three peaks selected from 21.3±0.2, 25.1±0.2. 28.1±0.2, 30.2±0.2, or 31.1±0.2 °2θ. In embodiments, the crystalline form of Formula 1 exhibits an XRPD pattern further comprising at least four peaks selected from 21.3±0.2, 25.1±0.2. 28.1±0.2, 30.2±0.2, or 31.1±0.2 °2θ. In embodiments, the crystalline form of Formula 1 exhibits an XRPD pattern comprising peaks at 21.3±0.2, 25.1±0.2. 28.1±0.2, 30.2±0.2, or 31.1±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 13.

In embodiments, the crystalline form of the compound of Formula 1 exhibits an XRPD comprising peaks shown in Table 13.

In embodiments, the crystalline form of the compound of Formula 1 exhibits an XRPD pattern comprising one or more peaks from Table 13 having intensity of at least 5%. In embodiments, the crystalline form of the compound of Formula 1 exhibits an XRPD pattern comprising one or more peaks from Table 13 having intensity of at least 10%. In embodiments, the crystalline form of the compound of Formula 1 exhibits an XRPD pattern comprising one or more peaks from Table 13 having intensity of at least 20%. In embodiments, the crystalline form of the compound of Formula 1 exhibits an XRPD pattern comprising one or more peaks from Table 13 having intensity of at least 25%. In embodiments, the crystalline form of the compound of Formula 1 exhibits an XRPD pattern comprising one or more peaks from Table 13 having intensity of at least 30%. In embodiments, the crystalline form of the compound of Formula 1 exhibits an XRPD pattern comprising one or more peaks from Table 13 having intensity of at least 35%. In embodiments, the crystalline form of the compound of Formula 1 exhibits an XRPD pattern comprising one or more peaks from Table 13 having intensity of at least 40%. In embodiments, the crystalline form of the compound of Formula 1 exhibits an XRPD pattern comprising one or more peaks from Table 13 having intensity of at least 45%. In embodiments, the crystalline form of the compound of Formula 1 exhibits an XRPD pattern comprising one or more peaks from Table 13 having intensity of at least 50%. In embodiments, the crystalline form of the compound of Formula 1 exhibits an XRPD pattern comprising one or more peaks from Table 13 having intensity of at least 60%. In embodiments, the crystalline form of the compound of Formula 1 exhibits an XRPD pattern comprising one or more peaks from Table 13 having intensity of at least 70%. In embodiments, the crystalline form of the compound of Formula 1 exhibits an XRPD pattern comprising one or more peaks from Table 13 having intensity of at least 80%. In embodiments, the crystalline form of the compound of Formula 1 exhibits an XRPD pattern comprising one or more peaks from Table 13 having intensity of at least 90%.

Figure 29A:
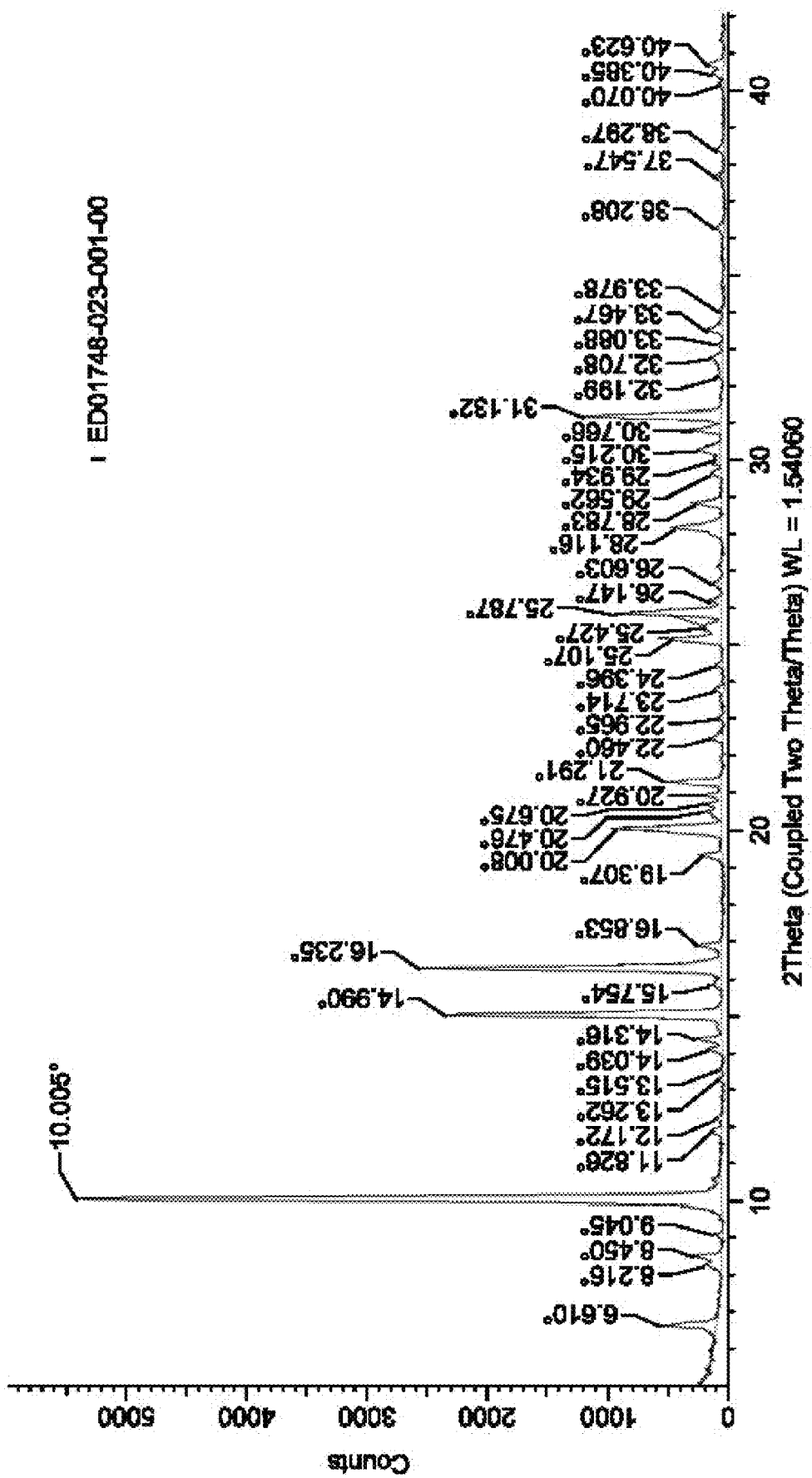
FIG. 29A shows an X-ray powder diffraction (XRPD) pattern of crystalline Pattern 8 of Formula 1.

In one specific embodiment, the crystalline form of Formula 1 exhibits an XRPD pattern that is substantially similar to FIG. 29A.

In some embodiments, the crystalline form of Formula 1 is at least about 90% Pattern 8 by weight. In some embodiments, the crystalline form of Formula 1 is at least about 95% Pattern 8 by weight. In some embodiments, the crystalline form of Formula 1 is at least about 95% Pattern 8 by weight. In some embodiments, the crystalline form of Formula 1 is at least about 99% Pattern 8 by weight. In some embodiments, the crystalline form of Formula 1 is at least about 90%, about 91%, about 92%, about 93%, about 94%, about 95%, about 96%, about 97%, about 98%, or about 99% Pattern 8 by weight.

In some embodiments, the crystalline form of Formula 1 is about 70% to about 100%, about 85.0% to 100%, or about 95.0% to 100% Pattern 8 by weight. In some embodiments, the crystalline form of Formula 1 is about 98.0% to 100% Pattern 8 by weight.

Crystalline Pattern 9 of Formula 1

In embodiments, the present disclosure provides a crystalline Pattern 9 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 9. In embodiments, the crystalline form of Formula 1 comprises greater than about 99%, 98%, 97%, 96%, 95%, 94%, 93%, 92%, 91%, or 90% of Pattern 9. In some embodiments, the crystalline form of Formula 1 comprises greater than about 90%, 85%, 80%, 75%, 70%, 65%, 60%, 55%, 50%, 45%, or 40% of Pattern 9.

In embodiments, the crystalline form of Formula 1 exhibits an XRPD pattern comprising peaks at 10.0, 16.4, and 25.9 °2θ with the margin of error of about ±0.2; about ±0.1; or about ±0.05. In embodiments, the crystalline form of Formula 1 exhibits an XRPD pattern further comprising peaks at 15.0 and 28.4 °2θ with the margin of error of about ±0.2; about ±0.1; or about ±0.05. In embodiments, the crystalline form of Formula 1 exhibits an XRPD pattern further comprising peaks at least one peak at 8.4, 12.0, 14.2, 20.0, 21.1, 25.1, or 30.9 °2θ with the margin of error of about ±0.2; about ±0.1; or about ±0.05. In embodiments, the crystalline form of Formula 1 exhibits an XRPD pattern further comprising peaks at least two peaks selected from 8.4, 12.0, 14.2, 20.0, 21.1, 25.1, or 30.9 °2θ with the margin of error of about ±0.2; about ±0.1; or about ±0.05. In embodiments, the crystalline form of Formula 1 exhibits an XRPD pattern further comprising peaks at least three peaks selected from 8.4, 12.0, 14.2, 20.0, 21.1, 25.1, or 30.9 °2θ with the margin of error of about ±0.2; about ±0.1; or about ±0.05. In embodiments, the crystalline form of Formula 1 exhibits an XRPD pattern further comprising peaks at least four peaks selected from 8.4, 12.0, 14.2, 20.0, 21.1, 25.1, or 30.9 °2θ with the margin of error of about ±0.2; about ±0.1; or about ±0.05. In embodiments, the crystalline form of Formula 1 exhibits an XRPD pattern further comprising peaks at least five peaks selected from 8.4, 12.0, 14.2, 20.0, 21.1, 25.1, or 30.9 °2θ with the margin of error of about ±0.2; about ±0.1; or about ±0.05. In embodiments, the crystalline form of Formula 1 exhibits an XRPD pattern further comprising peaks at least six peaks selected from 8.4, 12.0, 14.2, 20.0, 21.1, 25.1, or 30.9 °2θ with the margin of error of about ±0.2; about ±0.1; or about ±0.05. In embodiments, the crystalline form of Formula 1 exhibits an XRPD pattern further comprising peaks at 8.4, 12.0, 14.2, 20.0, 21.1, 25.1, and 30.9 °2θ with the margin of error of about ±0.2; about ±0.1; or about ±0.05.

In embodiments, the crystalline form of Formula 1 exhibits an XRPD pattern comprising peaks at 10.0±0.2, 16.4±0.2, and 25.9±0.2 °2θ. In embodiments, the crystalline form of Formula 1 exhibits an XRPD pattern comprising peaks at 15.0±0.2 and 28.4±0.2 °2θ. In embodiments, the crystalline form of Formula 1 exhibits an XRPD pattern comprising at least one peak at 8.4±0.2, 12.0±0.2, 14.2±0.2, 20.0±0.2, 21.1±0.2, 25.1±0.2, or 30.9±0.2 °2θ. In embodiments, the crystalline form of Formula 1 exhibits an XRPD pattern comprising at least two peaks selected from 8.4±0.2, 12.0±0.2, 14.2±0.2, 20.0±0.2, 21.1±0.2, 25.1±0.2, or 30.9±0.2 °2θ. In embodiments, the crystalline form of Formula 1 exhibits an XRPD pattern comprising at least three peaks selected from 8.4±0.2, 12.0±0.2, 14.2±0.2, 20.0±0.2, 21.1±0.2, 25.1±0.2, or 30.9±0.2 °2θ. In embodiments, the crystalline form of Formula 1 exhibits an XRPD pattern comprising at least four peaks selected from 8.4±0.2, 12.0±0.2, 14.2±0.2, 20.0±0.2, 21.1±0.2, 25.1±0.2, or 30.9±0.2 °2θ. In embodiments, the crystalline form of Formula 1 exhibits an XRPD pattern comprising at least five peaks selected from 8.4±0.2, 12.0±0.2, 14.2±0.2, 20.0±0.2, 21.1±0.2, 25.1±0.2, or 30.9±0.2 °2θ. In embodiments, the crystalline form of Formula 1 exhibits an XRPD pattern comprising at least six peaks selected from 8.4±0.2, 12.0±0.2, 14.2±0.2, 20.0±0.2, 21.1±0.2, 25.1±0.2, or 30.9±0.2 °2θ. In embodiments, the crystalline form of Formula 1 exhibits an XRPD pattern comprising peaks at 8.4±0.2, 12.0±0.2, 14.2±0.2, 20.0±0.2, 21.1±0.2, 25.1±0.2, and 30.9±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 14.

In embodiments, the crystalline form of the compound of Formula 1 exhibits an XRPD comprising peaks shown in Table 14.

In embodiments, the crystalline form of the compound of Formula 1 exhibits an XRPD pattern comprising one or more peaks from Table 14 having intensity of at least 5%. In embodiments, the crystalline form of the compound of Formula 1 exhibits an XRPD pattern comprising one or more peaks from Table 14 having intensity of at least 10%. In embodiments, the crystalline form of the compound of Formula 1 exhibits an XRPD pattern comprising one or more peaks from Table 14 having intensity of at least 20%. In embodiments, the crystalline form of the compound of Formula 1 exhibits an XRPD pattern comprising one or more peaks from Table 14 having intensity of at least 25%. In embodiments, the crystalline form of the compound of Formula 1 exhibits an XRPD pattern comprising one or more peaks from Table 14 having intensity of at least 30%. In embodiments, the crystalline form of the compound of Formula 1 exhibits an XRPD pattern comprising one or more peaks from Table 14 having intensity of at least 35%. In embodiments, the crystalline form of the compound of Formula 1 exhibits an XRPD pattern comprising one or more peaks from Table 14 having intensity of at least 40%. In embodiments, the crystalline form of the compound of Formula 1 exhibits an XRPD pattern comprising one or more peaks from Table 14 having intensity of at least 45%. In embodiments, the crystalline form of the compound of Formula 1 exhibits an XRPD pattern comprising one or more peaks from Table 14 having intensity of at least 50%. In embodiments, the crystalline form of the compound of Formula 1 exhibits an XRPD pattern comprising one or more peaks from Table 14 having intensity of at least 60%. In embodiments, the crystalline form of the compound of Formula 1 exhibits an XRPD pattern comprising one or more peaks from Table 14 having intensity of at least 70%. In embodiments, the crystalline form of the compound of Formula 1 exhibits an XRPD pattern comprising one or more peaks from Table 14 having intensity of at least 80%. In embodiments, the crystalline form of the compound of Formula 1 exhibits an XRPD pattern comprising one or more peaks from Table 14 having intensity of at least 90%.

Figure 30A:
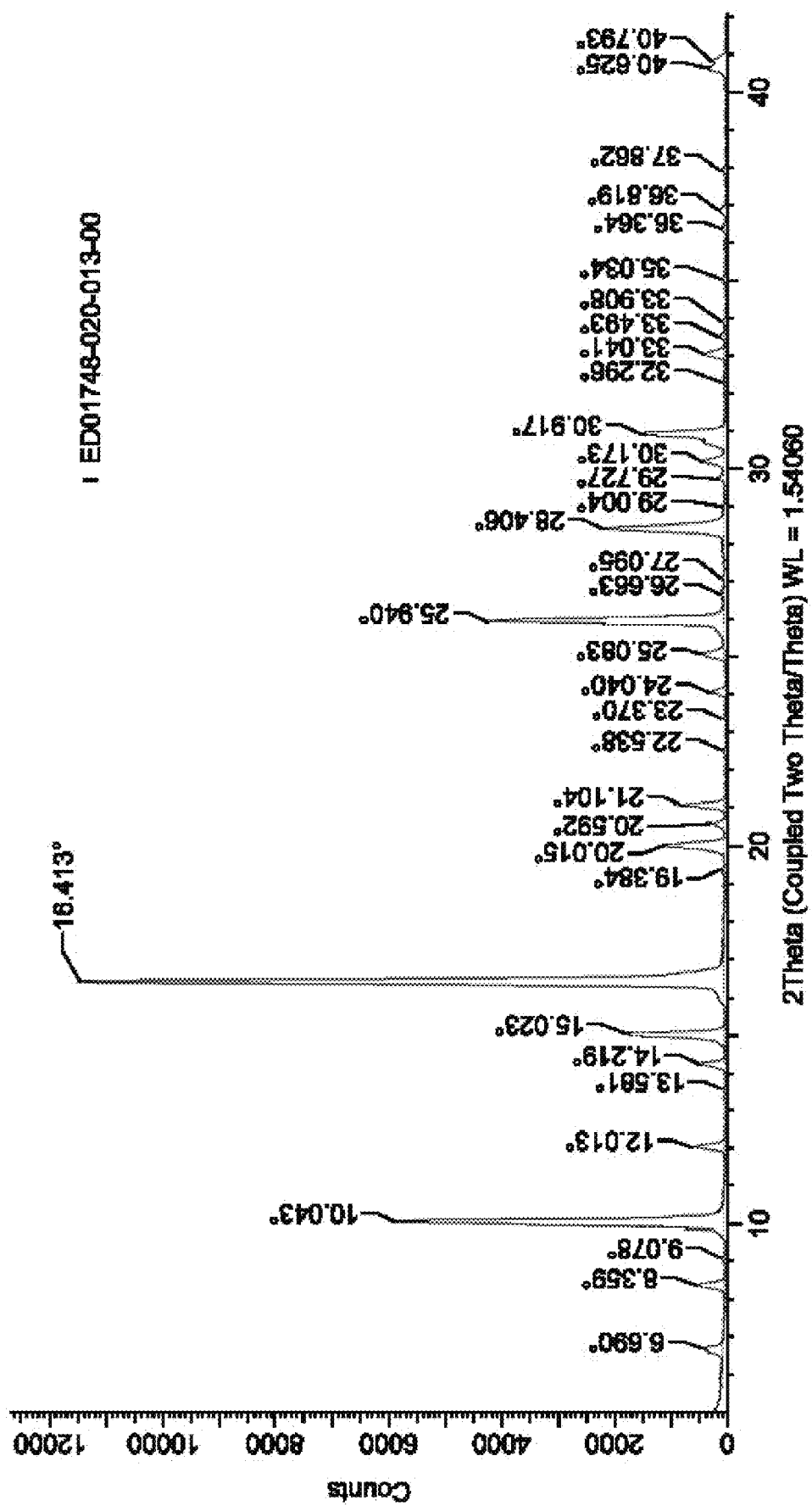
FIG. 30A shows an X-ray powder diffraction (XRPD) pattern of crystalline Pattern 9 of Formula 1.

In one specific embodiment, the crystalline form of Formula 1 exhibits an XRPD pattern that is substantially similar to the XRPD pattern of FIG. 30A.

In embodiments, the crystalline form of Formula 1 exhibits a differential scanning calorimetry (DSC) thermogram comprising endothermic peaks with an onset at about 63° C., about 81° C. and about 88° C.

Figure 30B:
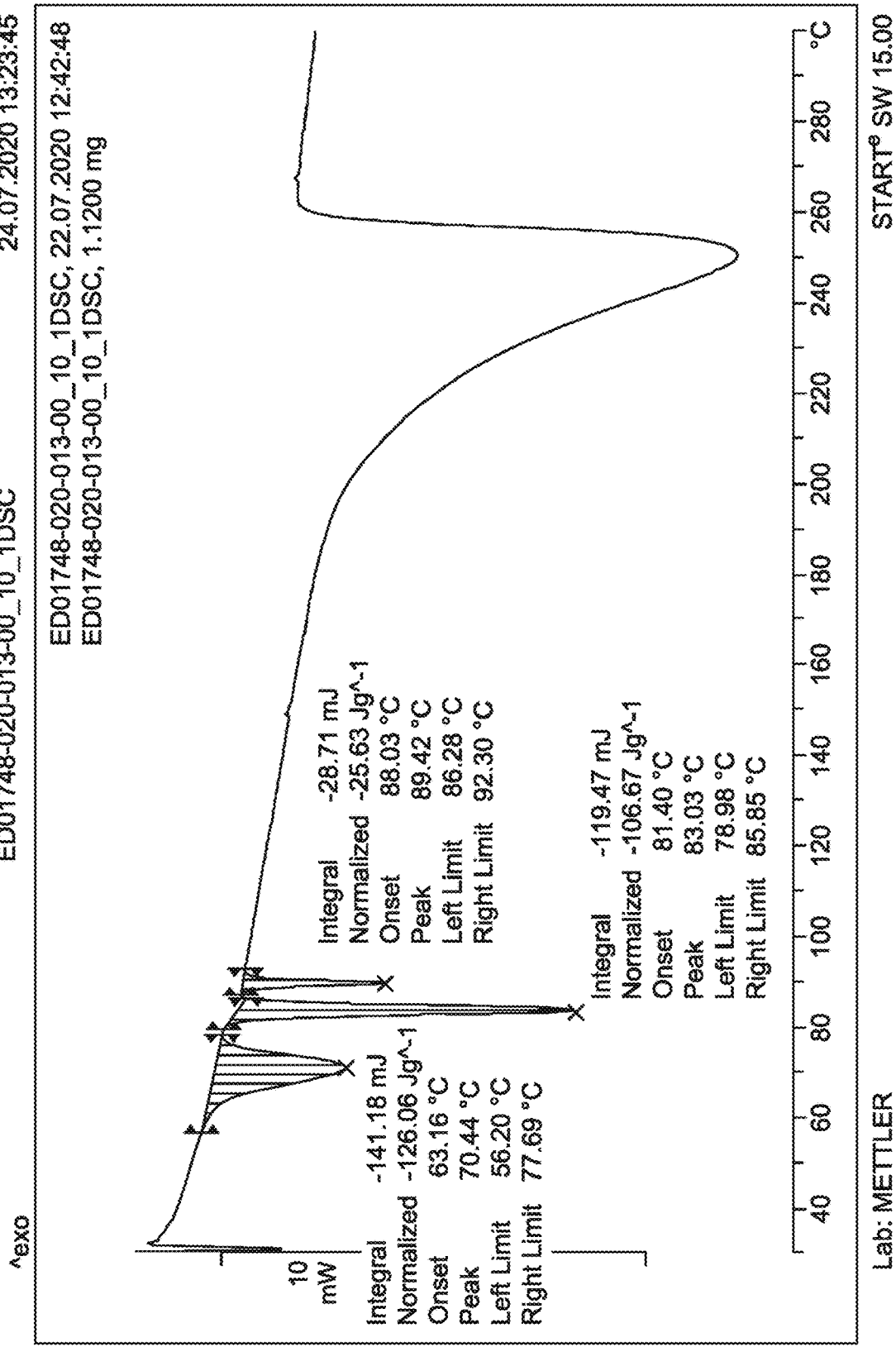
FIG. 30B shows a differential scanning calorimetry (DSC) thermogram of crystalline Form Pattern 9 of Formula 1.

In embodiments, the crystalline form of Formula 1 exhibits a DSC thermogram that is substantially similar to the DSC thermogram of FIG. 30B.

In some embodiments, the crystalline form of Formula 1 is at least about 90% Pattern 9 by weight. In some embodiments, the crystalline form of Formula 1 is at least about 95% Pattern 9 by weight. In some embodiments, the crystalline form of Formula 1 is at least about 95% Pattern 9 by weight. In some embodiments, the crystalline form of Formula 1 is at least about 99% Pattern 9 by weight. In some embodiments, the crystalline form of Formula 1 is at least about 90%, about 91%, about 92%, about 93%, about 94%, about 95%, about 96%, about 97%, about 98%, or about 99% Pattern 9 by weight.

In some embodiments, the crystalline form of Formula 1 is about 70% to about 100%, about 85.0% to 100%, or about 95.0% to 100% Pattern 9 by weight. In some embodiments, the crystalline form of Formula 1 is about 98.0% to 100% Pattern 9 by weight.

Crystalline Pattern 10 of Formula 1

In embodiments, the present disclosure provides a crystalline Pattern 10 of the compound of Formula 1.

In embodiments, the crystalline form of Formula 1 comprises greater than about 99.9%, about 99.8%, about 99.7%, about 99.6%, about 99.5%, about 99.4%, about 99.3%, about 99.2%, about 99.1%, or about 99.0% of Pattern 10. In embodiments, the crystalline form of Formula 1 comprises greater than about 99%, 98%, 97%, 96%, 95%, 94%, 93%, 92%, 91%, or 90% of Pattern 10. In some embodiments, the crystalline form of Formula 1 comprises greater than about 90%, 85%, 80%, 75%, 70%, 65%, 60%, 55%, 50%, 45%, or 40% of Pattern 10.

In embodiments, the crystalline form of Formula 1 exhibits an XRPD pattern comprising peaks at 14.7, 16.6, 22.1, 24.7, and 26.9 °2θ with the margin of error of about ±0.2; about ±0.1; or about ±0.05. In embodiments, the crystalline form of Formula 1 exhibits an XRPD pattern further comprising peaks at 11.9 and 13.4 °2θ with the margin of error of about ±0.2; about ±0.1; or about ±0.05. In embodiments, the crystalline form of Formula 1 exhibits an XRPD pattern further comprising at least one peak at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least two peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least three peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least four peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least five peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least six peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least seven peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least eight peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising at least nine peaks at 12.6, 15.8, 18.5, 21.5, 22.6, 22.8, 24.5, 25.1, and 29.4, or 38.8 °2θ with the margin of error of about ±0.2; about ±0.1; or about ±0.05. In embodiments, the crystalline form of Formula 1 exhibits an XRPD pattern further comprising peaks at 12.6, 15.8, 18.5, 21.5, 22.6, 22.8, 24.5, 25.1, and 29.4, and 38.8 °2θ with the margin of error of about ±0.2; about ±0.1; or about ±0.05.

In embodiments, the crystalline form of Formula 1 exhibits an XRPD pattern comprising peaks at 14.7±0.2, 16.6±0.2, 22.1±0.2, 24.7±0.2, and 26.9±0.2 °2θ. In embodiments, the crystalline form of Formula 1 exhibits an XRPD pattern comprising peaks at 11.9±0.2 and 13.4±0.2 °2θ. In embodiments, the crystalline form of Formula 1 exhibits an XRPD pattern comprising at least one peak at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least two peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least three peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least four peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least five peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least six peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least seven peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least eight peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising at least nine peaks at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ. In embodiments, the crystalline form of Formula 1 exhibits an XRPD pattern comprising peaks at 12.6±0.2, 15.8±0.2, 18.5±0.2, 21.5±0.2, 22.6±0.2, 22.8±0.2, 24.5±0.2, 25.1±0.2, and 29.4±0.2, and 38.8±0.2 °2θ.

In embodiments, the crystalline form of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 15.

In embodiments, the crystalline form of the compound of Formula 1 exhibits an XRPD comprising peaks shown in Table 15.

In embodiments, the crystalline form of the compound of Formula 1 exhibits an XRPD pattern comprising one or more peaks from Table 15 having intensity of at least 5%. In embodiments, the crystalline form of the compound of Formula 1 exhibits an XRPD pattern comprising one or more peaks from Table 15 having intensity of at least 10%. In embodiments, the crystalline form of the compound of Formula 1 exhibits an XRPD pattern comprising one or more peaks from Table 15 having intensity of at least 20%. In embodiments, the crystalline form of the compound of Formula 1 exhibits an XRPD pattern comprising one or more peaks from Table 15 having intensity of at least 25%. In embodiments, the crystalline form of the compound of Formula 1 exhibits an XRPD pattern comprising one or more peaks from Table 15 having intensity of at least 30%. In embodiments, the crystalline form of the compound of Formula 1 exhibits an XRPD pattern comprising one or more peaks from Table 15 having intensity of at least 35%. In embodiments, the crystalline form of the compound of Formula 1 exhibits an XRPD pattern comprising one or more peaks from Table 15 having intensity of at least 40%. In embodiments, the crystalline form of the compound of Formula 1 exhibits an XRPD pattern comprising one or more peaks from Table 15 having intensity of at least 45%. In embodiments, the crystalline form of the compound of Formula 1 exhibits an XRPD pattern comprising one or more peaks from Table 15 having intensity of at least 50%. In embodiments, the crystalline form of the compound of Formula 1 exhibits an XRPD pattern comprising one or more peaks from Table 15 having intensity of at least 60%. In embodiments, the crystalline form of the compound of Formula 1 exhibits an XRPD pattern comprising one or more peaks from Table 15 having intensity of at least 70%. In embodiments, the crystalline form of the compound of Formula 1 exhibits an XRPD pattern comprising one or more peaks from Table 15 having intensity of at least 80%. In embodiments, the crystalline form of the compound of Formula 1 exhibits an XRPD pattern comprising one or more peaks from Table 15 having intensity of at least 90%.

Figure 31A:
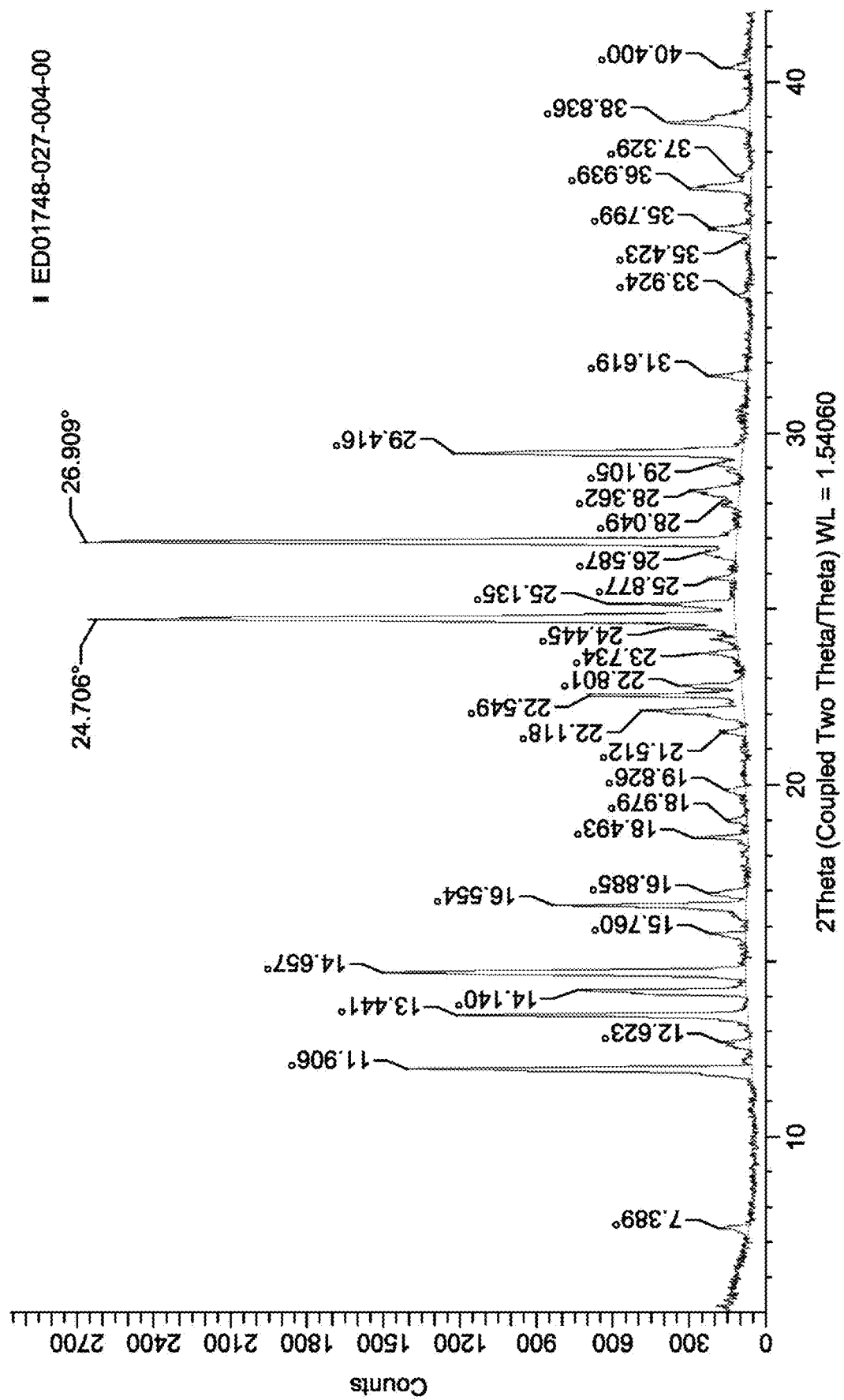
FIG. 31A shows an X-ray powder diffraction (XRPD) pattern of crystalline form Pattern 10 of Formula 1.

In one specific embodiment, the crystalline form of Formula 1 exhibits an XRPD pattern that is substantially similar to the XRPD pattern of FIG. 31A.

In some embodiments, the crystalline form of Formula 1 is at least about 90% Pattern 10 by weight. In some embodiments, the crystalline form of Formula 1 is at least about 95% Pattern 10 by weight. In some embodiments, the crystalline form of Formula 1 is at least about 95% Pattern 10 by weight. In some embodiments, the crystalline form of Formula 1 is at least about 99% Pattern 10 by weight. In some embodiments, the crystalline form of Formula 1 is at least about 90%, about 91%, about 92%, about 93%, about 94%, about 95%, about 96%, about 97%, about 98%, or about 99% Pattern 10 by weight.

In some embodiments, the crystalline form of Formula 1 is about 70% to about 100%, about 85.0% to 100%, or about 95.0% to 100% Pattern 10 by weight. In some embodiments, the crystalline form of Formula 1 is about 98.0% to 100% Pattern 10 by weight.

Crystalline Pattern 11 of Formula 1

In embodiments, the present disclosure provides a crystalline Pattern 11 of the compound of Formula 1.

In embodiments, the crystalline form of Formula 11 comprises greater than about 99.9%, about 99.8%, about 99.7%, about 99.6%, about 99.5%, about 99.4%, about 99.3%, about 99.2%, about 99.1%, or about 99.0% of Pattern 11. In embodiments, the crystalline form of Formula 1 comprises greater than about 99%, 98%, 97%, 96%, 95%, 94%, 93%, 92%, 91%, or 90% of Pattern 11. In some embodiments, the crystalline form of Formula 1 comprises greater than about 90%, 85%, 80%, 75%, 70%, 65%, 60%, 55%, 50%, 45%, or 40% of Pattern 11.

In embodiments, the crystalline form of Formula 1 exhibits an XRPD pattern comprising peaks at 10.0, 14.3, 16.3, 19.9 and 20.1 °2θ with the margin of error of about ±0.2; about ±0.1; or about ±0.05. In embodiments, the crystalline form of Formula 1 exhibits an XRPD pattern further comprising peaks at 27.9 and 28.2 °2θ with the margin of error of about ±0.2; about ±0.1; or about ±0.05. In embodiments, the crystalline form of Formula 1 exhibits an XRPD pattern further comprising at least one peak at 6.6, 8.2, 8.4, 14.3, 21.4, or 25.9 °2θ with the margin of error of about ±0.2; about ±0.1; or about ±0.05. In embodiments, the crystalline form of Formula 1 exhibits an XRPD pattern further comprising at least two peaks at 6.6, 8.2, 8.4, 14.3, 21.4, or 25.9 °2θ with the margin of error of about ±0.2; about ±0.1; or about ±0.05. In embodiments, the crystalline form of Formula 1 exhibits an XRPD pattern further comprising at least three peaks at 6.6, 8.2, 8.4, 14.3, 21.4, or 25.9 °2θ with the margin of error of about ±0.2; about ±0.1; or about ±0.05. In embodiments, the crystalline form of Formula 1 exhibits an XRPD pattern further comprising at least four peaks at 6.6, 8.2, 8.4, 14.3, 21.4, or 25.9 °2θ with the margin of error of about ±0.2; about ±0.1; or about ±0.05. In embodiments, the crystalline form of Formula 1 exhibits an XRPD pattern further comprising at least five peaks at 6.6, 8.2, 8.4, 14.3, 21.4, or 25.9 °2θ with the margin of error of about ±0.2; about ±0.1; or about ±0.05. In embodiments, the crystalline form of Formula 1 exhibits an XRPD pattern further comprising peaks at 6.6, 8.2, 8.4, 14.3, 21.4, and 25.9 °2θ with the margin of error of about ±0.2; about ±0.1; or about ±0.05.

In embodiments, the crystalline form of the compound of Formula 1 exhibits an XRPD pattern comprising peaks at 10.0±0.2, 14.3±0.2, 16.3±0.2, 19.9±0.2 and 20.1±0.2 °2Θ. In embodiments, the crystalline form of the compound of Formula 1 exhibits an XRPD pattern comprising peaks at 27.9±0.2 and 28.2±0.2 °2θ. In embodiments, the crystalline form of the compound of Formula 1 exhibits an XRPD pattern comprising at least one peak at 6.6±0.2, 8.2±0.2, 8.4±0.2, 14.3±0.2, 21.4±0.2, or 25.9±0.2 °2θ. In embodiments, the crystalline form of the compound of Formula 1 exhibits an XRPD pattern comprising at least two peaks at 6.6±0.2, 8.2±0.2, 8.4±0.2, 14.3±0.2, 21.4±0.2, or 25.9±0.2 °2θ. In embodiments, the crystalline form of the compound of Formula 1 exhibits an XRPD pattern comprising at least three peaks at 6.6±0.2, 8.2±0.2, 8.4±0.2, 14.3±0.2, 21.4±0.2, or 25.9±0.2 °2θ. In embodiments, the crystalline form of the compound of Formula 1 exhibits an XRPD pattern comprising at least four peaks at 6.6±0.2, 8.2±0.2, 8.4±0.2, 14.3±0.2, 21.4±0.2, or 25.9±0.2 °2θ. In embodiments, the crystalline form of the compound of Formula 1 exhibits an XRPD pattern comprising at least five peaks at 6.6±0.2, 8.2±0.2, 8.4±0.2, 14.3±0.2, 21.4±0.2, or 25.9±0.2 °2θ. In embodiments, the crystalline form of the compound of Formula 1 exhibits an XRPD pattern comprising peaks at 6.6±0.2, 8.2±0.2, 8.4±0.2, 14.3±0.2, 21.4±0.2, and 25.9±0.2 °2θ.

In some embodiments, the crystalline form of the compound of Formula 1 exhibits an XRPD pattern comprising 1 peak, 2 peaks, 3 peaks, 4 peaks, 5 peaks, 6 peaks, 7 peaks, 8 peaks, 9 peaks, or 10 peaks of Table 16.

In embodiments, the crystalline form of the compound of Formula 1 exhibits an XRPD comprising peaks shown in Table 16.

In embodiments, the crystalline form of the compound of Formula 1 exhibits an XRPD pattern comprising one or more peaks from Table 16 having intensity of at least 5%. In embodiments, the crystalline form of the compound of Formula 1 exhibits an XRPD pattern comprising one or more peaks from Table 16 having intensity of at least 10%. In embodiments, the crystalline form of the compound of Formula 1 exhibits an XRPD pattern comprising one or more peaks from Table 16 having intensity of at least 20%. In embodiments, the crystalline form of the compound of Formula 1 exhibits an XRPD pattern comprising one or more peaks from Table 16 having intensity of at least 25%. In embodiments, the crystalline form of the compound of Formula 1 exhibits an XRPD pattern comprising one or more peaks from Table 16 having intensity of at least 30%. In embodiments, the crystalline form of the compound of Formula 1 exhibits an XRPD pattern comprising one or more peaks from Table 16 having intensity of at least 35%. In embodiments, the crystalline form of the compound of Formula 1 exhibits an XRPD pattern comprising one or more peaks from Table 16 having intensity of at least 40%. In embodiments, the crystalline form of the compound of Formula 1 exhibits an XRPD pattern comprising one or more peaks from Table 16 having intensity of at least 45%. In embodiments, the crystalline form of the compound of Formula 1 exhibits an XRPD pattern comprising one or more peaks from Table 16 having intensity of at least 50%. In embodiments, the crystalline form of the compound of Formula 1 exhibits an XRPD pattern comprising one or more peaks from Table 16 having intensity of at least 60%.

In embodiments, the crystalline form of the compound of Formula 1 exhibits an XRPD pattern comprising one or more peaks from Table 16 having intensity of at least 70%. In embodiments, the crystalline form of the compound of Formula 1 exhibits an XRPD pattern comprising one or more peaks from Table 16 having intensity of at least 80%. In embodiments, the crystalline form of the compound of Formula 1 exhibits an XRPD pattern comprising one or more peaks from Table 16 having intensity of at least 90%.

Figure 32A:
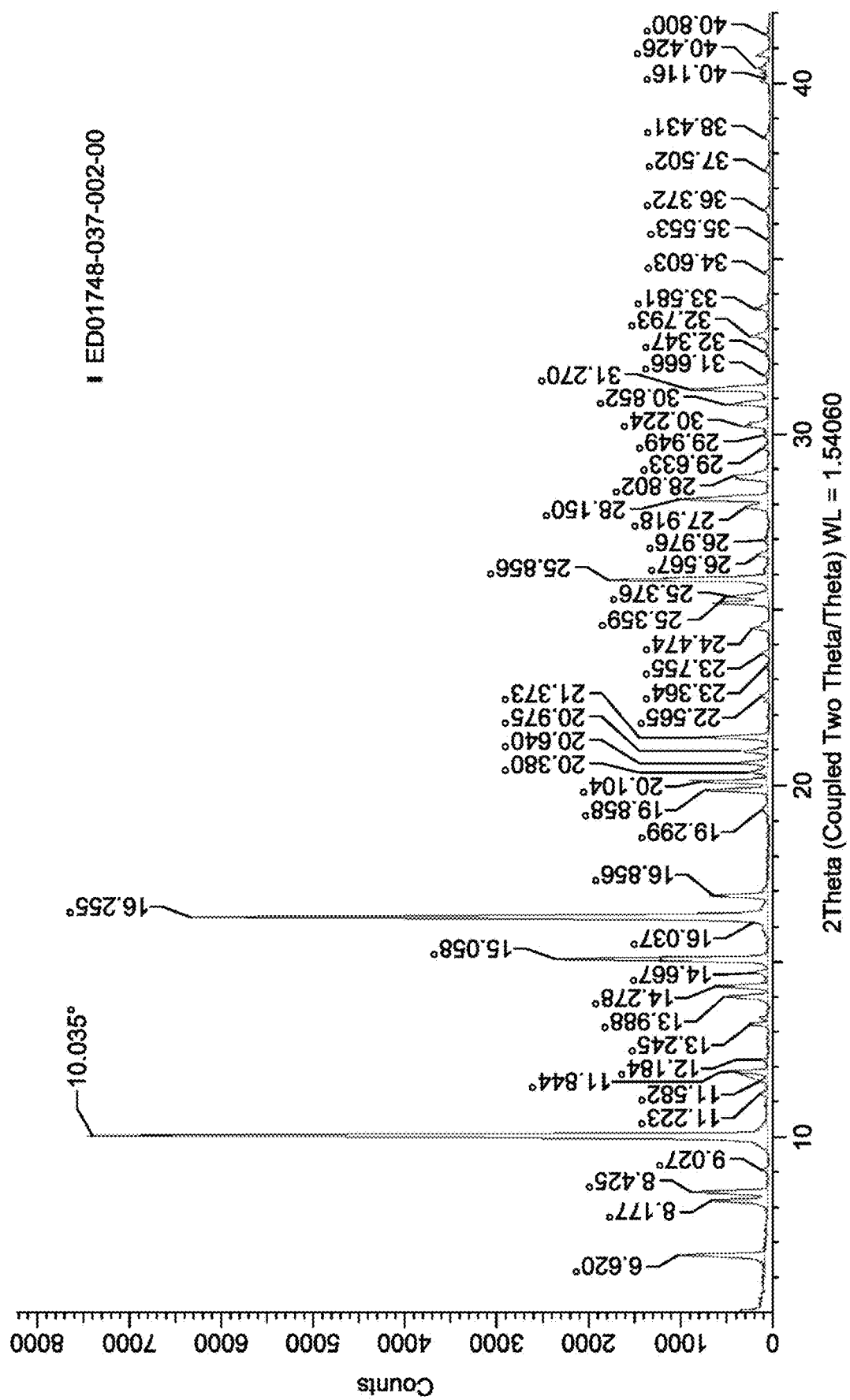
FIG. 32A shows an X-ray powder diffraction (XRPD) pattern of crystalline Pattern 11 of Formula 1.

In one specific embodiment, the crystalline form of Formula 1 exhibits an XRPD pattern that is substantially similar to the XRPD pattern of FIG. 32A.

In embodiments, the crystalline form of Formula 1 exhibits a differential scanning calorimetry (DSC) thermogram comprising endothermic peaks with an onset at about 70° C. and about 89° C.

In embodiments, the crystalline form of Formula 1 exhibits an about 3% (wt %) loss between about 73° C. to about 112° C. as determined by thermogravimetric analysis (TGA).

Figure 32B:
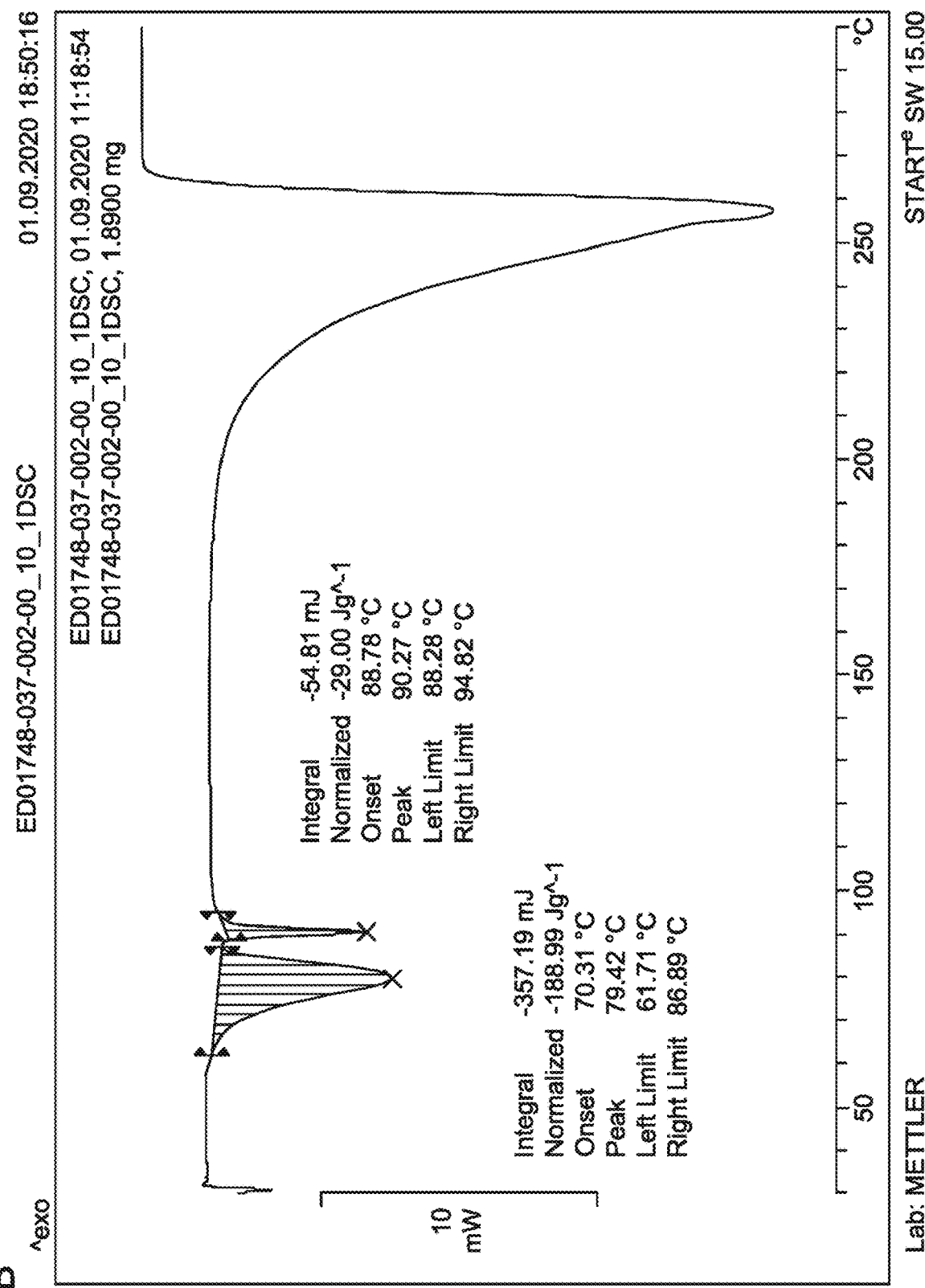
FIG. 32B shows a differential scanning calorimetry (DSC) thermogram of crystalline Pattern 11 of Formula 1.
Figure 32C:
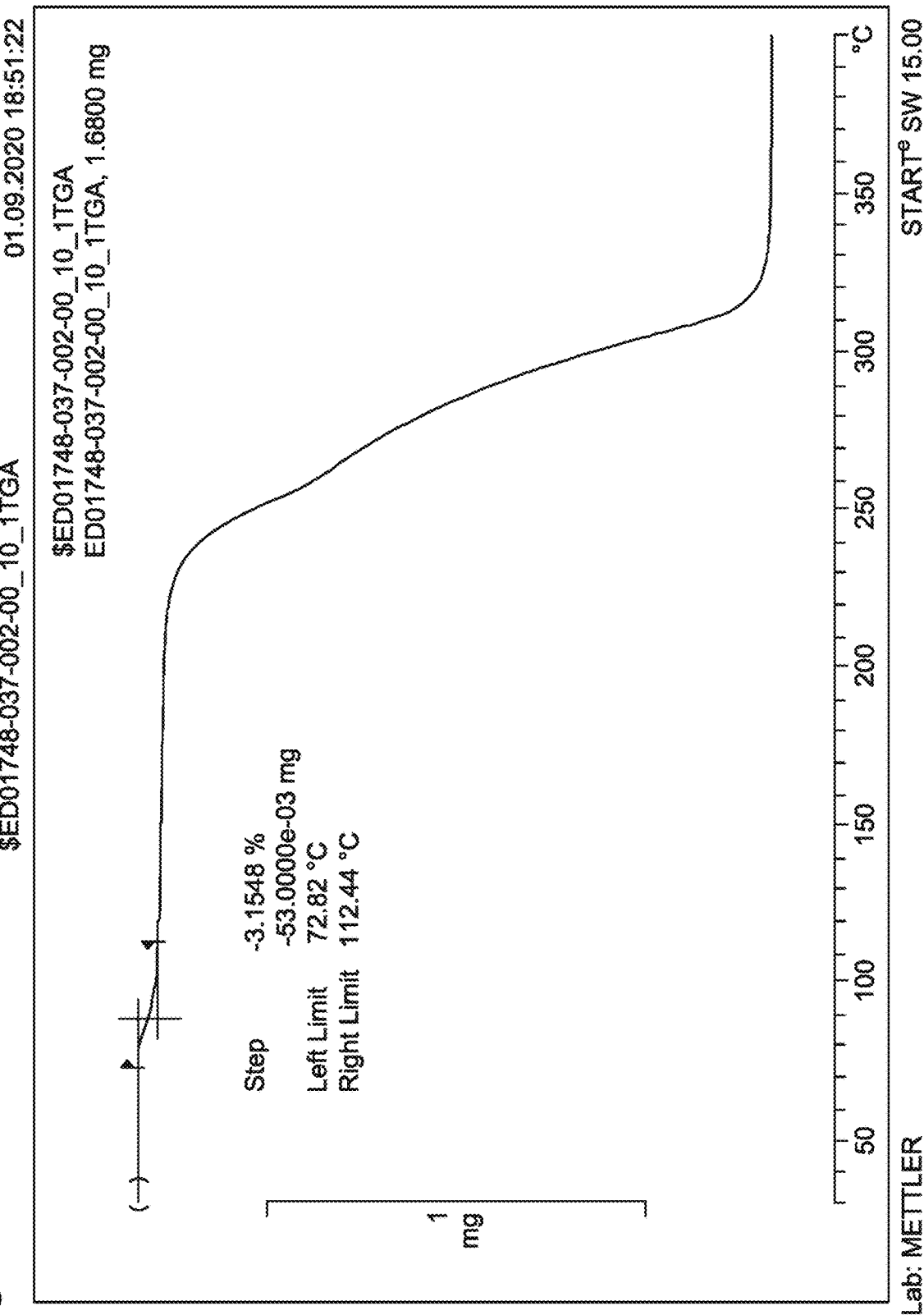
FIG. 32C shows a thermogravimetric analysis (TGA) thermogram of crystalline Pattern 11 of Formula 1.

In embodiments, the crystalline form of Formula 1 exhibits:
  a) a DSC thermogram that is substantially similar to the DSC thermogram of FIG. 32B; or
  b) a TGA thermogram that is substantially similar to the TGA thermogram of FIG. 32C.

In some embodiments, the crystalline form of Formula 1 is at least about 90% Pattern 11 by weight. In some embodiments, the crystalline form of Formula 1 is at least about 95% Pattern 11 by weight. In some embodiments, the crystalline form of Formula 1 is at least about 95% Pattern 11 by weight. In some embodiments, the crystalline form of Formula 1 is at least about 99% Pattern 11 by weight. In some embodiments, the crystalline form of Formula 1 is at least about 90%, about 91%, about 92%, about 93%, about 94%, about 95%, about 96%, about 97%, about 98%, or about 99% Pattern 11 by weight.

In some embodiments, the crystalline form of Formula 1 is about 70% to about 100%, about 85.0% to 100%, or about 95.0% to 100% Pattern 11 by weight. In some embodiments, the crystalline form of Formula 1 is about 98.0% to 100% Pattern 11 by weight.

In embodiments of the present invention, the crystalline form of (1-(2-chlorophenyl)-(S)-1-hydroxypropyl-(S)-2-carbamate) was dissolved in one or more solvents selected from 1,4-dioxane, t-butanol, dichloromethane and/or water, or maintained for a predetermined time after dissolution, thereby obtaining an amorphous product. Afterward, the resulting product was crystallized by polymorphic screening using a solvent, thereby obtaining polymorphic patterns.

As a solvent used in the polymorphic screening, a solvent selected from the group consisting of diethyl ether, pentane, ethyl formate, tert-butylmethyl ether, acetone, methyl acetate, chloroform, methanol, tetrahydrofuran, diisopropyl ether, ethyl acetate, ethanol, methyl ethyl ketone, acetonitrile, 2-propanol, tert-butanol, 1,2-dimethoxyethane, isopropyl acetate, 1-propanol, 2-butanol, heptane, water, formic acid, 1,4-dioxane, propyl acetate, 2-pentanone, 2-methyl-1-propanol, toluene, isobutyl acetate, methyl isobutyl ketone, 1-butanol, acetic acid, 2-methoxyethanol, butyl acetate, methyl butyl ketone, 3-methyl-1-butanol, 2-ethoxyethanol, 1-pentanol, cumene, anisole, benzonitrile, dimethyl sulfoxide and benzyl alcohol, and a mixed solvent thereof was used, and more preferably, a solvent for screening the Pattern 1 crystalline form, such as a solvent selected from the group consisting of acetone, chloroform, MeOH, tetrahydrofuran, diisopropyl ether, ethanol (EtOH), methyl ethyl ketone, acetonitrile, 2-propanol, tert-butanol), 1,2-dimethoxyethane (DME), 1-propanol, 2-butanol, water, 1,4-dioxane, 2-methyl-1-propanol, 2-methoxyethanol, butyl acetate, methyl butyl ketone, 3-methyl-1-butanol, 1-pentanol, cumene and anisole, and a mixed solvent thereof was used.

In another aspect of the present invention, the present invention provides a pharmaceutical composition including the crystalline form of 1-(2-chlorophenyl)-(S)-1-hydroxypropyl-(S)-2-carbamate (JBPOS0101).

The pharmaceutical composition may be used as a pharmaceutical composition for a similar use to that of phenyl carbamate or a derivative thereof, and more specifically, a composition for treating or preventing one or more diseases selected from the group consisting of muscle relaxation, spasticity, spasms, central nervous system disorders, Lou Gehrig's disease, multiple sclerosis, pain, stroke, epilepsy, epilepsy-related syndrome, pediatric epilepsy, pediatric epilepsy-related syndrome, memory loss-related disease, nerve gas-induced disease, psychiatric disorder, movement disorder and neurological injury disease.

More specifically, wherein the memory loss-related disease comprising senile dementia or Alzheimer's disease; wherein the nerve gas-induced disease comprising spasm, gastrointestinal distress, emesis, rhinorrhea, miosis, bronchoconstriction, fasciculation, floppy paralysis, apnea, diaphoresis and diarrhea; wherein the psychiatric disorder comprising depressive, bipolar disorders, anxiety disorder and seizures; wherein the movement disorder comprising ataxia, corticobasal ganglionic degeneration (CBGD), dyskinesia, dystonia, tremors, essential tremor, Parkinsonian tremor, hereditary spastic paraplegia, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), hemibalismus, hemi-facial spasm, Wilson's disease, stiff man syndrome, akinetic mutism, psychomotor retardation, painful legs moving toes syndrome, a gait disorder, and a drug-induced movement disorder; wherein the neurological injury disease comprising neurodegenerative disease, autism spectrum disease and prion diseases; wherein the neurodegenerative disease is selected from the group consisting of Huntington's disease, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease, spinocerebellar ataxia, olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy and familial dysautonomia; wherein the autism spectrum disease is selected from the group consisting of autism, Asperger syndrome and pervasive developmental disorder not otherwise specified (PDD-NOS); and wherein the prion diseases is selected from the group consisting of Creutzfeldt-Jakob disease, Gerstmann-Straussler-Scheinker disease, Kuru disease and fatal familial insomnia.

In addition, the pharmaceutical composition of the present invention may be formulated in various oral dosage forms or parenteral dosage forms. For example, the pharmaceutical composition may be prepared in any formulation for oral administration such as tablets, pills, soft/hard capsules, liquids, suspensions, emulsions, syrups, granules, and elixirs. The oral formulation may include a pharmaceutically available carrier such as a diluent such as lactose, dextrose, sucrose, mannitol, sorbitol, cellulose and/or glycine, or a glidant such as silica, talc, stearic acid and a magnesium or calcium salt thereof and/or polyethylene glycol, in addition to the active ingredient, according to a conventional composition of each formulation.

In addition, when the oral formulation is a tablet, it may include a binder such as magnesium aluminum silicate, starch paste, gelatin, tragacanth, methyl cellulose, sodium carboxymethylcellulose and/or polyvinylpyrrolidine, and in some cases, it may also include a disintegrant such as starch, agar, alginic acid or a sodium salt thereof or a boiling mixture, and/or an absorbent, a colorant, a flavoring agent or a sweetening agent.

In addition, the pharmaceutical composition may be formulated in a parenteral dosage form, and administered by a parenteral administration method such as subcutaneous injection, intravenous injection, intramuscular injection or intrathoracic injection. Here, to prepare the parenteral formulations, the pharmaceutical composition may be prepared in a solution or suspension by mixing an active ingredient with a stabilizing agent or buffer in water, and the solution or suspension may be dispensed into a unit dosage form of an ampoule or vial.

In addition, the pharmaceutical composition may be sterilized or further include additives such as a preservative, a stabilizing agent, a wetting agent or emulsifier, a salt for osmotic control and/or a buffer, and may further include other therapeutically useful materials. The pharmaceutical composition may be prepared by a conventional method such as mixing, granulation or coating.

In addition, the active ingredient may be administered daily at a therapeutically effective amount of 0.01 to 750 mg/kg (body weight), and preferably 0.1 to 500 mg/kg (body weight) for mammals including humans. Such a pharmaceutical composition may be administered once or in a two or more divided portions a day via oral or parenteral routes.

EXAMPLES

Hereinafter, the present invention will be described in detail with reference to examples to help in understanding the present invention. However, examples according to the present invention may be modified into a variety of different forms, and it should not be construed that the scope of the present invention is limited to the following examples. The examples of the present invention are provided to more completely explain the present invention to those of ordinary skill in the art.

Experimental Methods
X-Ray Powder Diffraction (XRPD)

XRPD patterns were detected by CuKα irradiation (30 kV, 10 mA) using a Bruker AXS D2 diffractometer. The analysis was performed using θ-θ geometry and a LynxEye detector at 5 to 42 °2θ with a step size of 0.024 °2θ at 0.1 sec/step.

The software used for data collection was DIFFRAC. SUITE, and the data was analyzed and presented using Diffrac Plus EVA v 16.0.0.0.

Samples were run at ambient conditions and prepared as flat specimens using powder received without grinding. About 1 to 2 mg of the sample was lightly pressed on a silicon wafer to obtain a flat surface.

Single Crystal X-Ray Diffraction (SCXRD)

SCXRD analysis was performed by Rbar3 Ltd.

Nuclear Magnetic Resonance Spectroscopy (NMR)

A solution phase $^1$H NMR spectrum was obtained using a 5-mm PABBO probe-installed Bruker AVIIIHD NMR spectrometer operated at 400.1326 MHz. Samples were prepared with d6-DMSO unless otherwise specified and referenced using TMS internal standards.

Differential Scanning Calorimetry (DSC)

DSC data was collected on a Mettler DSC 3+ equipped with a 34 position auto-sampler. The instrument was calibrated for energy and temperature using certified indium. Generally, 0.5 to 3 mg of each sample was heated from 30 to 300° C. at 10° C./min in a pinhole aluminum pan. A nitrogen purge was maintained over the sample at 50 mL/min. STARe v15.00 was used for instrument control and data processing.

Thermogravimetric Analysis (TGA)

TGA data were collected on a Mettler TGA 2 equipped with a 34 position auto-sampler. The instrument was calibrated for energy and temperature using certified isotherm and nickel. Generally, 0.5 to 30 mg of each sample was heated at from 30 to 400° C. at 10° C./min in a pinhole aluminum pan. A nitrogen purge was maintained over the sample at 50 mL/min. STARe v15.00 was used for instrument control and data processing.

Polarized Light Microscopy (PLM)

A digital video camera-equipped Nikon DLM polarization microscope was used to capture sample images. A small amount of sample was placed on a glass slide, mounted in an immersion oil, and covered with a glass slip for individually isolating particles as much as possible. The sample was observed with appropriate magnification and partial polarization, coupled to a λ additive color filter.

Particle Size Distribution (PSD) by Laser Diffraction

PSD was measured using a Sympatec HELOS/BF particle sizer equipped with a RODOS/ASPIROS dry dispenser operating at 2.5 Bar with a sled speed of 25 mm/s. R1 0.1/0.18 μm-35 μm and R3 0.5/0.9 μm-175 μm lenses were combined and used for observation. Unless specified otherwise, a trigger condition of 1 ms 0.2% Ch27 was used.

Gravimetric Vapor Sorption (GVS)

Sorption isotherms were obtained using an SMS DVS intrinsic water absorption analyzer controlled by SMS Analysis Suite software. A sample temperature was maintained at 25° C. throughout. Humidity was controlled by a mixed stream of dry and wet nitrogen with a total flow rate of 200 mL/min. The relative humidity was measured with a calibrated Rotronic probe (dynamic range: 1.0-100% RH) located near the sample. The weight change (mass relaxation) of the sample as a function of % RH was continuously monitored using a microbalance (accuracy±0.005 mg). 5 to 20 mg of the sample was stored in a prepared stainless steel mesh basket under atmospheric conditions.

Measurement of Thermodynamic Solubility by UPLC

A thermodynamic solubility in water was determined by providing a suitable concentration of compound prepared by suspending a sufficient compound in water or buffer according to estimated solubilities of the medium and the compound. Quantification was done by UPLC with reference to a standard calibration curve. A solubility was calculated with QuanLynx using a peak area determined by the integration of a peak found at the same retention time as the main peak in the standard injection.

HPLC (High Performance Liquid Chromatography) Method for Chemical Purity

HPLC Method Parameters for Chemical Purity Determinations

| Column: | Waters XBridge Phenyl 4.6 × 150 mm, 3.5 μm |
|---|---|
| Oven Temperature (° C.): | 40° C. |
| Sample Temperature (° C.): | 5° C. |
| Injection (μL): | 10 |
| Run Time (min): | 25 |
| Detection: | UV Diode array 212 nm |
| Wavelength, Bandwidth (nm): | |
| Mobile Phase A: | 0.1% phosphoric acid in purified water |
| Mobile Phase B: | 0.1% phosphoric acid in acetonirile |
| Diluent Solution: | 0.01% trifluoroacetic acid in acetonitrile |
| Needle Wash Solvent: | 50% acetonitrile in purified water |
| Flow Rate (mL/min): | 1.0 |

| Timetable | Time (min) | % Phase A | % Phase B |
|---|---|---|---|
| | 0.0 | 95 | 5 |
| | 17.0 | 30 | 70 |
| | 17.1 | 95 | 5 |
| | 25.0 | 95 | 5 |

Analytical Preparation
  a. Reagents: Acetonitrile (HPLC grade or equivalent), Water (HPLC grade or equivalent), Trifluoroacetic acid (HPLC grade or equivalent), Phosphoric acid, reference standard of JBPOS0101
  b. Apparatus: Volumetric flask, Micro Pipette, Balance Analytical Procedure
  a. Preparation of mobile phase:
    Mobile Phase A: Take 1 mL of phosphoric acid into the 1 L volumetric flask and marked as water
    Mobile Phase B: Take 1 mL of phosphoric acid into the 1 L volumetric flask and marked as acetonitrile
  b. Preparation of diluent solution: Take 0.1 mL of trifluoroacetic acid into the 1 L volumetric flask and marked as acetonitrile
  c. Preparation of standard solution: Precisely weigh 12.5 mg of reference standard of JBPOS0101 and transfer it into a 100 mL volumetric flask. Add diluent and dilute to volume.
  d. Preparation of sample solution: Precisely weigh 12.5 mg of sample and transfer it into a 100 mL volumetric flask. Add diluent and dilute to volume.

Example 1

Preparation of Amorphous 1-(2-chlorophenyl)-(S)-1-hydroxypropyl-(S)-2-carbamate 1-(2-chlorophenyl)-(S)-1-hydroxypropyl-(S)-2-carbamate (JBPOS0101/S-P-17001) was obtained from Bio-Pharm Solutions Co. Ltd. A method of preparing a phenyl carbamate compound, JBPOS0101, is described in Korean Patent No. 10-2014-0113918 A.

The CRL batch reference number for a crystalline form of 1-(2-chlorophenyl)-(S)-1-hydroxypropyl-(S)-2-carbamate is ED01748-006-001-00, and has characteristics of Table 1 below.

TABLE 1

| | |
|---|---|
| Bio-Pharm Solutions Co. Ltd. Batch reference | JBPOS0101/S-P-17001 |
| CRL batch reference | ED01748-006-001-00 |
| Appearance | White crystalline solid |
| Molecular formula | $C_{10}H_{12}ClNO_3$ |
| Molecular weight | 229.66 |
| $^1$H NMR | Consistent with structure |
| UPLC Purity[3] | 98.6% |
| XRPD | Crystalline by XRPD, assigned as Pattern 1 |
| DSC | DSC shows a very small endothermic event of onset 81° C. (peak 82° C.), followed by a sharp endothermic event of onset 89° C. (peak 90° C.) consistent with a melt. Broad peak of onset 229° C. - decomposition |
| TGA | TGA shows 95% of mass remaining at 237° C. with no significant mass loss until above ca. 200° C. 100% of mass was lost by 305° C. |
| PSD | D10    D50    D90<br>0.95 μm  4.51 μm  41.92 μm |
| Log D (shake flask at pH 5), Log P | Log $D_{pH\ 5}$ = 1.32, Log P = 1.32 |
| GVS | Shows a 0.14% mass increase over the second sorption cycle (0-90% RH) |
| XRPD post GVS (ED01748-006-002-00) | Shows no change in form by XRPD post GVS |
| XRPD post storage at 40° C./75% RH for 7 days (ED01748-006-003-00) | Shows no change in form by XRPD post storage at 40° C./75% RH for 7 days |
| UPLC purity post storage at 40° C./75% RH for 7 days (ED01748-006-003-00) | 97.4% |
| $^1$H NMR post storage at 40° C./75% RH for 7 days (ED01748-006-003-00) | Consistent with structure |
| XRPD post storage at RT/97% RH for 7 days (ED01748-006-004-00) | Shows no change in form by XRPD post storage at RT/97% RH for 7 days |
| UPLC purity post storage at RT/97% RH for 7 days (ED01748-006-004-00) | 97.7% |
| $^1$H NMR purity post storage at RT/97% RH for 7 days (ED01748-006-004-00) | Consistent with structure |

For screening of various polymorphisms of the material, first, the material was amorphized, and the resulting amorphous material was used as a material for polymorphic screening with various solvents.

<1-1> Preparation of Amorphous Form by 1,4-Dioxane

Figure 2:
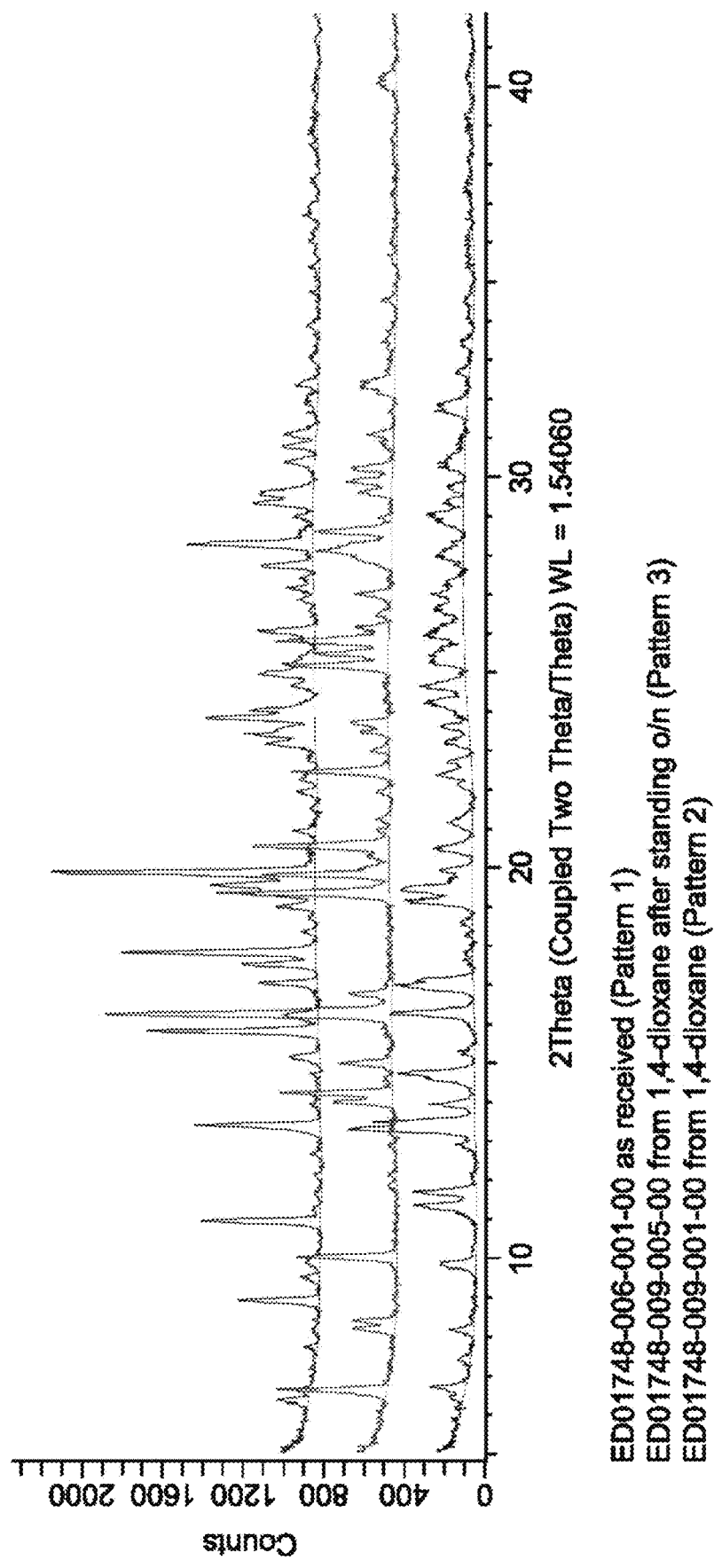
FIG. 2 shows the result of comparing XRPD patterns after 1,4-dioxane treatment (ED01748-009-001-00, Pattern 2) and storing overnight (ED01748-009-005-00, Pattern 3) to form amorphous 1-(2-chlorophenyl)-(S)-1-hydroxypropyl-(S)-2-carbamate (JBPOS0101).

A portion of ED01748-006-001-00 (15 mg) was dissolved in 1,4-dioxane (0.1 mL). A white solid ED01748-009-001-00 was prepared by flash freezing in a dry ice/acetone bath and freeze-drying the prepared solution, and as a result of XRPD analysis, a crystalline form (Pattern 2) with a different pattern was identified (FIG. 1). In addition, as a result of reanalysis of the ED01748-006-001-00 sample after being left overnight on the XRPD disc under laboratory conditions, a crystalline form with a novel pattern (ED01748-009-005-00, Pattern 3) was identified (FIG. 2).

<1-2> Preparation of Amorphous Form by 1,4-Dioxane/Water

ED01748-006-001-00 (10 mg) was dissolved in 1,4-dioxane (0.2 mL) and water (0.1 mL).

A white solid ED01748-013-001-00 was prepared by flash freezing in a dry ice/acetone bath and freeze-drying the prepared solution. As a result of XRPD analysis of the solution, a crystalline form with the same pattern as obtained by freeze-drying in 1,4-dioxane (Pattern 2) was identified.

<1-3> Preparation of Amorphous Form by t-Butanol

Figure 3:
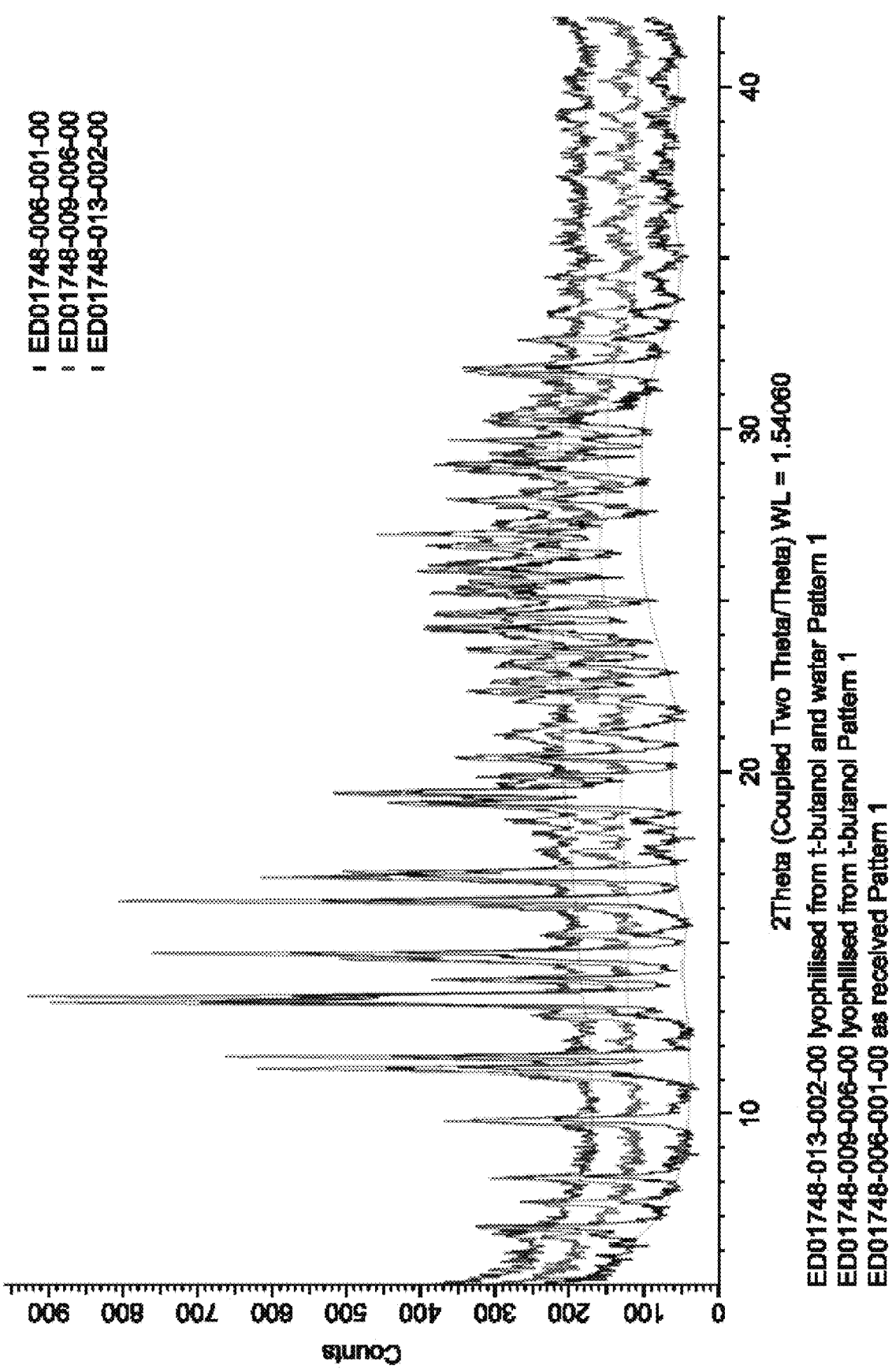
FIG. 3 shows the result of comparing XRPD patterns after t-butanol treatment (ED01748-009-006-00, Pattern 1), treatment of t-butanol with water (ED01748-013-002-00, Pattern 1) to form amorphous 1-(2-chlorophenyl)-(S)-1-hydroxypropyl-(S)-2-carbamate (JBPOS0101).

A portion of ED01748-006-001-00 (10 mg) was dissolved in t-butanol (0.25 mL). ED01748-009-006-00 with high viscosity was obtained by flash freezing in a dry ice/acetone bath and freeze-drying the prepared solution. According to the XRPD analysis of the material, the crystallinity of Pattern 1 was identified (FIG. 3).

<1-4> Preparation of Amorphous Form by t-Butanol/Water

A portion of ED01748-006-001-00 (10 mg) was dissolved in t-butanol (0.2 mL) and water (0.1 mL). A viscous material mixture (ED01748-013-002-00) was provided by flash freezing in a dry ice/acetone bath and freeze-drying the prepared solution. It was confirmed that the result of XRPD analysis corresponds to Pattern 1 (FIG. 3).

<1-5> Preparation of Amorphous Form by Evaporation of DCM Solution

Figure 4:
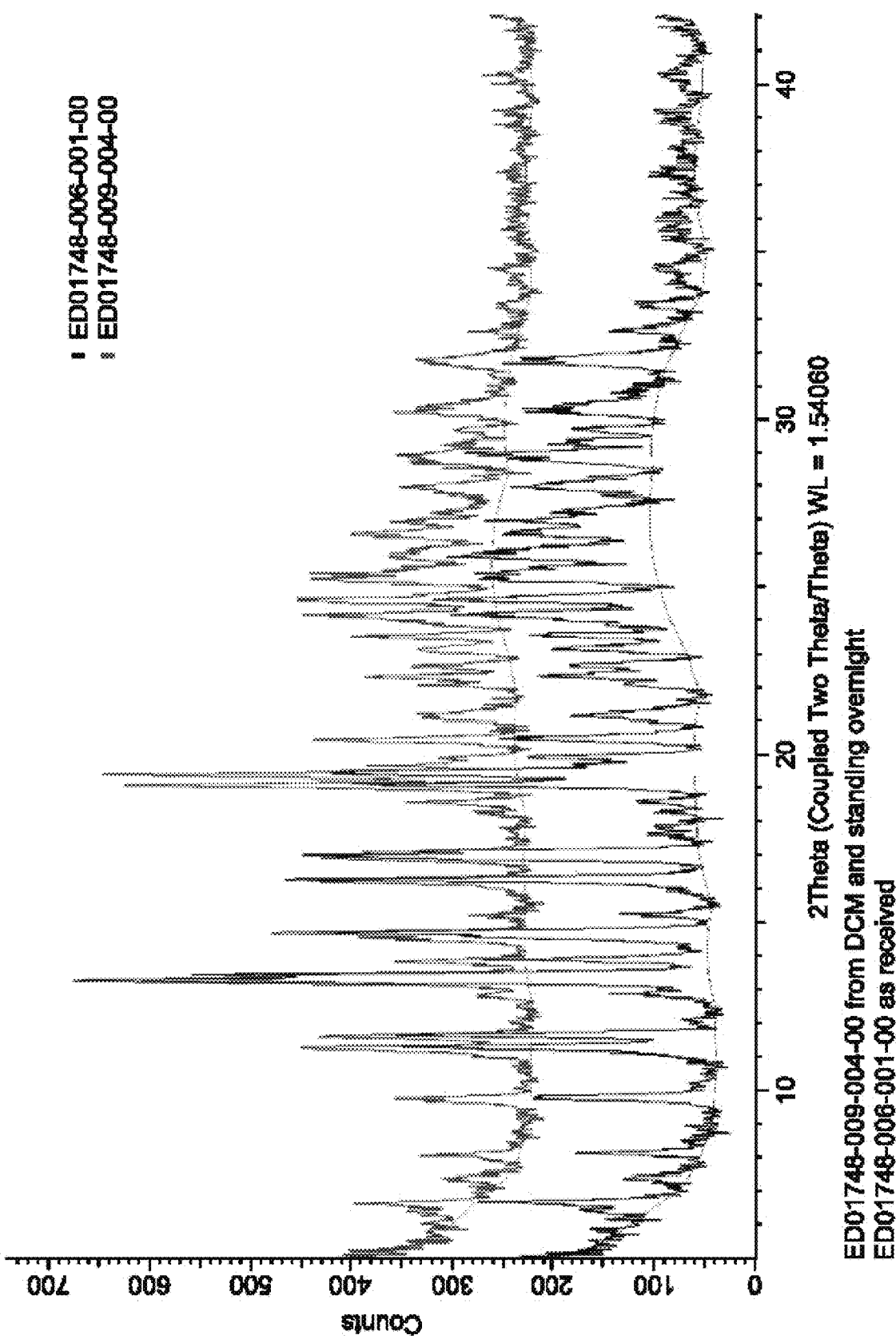
FIG. 4 shows the result of comparing XRPD patterns of a material (ED01748-013-002-00, Pattern 1) formed by treatment of a dichloromethane solution and evaporation of the solution to form amorphous 1-(2-chlorophenyl)-(S)-1-hydroxypropyl-(S)-2-carbamate (JBPOS0101).

A portion of ED01748-006-001-00 (20 mg) was dissolved in dichloromethane (DCM)(2 mL), and then the solution was rapidly evaporated under vacuum, thereby obtaining a colorless viscous material. After standing overnight, the total sample was solidified (ED01748-009-004-00), and it was confirmed that the XRPD analysis result corresponds to Pattern 1 (FIG. 4).

<1-6> DSC Experiment for Preparing Amorphous Material

To prepare and confirm an amorphous material, two types of DSC experiments (A/B) were performed on ED01748-006-001-00.

DSC A Experiment

Figure 5:
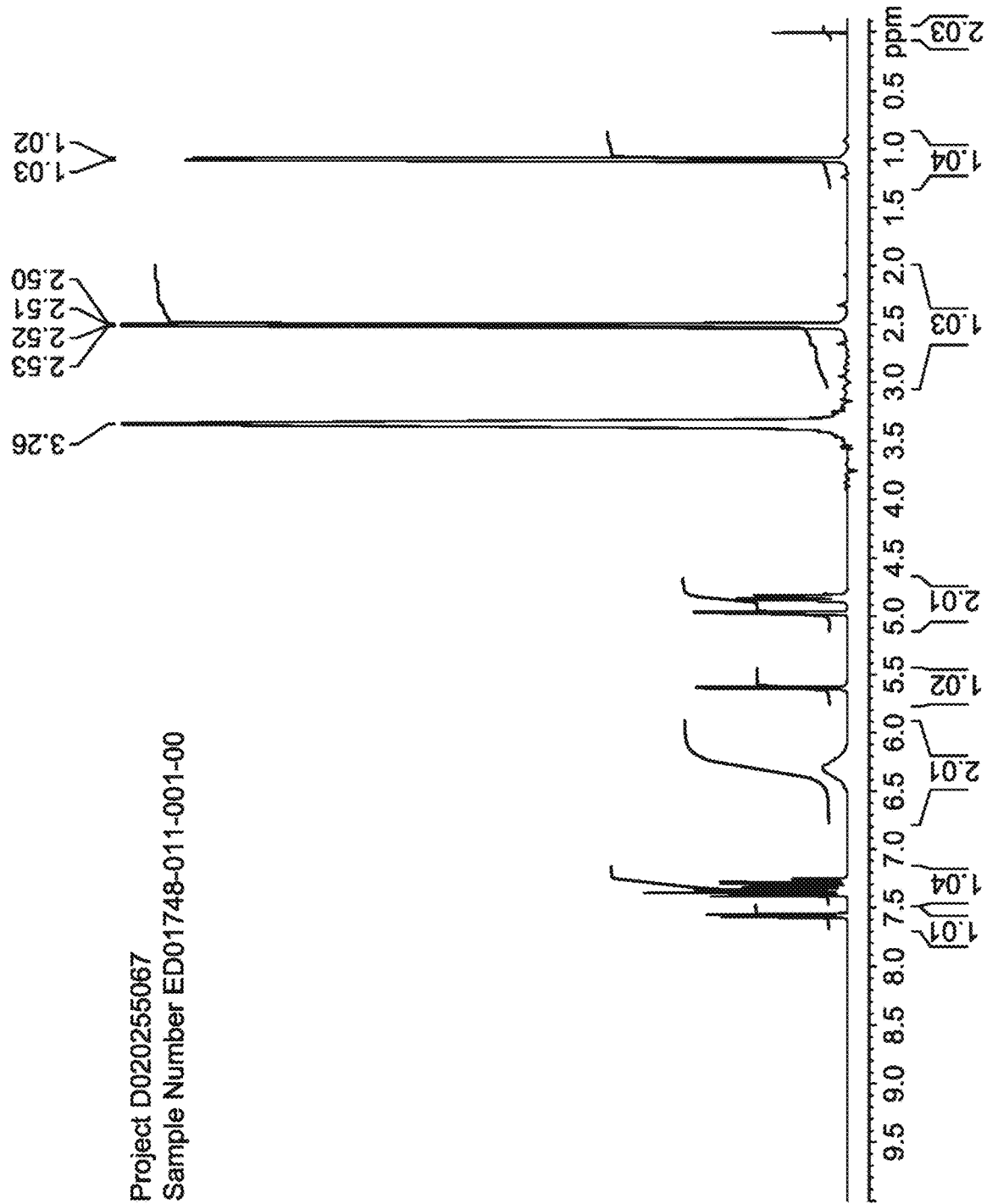
FIG. 5 shows the $^1$H NMR result for a crystal generated after two types of DSC A to prepare and confirm an amorphous material.

A portion of ED01748-006-001-00 was heated in a differential scanning calorimeter at 10° C./min to 110° C., and then cooled to 30° C. at 50° C./min. The contents of a DSC pan were analyzed by $^1$H NMR. As a result, after melting and cooling, no degradation or migration of the sample was observed (FIG. 5).

DSC B Experiment

A portion of ED01748-006-001-00 was heated in a differential scanning calorimeter at 10° C./min to 110° C., and then cooled to −30° C. at 10° C./min, followed by heating again to 300° C.

Finally, as the sample was heated, a glass transition temperature (Tg) was observed at 14.6° C. (median: 15.3° C.), and other thermal changes were not observed until the sample was decomposed at about 190° C. or more.

In both DSC experiments A and B, the sample was dissolved and then cooled, thereby generating an amorphous material, and there was no evidence of decomposition by NMR. Experiment B showed a low glass transition temperature (Tg onset: 14.6° C.) of the material, indicating that the stability of the amorphous material may be an issue.

<1-7> Preparation of Amorphous Form by Melting and Rapid Cooling

Figure 6:
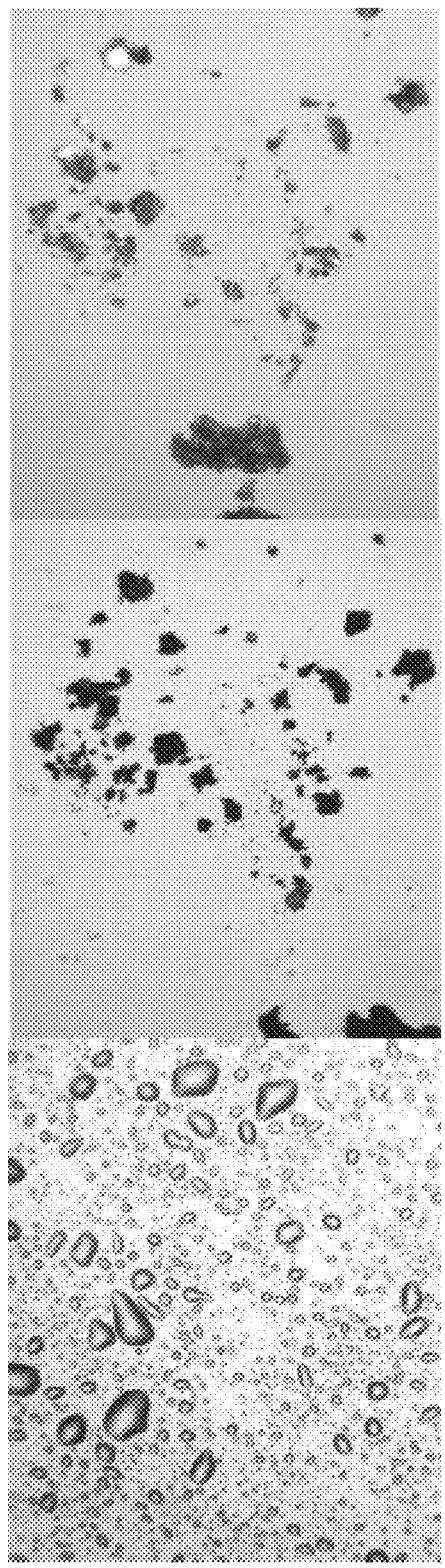
FIG. 6 shows the result of observing crystalline forms formed by melting-rapid cooling and external stimulation using an optical microscope.
Figure 7:
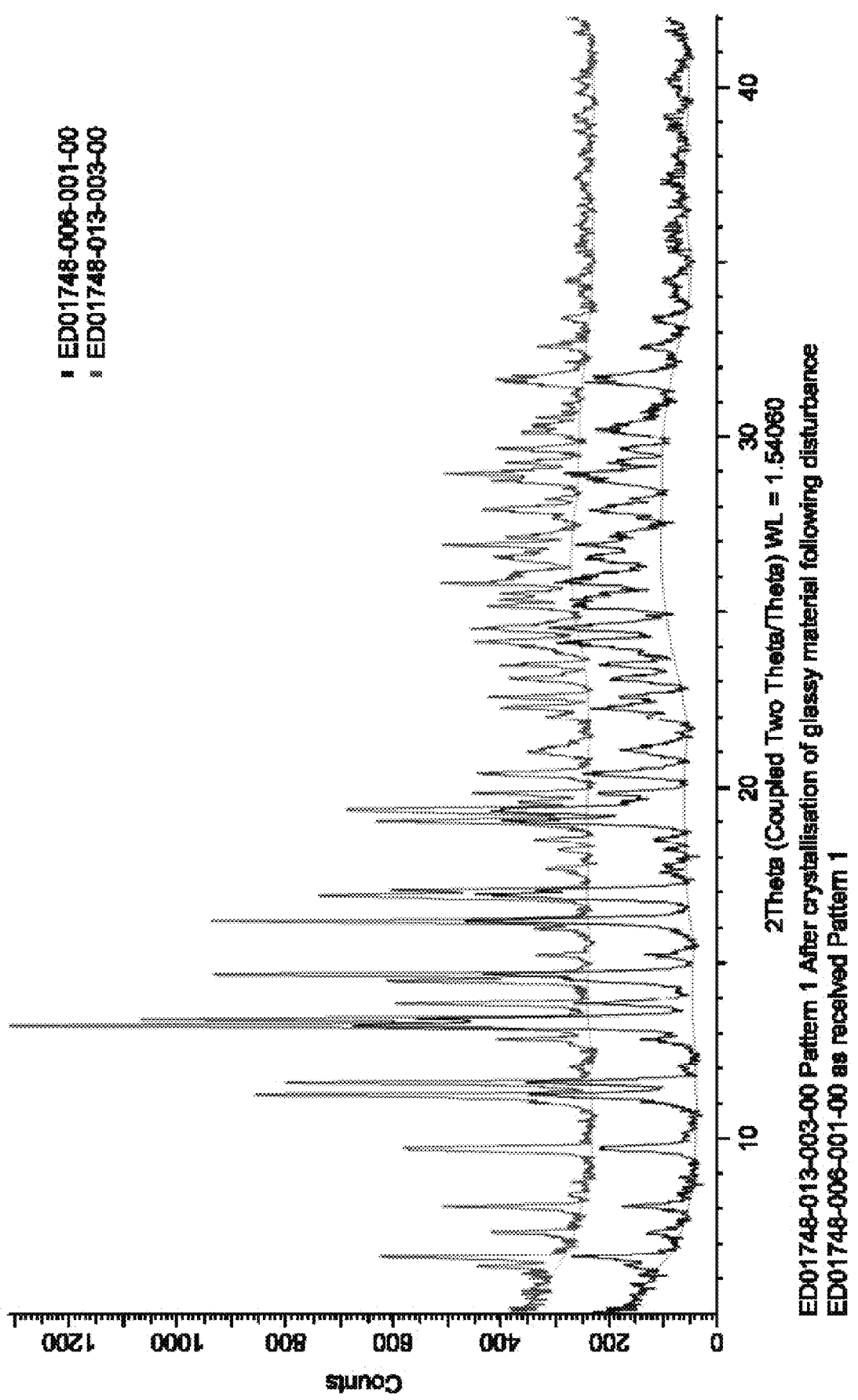
FIG. 7 shows the result of XRPD analysis for a crystalline form formed after melting-rapid cooling and storage.

Each (about 10 mg) of two ED01748-006-001-00 samples was put into a vial, and then into a drying pistol which had been preheated to 110° C. for 10 minutes under ambient pressure. The molten sample was removed, followed by rapid cooling with dry ice. As a result of observation with an optical microscope, glass droplets were observed as shown in FIG. 6. The glass material from the first sample was rapidly crystallized by impacting a part that characterized it. As a result of XRPD analysis, the glass material was identified as Pattern 1 (FIG. 7). The material was not significantly decomposed as confirmed by $^1$H NMR or UPLC, and the sample had a UPLC purity of 98.7%.

Figure 8:
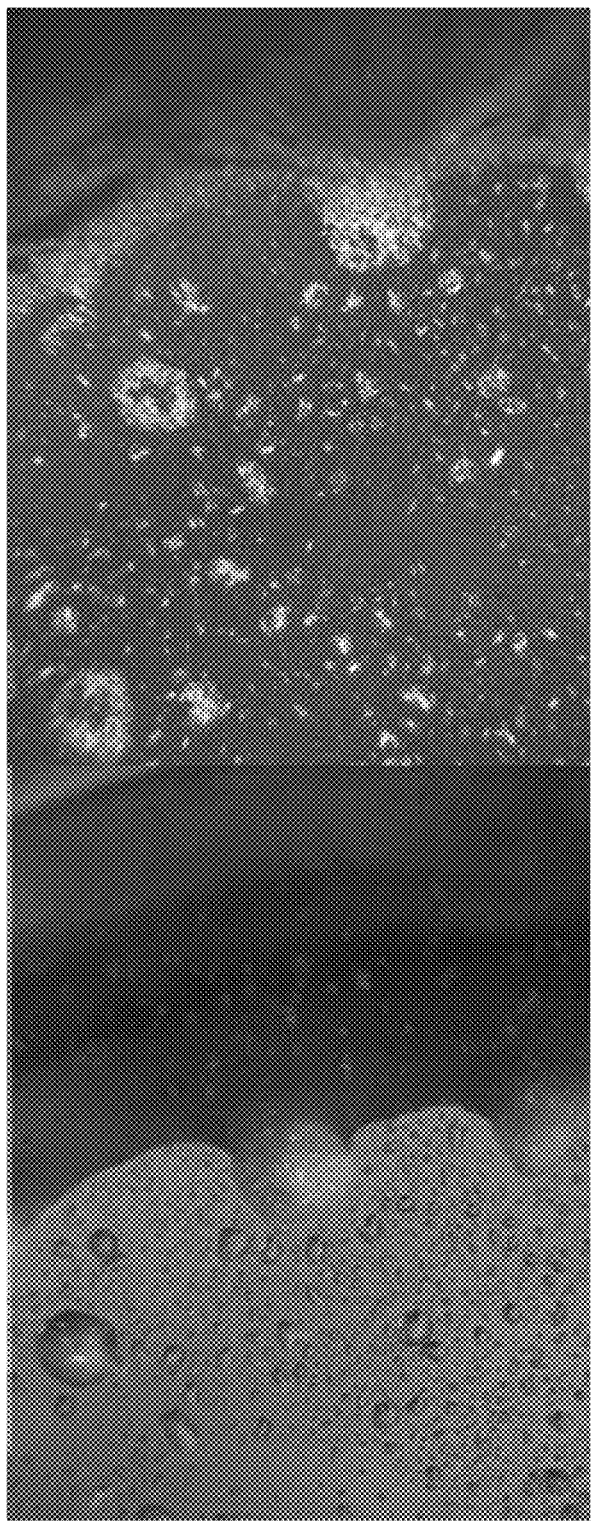
FIG. 8 shows the result of observing a crystalline form formed after melting-rapid cooling and storage using an optical microscope. (overnight (left), 4 days (right))

The second sample of the cooled material was stored in a closed vial overnight and observed using an optical microscope. A very small amount of crystalline material was observed (FIG. 8, left), and after standing for 4 days, it was confirmed that the material was completely crystallized (FIG. 8, right).

Example 2

Preparation of Pattern 1 Crystalline Form of Amorphous 1-(2-chlorophenyl)-(S)-1-hydroxypropyl-(S)-2-carbamate A polymorphic pattern of the amorphous 1-(2-chlorophenyl)-(S)-1-hydroxypropyl-(S)-2-carbamate obtained in Example 1 was confirmed using various solvents (mainly ICH Class II and III).

A portion (each 10 mg) of ED01748-006-001-00 was dispensed into a vial, and an open vial was melted in a drying pistol (preheated at 110° C.) for 10 minutes under ambient pressure. The molten sample was removed, followed by rapid cooling with dry ice. The resulting amorphous glass material was treated with one solvent selected from acetone, chloroform, methanol (MeOH), tetrahydrofuran, diisopropyl ether, ethanol (EtOH), methyl ethyl ketone, acetonitrile, 2-propanol, tert-butanol, 1,2-dimethoxyethane (DME), 1-propanol, 2-butanol, water, 1,4-dioxane, 2-methyl-1-propanol, 2-methoxyethanol, butyl acetate, methyl butyl ketone, 3-methyl-1-butanol, 1-pentanol, cumene and anisole. The sample was shaken at room temperature for 2 to 3 hours, and then solvents except t-BuOH and 1,4-dioxane were transferred to a refrigerator. The other samples were stirred overnight at room temperature.

All solid samples were analyzed using an optical microscope and XRPD. In the experiment, most of the solutions were stored in a refrigerator for 2 days, and the remaining solutions were removed with CHCl$_3$ and anisole by evaporation at room temperature. CHCl$_3$ provided a solid rapidly dissolved by evaporating the resulting solution before isolation, and anisole provided a solid dissolved at room temperature before isolation, thereby obtaining a solid after partial evaporation. The residual solid obtained by evaporation was analyzed using an optical microscope and XRPD.

Figure 9:
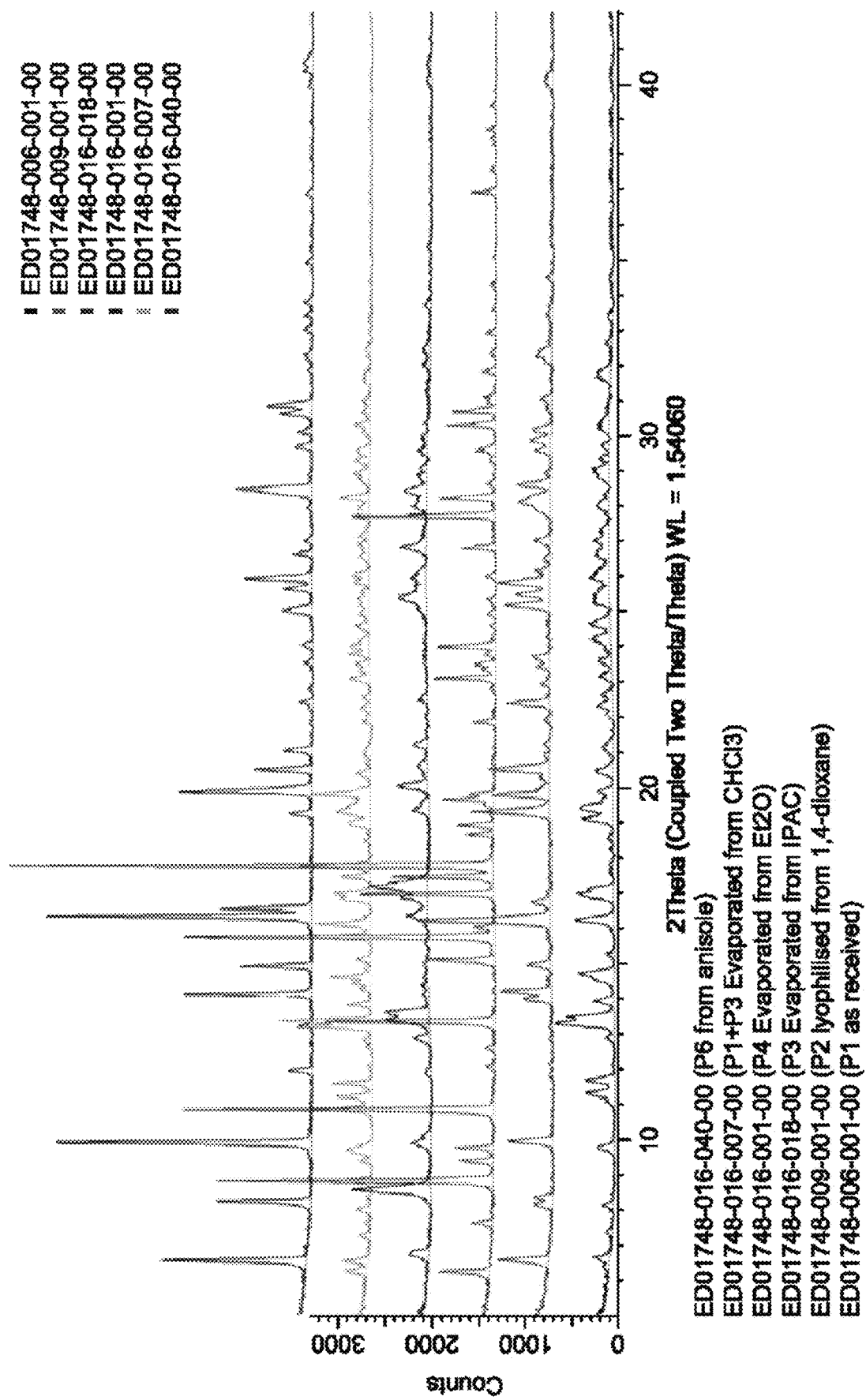
FIG. 9 shows the overlaid XRPD diffractogram results of crystalline forms of amorphous Pattern 1, 2, 3, 4 and 6.

As a result, from most of the solvents, Pattern 1 or Pattern 3 was confirmed, Pattern 4 was confirmed from diethyl ether, a mixture of Pattern 1 and Pattern 3 was confirmed from chloroform and propyl acetate, Pattern 6 was confirmed from toluene and anisole, and a mixture of Pattern 3 and Pattern 6 was confirmed from benzonitrile. It was observed that the Pattern 6 material confirmed from toluene was converted to a mixture of Pattern 6 and Pattern 3 by XRPD. The Pattern 6 material confirmed from anisole stood overnight, and then converted to a mixture of Pattern 6 and Pattern 1 by XRPD. The various XRPD diffraction patterns obtained as above are shown in FIG. 9.

Experimental Example 1

Analysis of Crystalline form Pattern 1 (ED01748-006-001-00) of (1-(2-chlorophenyl)-(S)-1-hydroxy-propyl-(S)-2-carbamate)

A crystalline form of 1-(2-chlorophenyl)-(S)-1-hydroxypropyl-(S)-2-carbamate (JBPOS0101/S-P-17001) obtained from Bio-Pharm Solutions Co. Ltd., analyzed by XRPD, is shown in FIG. 10 and Table 2 below, which is defined as Pattern 1.

TABLE 2

| Caption | Angle 2-Theta ° | d value Angstrom | Intensity Count | Intensity % |
|---|---|---|---|---|
| 6.662° | 6.662 | 13.25637 | 275 | 40.7 |
| 7.392° | 7.392 | 11.94899 | 132 | 19.6 |
| 8.153° | 8.153 | 10.83624 | 179 | 26.5 |
| 9.801° | 9.801 | 9.01695 | 219 | 32.4 |
| 11.303° | 11.303 | 7.8224 | 351 | 52 |
| 11.660° | 11.66 | 7.5835 | 357 | 52.9 |
| 12.068° | 12.068 | 7.32802 | 66 | 9.8 |
| 12.874° | 12.874 | 6.8707 | 144 | 21.3 |
| 13.280° | 13.28 | 6.66182 | 675 | 100 |
| 13.435° | 13.435 | 6.58531 | 496 | 73.5 |
| 13.913° | 13.913 | 6.36017 | 271 | 40.1 |
| 14.703° | 14.703 | 6.02005 | 434 | 64.3 |
| 15.256° | 15.256 | 5.80305 | 135 | 20 |
| 16.243° | 16.243 | 5.45254 | 467 | 69.2 |
| 16.948° | 16.948 | 5.22742 | 415 | 61.5 |
| 17.796° | 17.796 | 4.98008 | 99 | 14.7 |
| 18.266° | 18.266 | 4.85289 | 101 | 15 |
| 18.572° | 18.572 | 4.77361 | 119 | 17.6 |
| 19.091° | 19.091 | 4.64505 | 382 | 56.6 |
| 19.419° | 19.419 | 4.56748 | 420 | 62.2 |
| 19.895° | 19.895 | 4.45926 | 226 | 33.5 |
| 20.443° | 20.443 | 4.34088 | 254 | 37.6 |
| 21.124° | 21.124 | 4.20246 | 184 | 27.3 |
| 22.076° | 22.076 | 4.02326 | 131 | 19.4 |
| 22.354° | 22.354 | 3.97388 | 240 | 35.6 |
| 22.673° | 22.673 | 3.91877 | 184 | 27.3 |
| 23.174° | 23.174 | 3.83509 | 198 | 29.3 |
| 23.582° | 23.582 | 3.76964 | 224 | 33.2 |
| 24.202° | 24.202 | 3.67451 | 303 | 44.9 |
| 24.619° | 24.619 | 3.6132 | 319 | 47.3 |
| 25.260° | 25.26 | 3.52298 | 271 | 40.1 |
| 25.435° | 25.435 | 3.49906 | 279 | 41.3 |
| 25.932° | 25.932 | 3.43308 | 307 | 45.5 |
| 26.138° | 26.138 | 3.40653 | 230 | 34.1 |
| 26.614° | 26.614 | 3.34669 | 248 | 36.7 |
| 26.983° | 26.983 | 3.30175 | 268 | 39.7 |
| 27.965° | 27.965 | 3.18799 | 243 | 36 |
| 28.256° | 28.256 | 3.15585 | 161 | 23.9 |
| 28.805° | 28.805 | 3.09686 | 234 | 34.7 |
| 28.998° | 28.998 | 3.07672 | 289 | 42.8 |
| 29.319° | 29.319 | 3.0438 | 206 | 30.5 |
| 29.690° | 29.69 | 3.00656 | 180 | 26.7 |
| 30.247° | 30.247 | 2.95246 | 229 | 33.9 |
| 30.483° | 30.483 | 2.93017 | 192 | 28.4 |
| 31.697° | 31.697 | 2.82066 | 228 | 33.8 |
| 32.668° | 32.668 | 2.73894 | 140 | 20.7 |
| 33.414° | 33.414 | 2.67953 | 121 | 17.9 |

The features of Pattern 1 were confirmed as follows.

TABLE 3

| Pattern | Features |
|---|---|
| Pattern 1 (anhydrous) | Endothermic events of Onset 81° C. (small amount) and 89° C.<br>No mass loss in TGA upon decomposition.<br>In polymorphic screening, can be obtained when various solvents were added to an amorphous form, and have partially improved crystallinity (ED01748-016-014-00 of MeCN, ED01748-016-010-00 of DIPE).<br>No low temperature endothermic event. |

Figure 11:
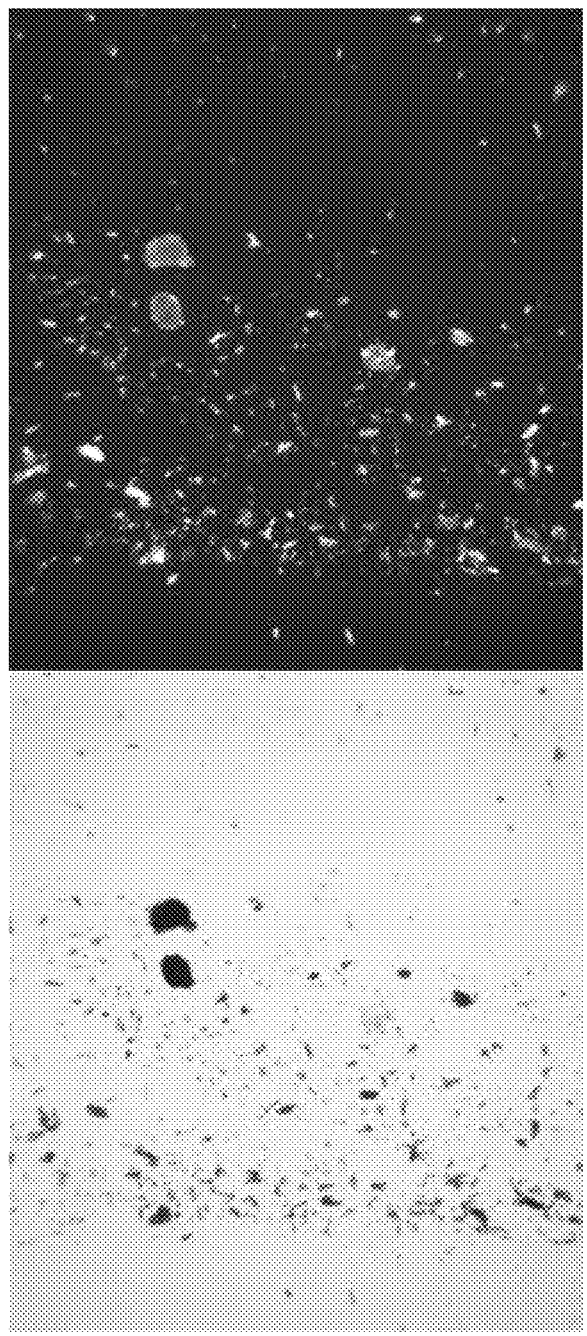
FIG. 11 shows the optical microscope images of the crystalline form of 1-(2-chlorophenyl)-(S)-1-hydroxypropyl-(S)-2-carbamate (JBPOS0101) Pattern 1.
Figure 12:
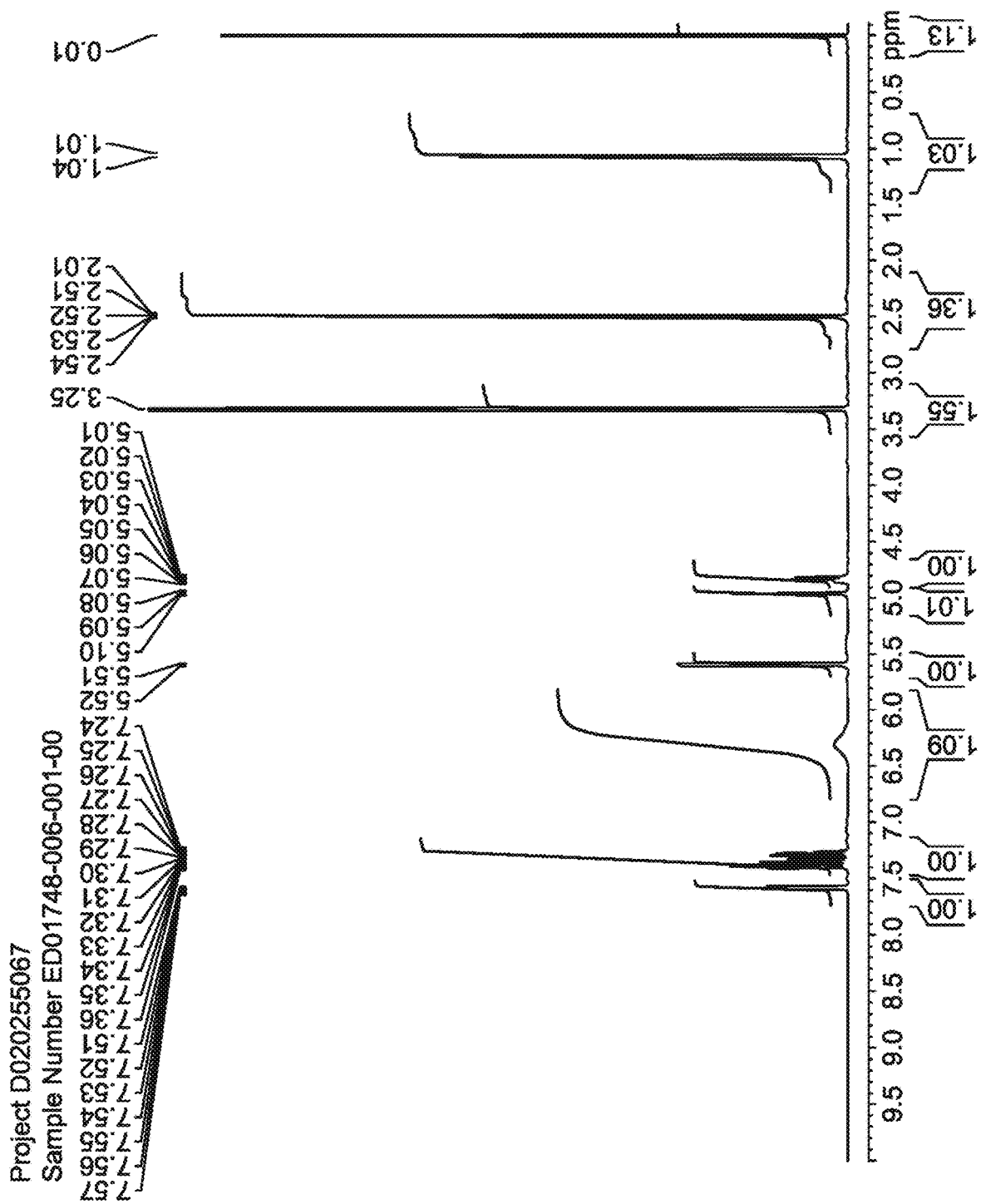
FIG. 12 shows the $^1$H NMR result of the crystalline form of 1-(2-chlorophenyl)-(S)-1-hydroxypropyl-(S)-2-carbamate (JBPOS0101) Pattern 1.
Figure 13:
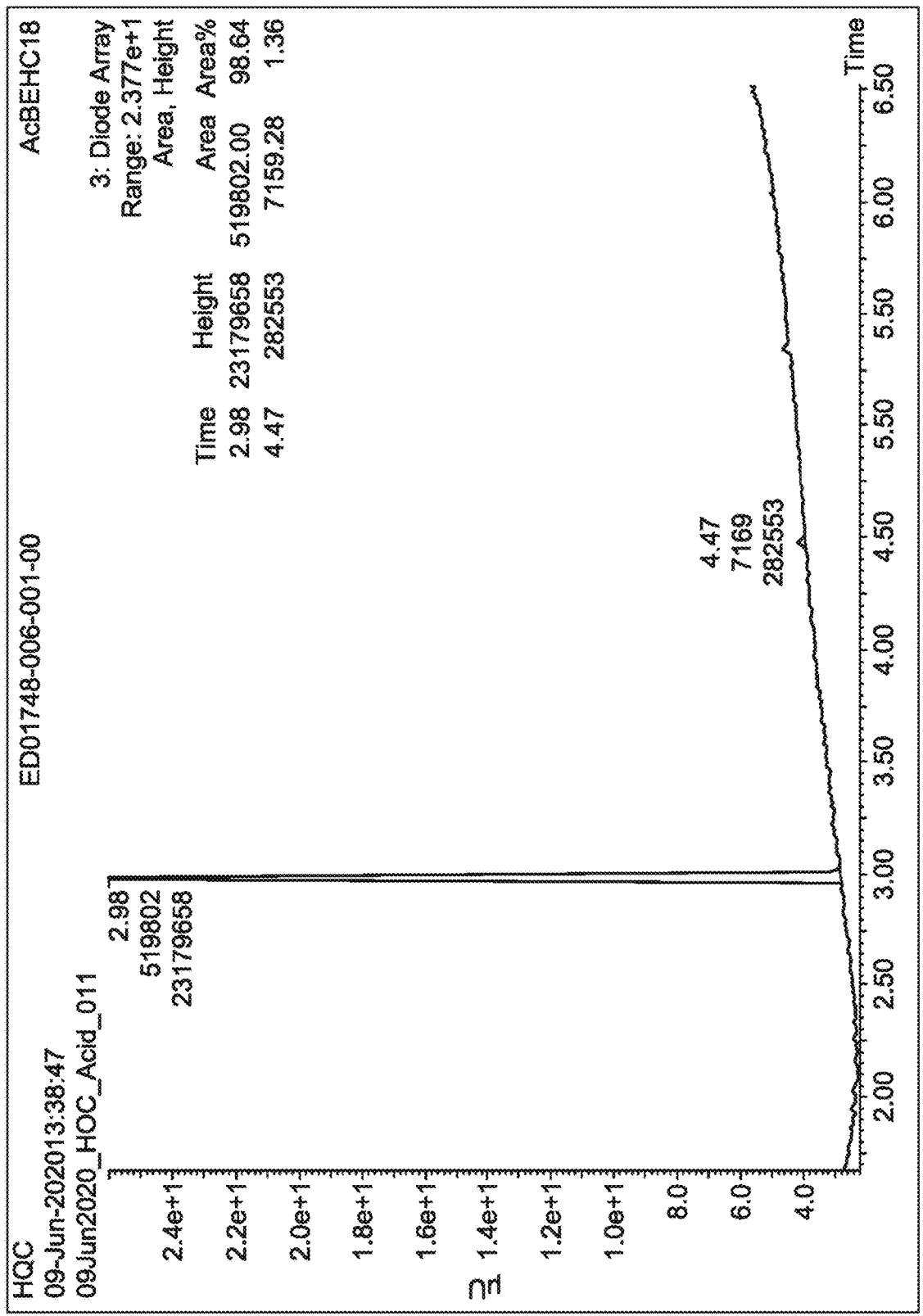
FIG. 13 shows the UV detection chromatogram result obtained by measuring the UPLC purity of the crystalline form of 1-(2-chlorophenyl)-(S)-1-hydroxypropyl-(S)-2-carbamate (JBPOS0101) Pattern 1.

The optical microscope images of the crystallized ED01748-006-001-00 Pattern 1 are shown in FIG. 11. In addition, the $^1$H NMR analysis result of the ED01748-006-001-00 corresponded to the structure shown in FIG. 12. In addition, the UPLC purity was 98.6%, as determined by a UV detection chromatogram (FIG. 13).

In addition, as a result of thermal analysis of ED01748-006-001-00 by DSC, it was confirmed that a small endothermic reaction started at 81° C. (peak 82° C.), and an endothermic reaction started at 89° C. (peak 90° C.) corresponding to a melting temperature (FIG. 14).

In addition, at temperatures of about 200° C. or more, a broad peak corresponding to a mass loss observed by TGA through decomposition was shown at 229° C. TGA shows that 95% of the mass remained even at 237° C. without considerable mass loss until a temperature exceeded about 200° C. 100% of the mass was lost at 305° C. (FIG. 15).

Figure 16:
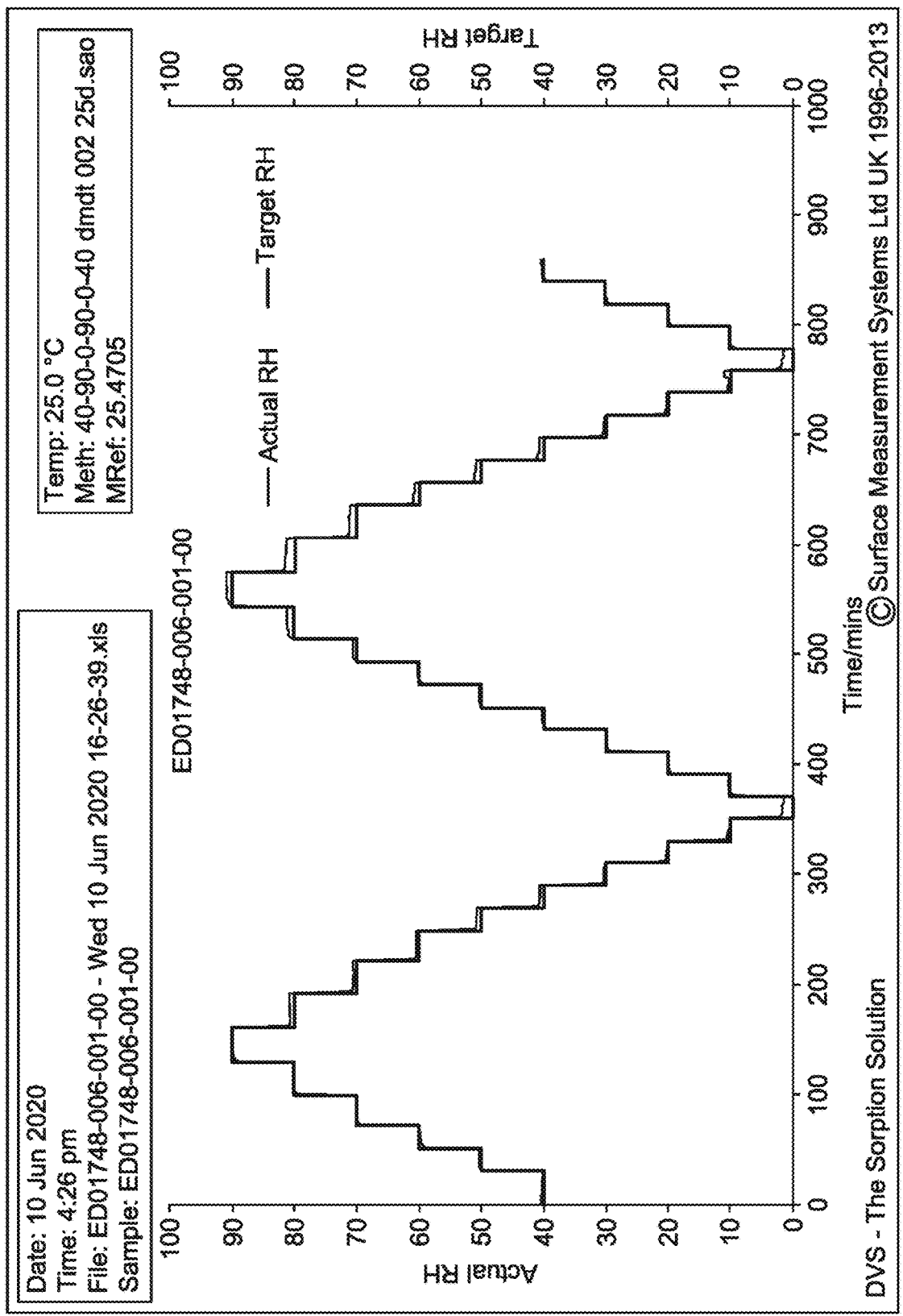
FIG. 16 shows the GVS change in the mass plot of the crystalline form of 1-(2-chlorophenyl)-(S)-1-hydroxypropyl-(S)-2-carbamate (JBPOS0101) Pattern 1.
Figure 17:
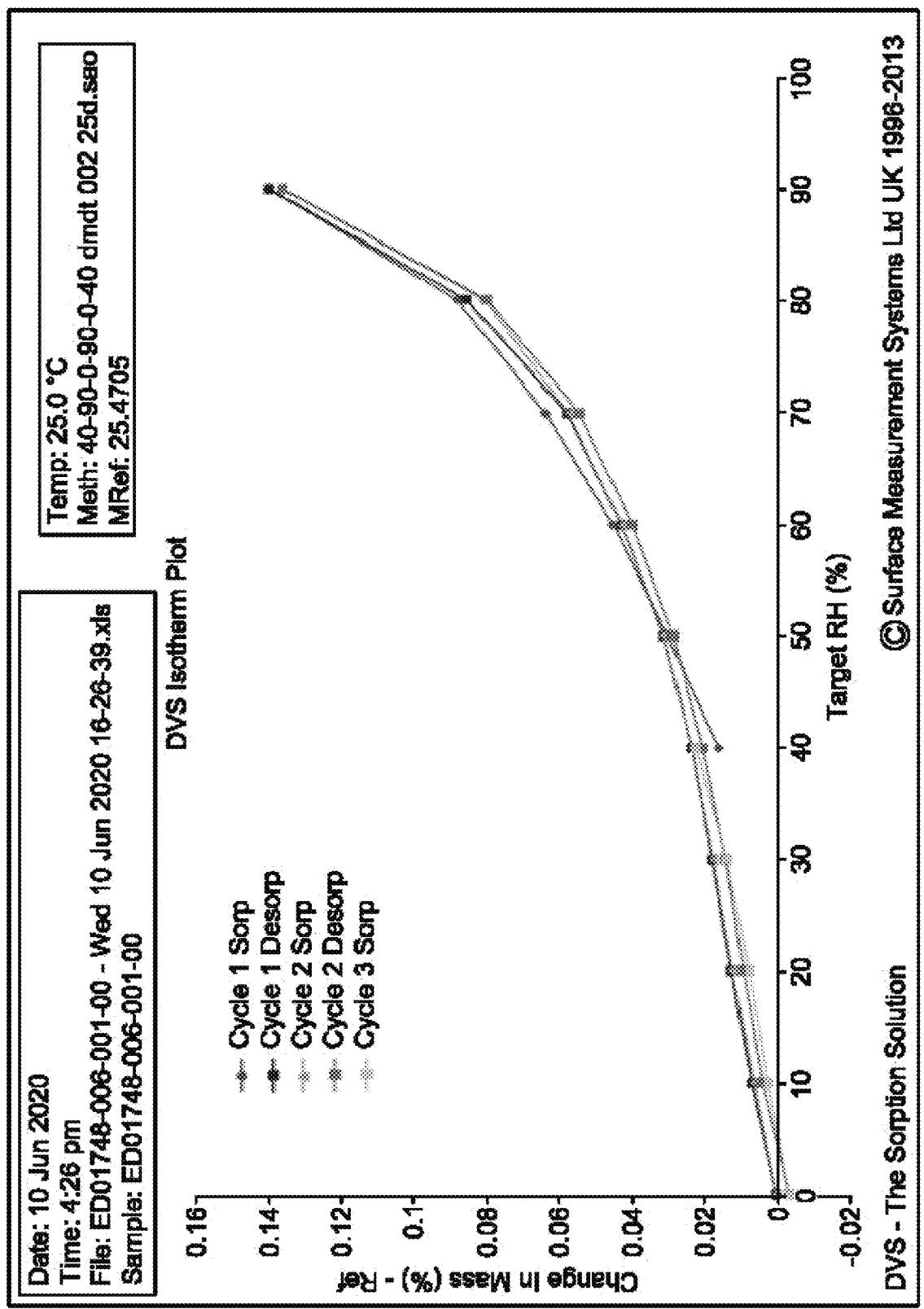
FIG. 17 shows the GVS isotherm plot of the crystalline form of 1-(2-chlorophenyl)-(S)-1-hydroxypropyl-(S)-2-carbamate (JBPOS0101) Pattern 1.

From the GVS experiment result, the ED01748-006-001-00 also showed that the mass was increased by 0.14% in a range of 0 to 90% relative humidity (R.H.) like the isotherm plot of FIG. 16. This means that a mass increase is insignificant, which shows storage stability by humidity is improved (FIGS. 16 and 17).

Figure 18:
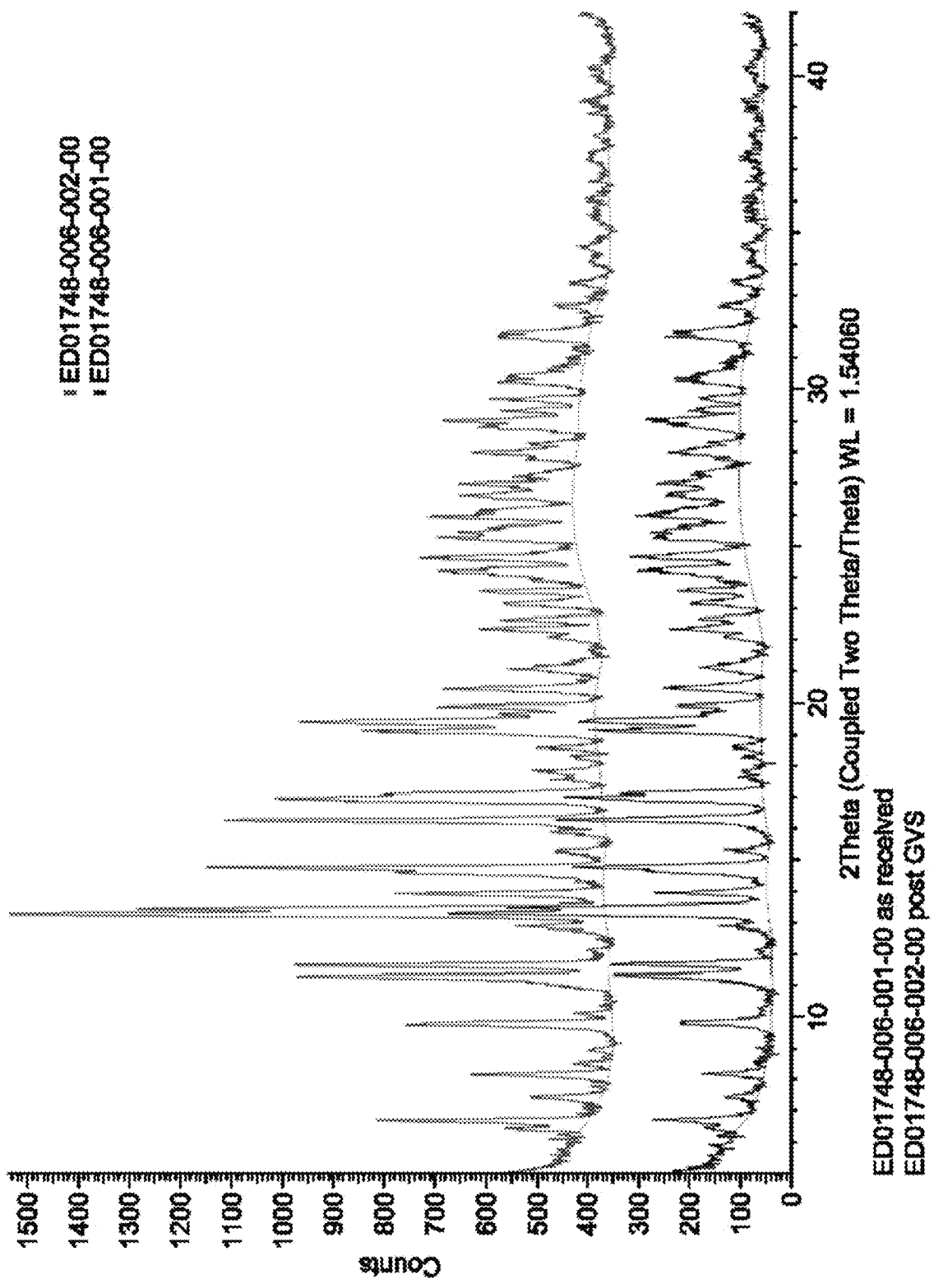
FIG. 18 shows the XRPD analysis result for the crystalline form of 1-(2-chlorophenyl)-(S)-1-hydroxypropyl-(S)-2-carbamate before and after GVS.
Figure 19:
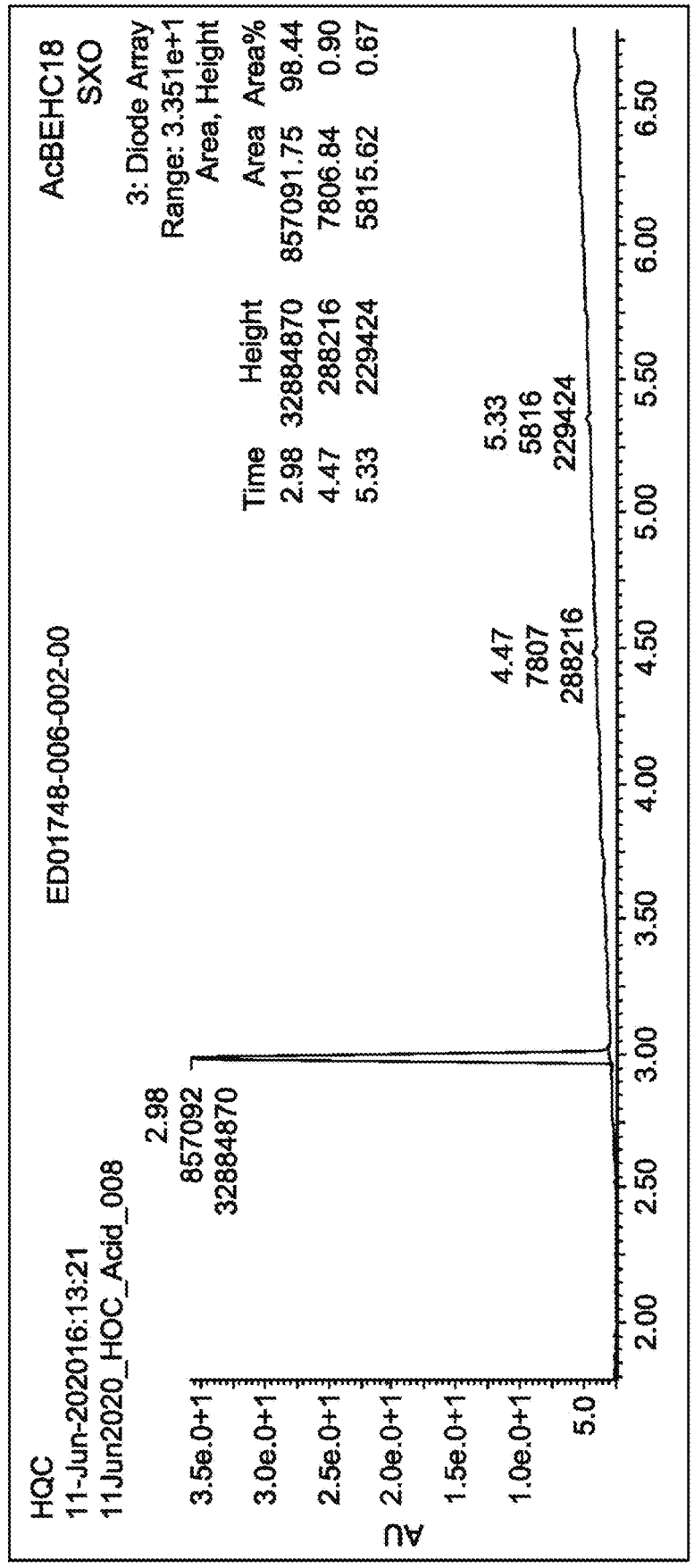
FIG. 19 shows the result of observing the change in purity before and after GVS through UPLC.

After the GVS experiment, there was no change in morphology observed from the XRPD result. When the ED01748-006-001-00 was stored under a stress condition of 40° C./75% RH or RT/97% RH, no change in morphology by XRPD was shown (FIG. 18). In addition, it was observed that the change in purity was 97.4% after 40° C./75% RH and 97.7% after RT/97% RH by UPLC (FIG. 19).

Experimental Example 2

Measurement of Solubility of Crystalline Form (ED01748-006-001-00) Pattern 1 of (1-(2-chlorophenyl)-(S)-1-hydroxypropyl-(S)-2-carbamate)

To measure the solubility of ED01748-006-001-00 Pattern 1, experiments were carried out in biological media (Fasted simulated gastric fluid (FaSSGF) and Fasted simulated intestinal fluid (FaSSIF)) at 37° C. 10 mL each of samples was dispersed into each of four vials, 1 mL each of FaSSGF and FaSSIF was added to each of the two vials and incubated in an orbital shaker for 24 hours. After incubation, all solids in each sample were dissolved, and the solubility was measured as follows.

TABLE 4

| Sample | FaSSGF solubility after 24 h | FaSSIF solubility after 24 h |
|---|---|---|
| ED01748-006-001-00 | 16.84 mg/mL | 14.05 mg/mL |

Experimental Example 3

Confirmation of Thermodynamic Stability of Crystalline Form Pattern 1 of (1-(2-chlorophenyl)-(S)-1-hydroxypropyl-(S)-2-carbamate)

3-1> Competitive Slurry Experiment for Pattern 1 and Pattern 3

To investigate the relative thermodynamic stability of various crystalline form patterns at room temperature and 50° C., competitive slurry experiments were carried out.

A mixture of Pattern 1 and Pattern 3 (ED01748-028-003-00, 4×20 mg) was dispensed into vials. They were treated with 250 μL of a saturated solution of Pattern 1 (ED01748-006-001-00) in DIPE or heptane (50 mg of ED01748-006-001-00 was treated with DIPE or heptane and heated at 50° C., a portion was removed as needed, and the resulting product was filtered through a 0.45 μm syringe filter, thereby forming a slurry). The produced slurry was stirred at room temperature or 50° C. A small sample was periodically removed and analyzed by XRPD, followed by monitoring the progress as shown in the following table. After analysis, the solid was returned to the vial, and an additional saturated solution was added as needed to maintain the slurry. After 4 days, the purity of the material was confirmed by UPLC. In both of DIPE samples, the purity was decreased to 98%, and in a heptane sample, the purity was 98.5%.

TABLE 5

| Experiment | Solvent | Conditions | Time | Result |
|---|---|---|---|---|
| ED01748-033-001 | DIPE | RT | 1 day | P1 |
| ED01748-033-002 | DIPE | 50° C. | 1 day | P1 |
| ED01748-033-003 | Heptane | RT | 1 day | P1 + P3 |
| ED01748-033-004 | Heptane | 50° C. | 1 day | P1 + P3 |
| ED01748-042-005 | DIPE | RT | 4 days | P1 |
| ED01748-042-006 | DIPE | 50° C. | 4 days | P1 |
| ED01748-042-007 | Heptane | RT | 4 days | P1 + P3 |
| ED01748-042-008 | Heptane | 50° C. | 4 days | P1 |
| ED01748-042-009 | Heptane | RT | 11 days | P1 |

Figure 20:
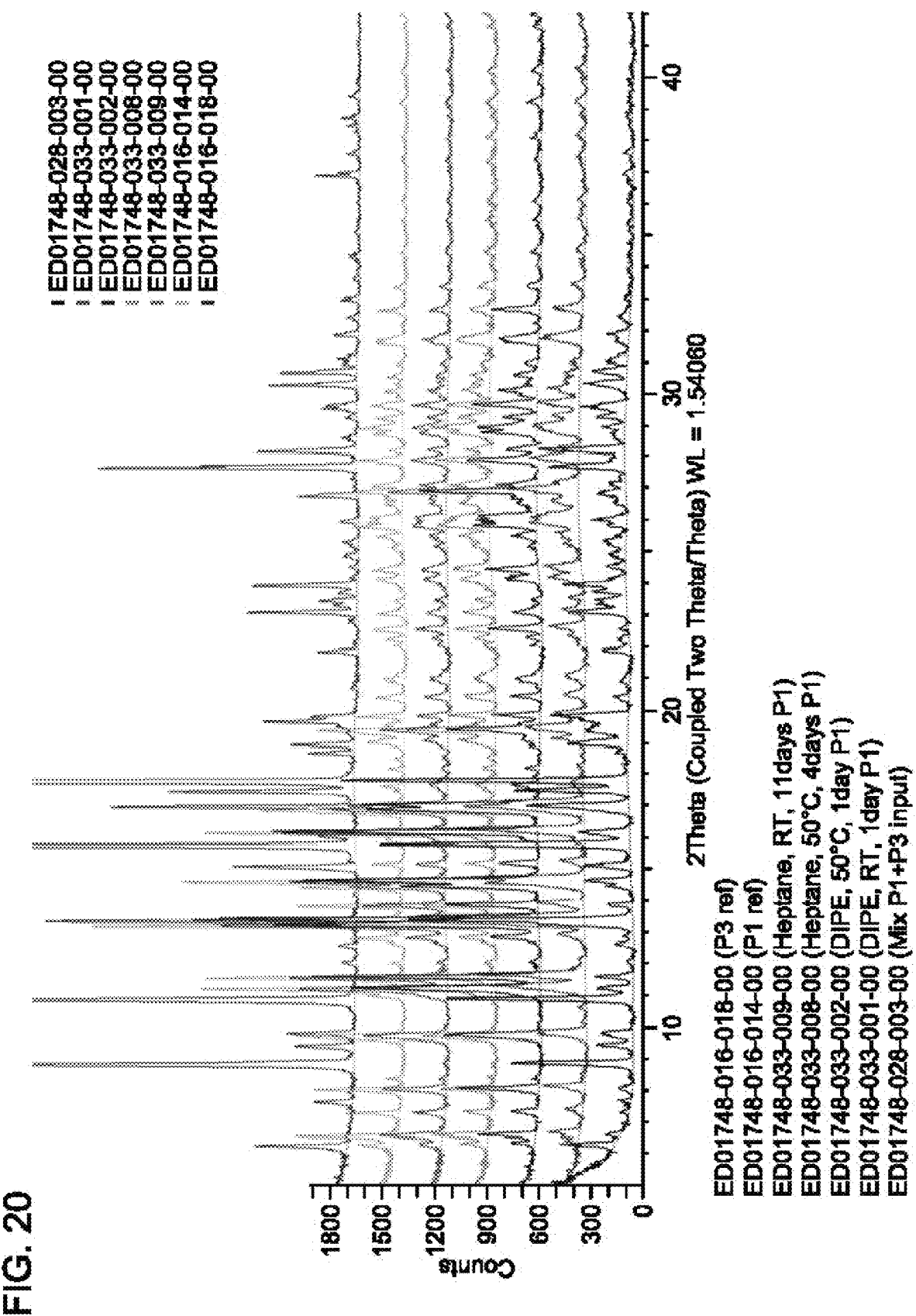
FIG. 20 is the result of forming a competitive slurry, obtained by overlaying XRPD patterns for crystalline forms of Pattern 1 and Pattern 3 and a mixture thereof after DIPE and heptane treatment.

The XRPD result of the material in this table is shown in FIG. 20. In DIPE and heptane, both types of competitive slurries of the mixture of Pattern 1 and Pattern 3, which are anhydrous, were converted to Pattern 1 at room temperature and 50° C., and XRPD showed that no Pattern 3 remains. In heptane, the conversion to Pattern 1 was slower than that of DIPE, which is caused by a difference in solubility of materials. From the result, it was confirmed that Pattern 1 is more thermodynamically stable than Pattern 3.

3-2 Competitive Slurry Experiment for Pattern 1, Pattern 3, Pattern 6 and Pattern 11

A mixture of Pattern 1 and Pattern 3 (ED01748-028-003-00, 10 mg each) was dispensed into four vials, and Pattern 6 (ED01748-034-002-00, 5 mg) and Pattern 11 (ED01748-037-002-00, 5 mg) were added to respective vials. Each sample was treated with 300 μL of a filtered saturated solution of Pattern 1 (ED01748-006-001-00) prepared in DIPE or heptane. The resulting slurries were stirred at room temperature and 50° C. A small sample was periodically removed and analyzed by XRPD, followed by monitoring as described in the following table.

After analysis, the solid was returned to the vial, and a saturated solution was additionally injected as needed to maintain the slurries. After 25 days, the purity of the solid material obtained in the heptane experiment was confirmed by UPLC, and no significant decrease in purity was shown by UPLC.

TABLE 6

| Experiment | Solvent | Conditions | Time | Result |
|---|---|---|---|---|
| ED01748-042-001 | DIPE | RT | 1 day | P1 |
| ED01748-042-002 | DIPE | 50° C. | 1 day | P1 |
| ED01748-042-003 | Heptane | RT | 1 day | P1 + P11 |
| ED01748-042-004 | Heptane | 50° C. | 1 day | P1 + P11 |
| ED01748-042-005 | Heptane | RT | 5 days | P1 + P11 |
| ED01748-042-006 | Heptane | 50° C. | 5 days | P1 + P11 |
| ED01748-042-007 | Heptane | RT | 11 days | P1 + P11 |
| ED01748-042-008 | Heptane | 50° C. | 11 days | P1 + P11 |
| ED01748-042-009 | Heptane | RT | 25 days | P1 + P11 |
| ED01748-042-010 | Heptane | 50° C. | 25 days | P1 + P11 |

Figure 21:
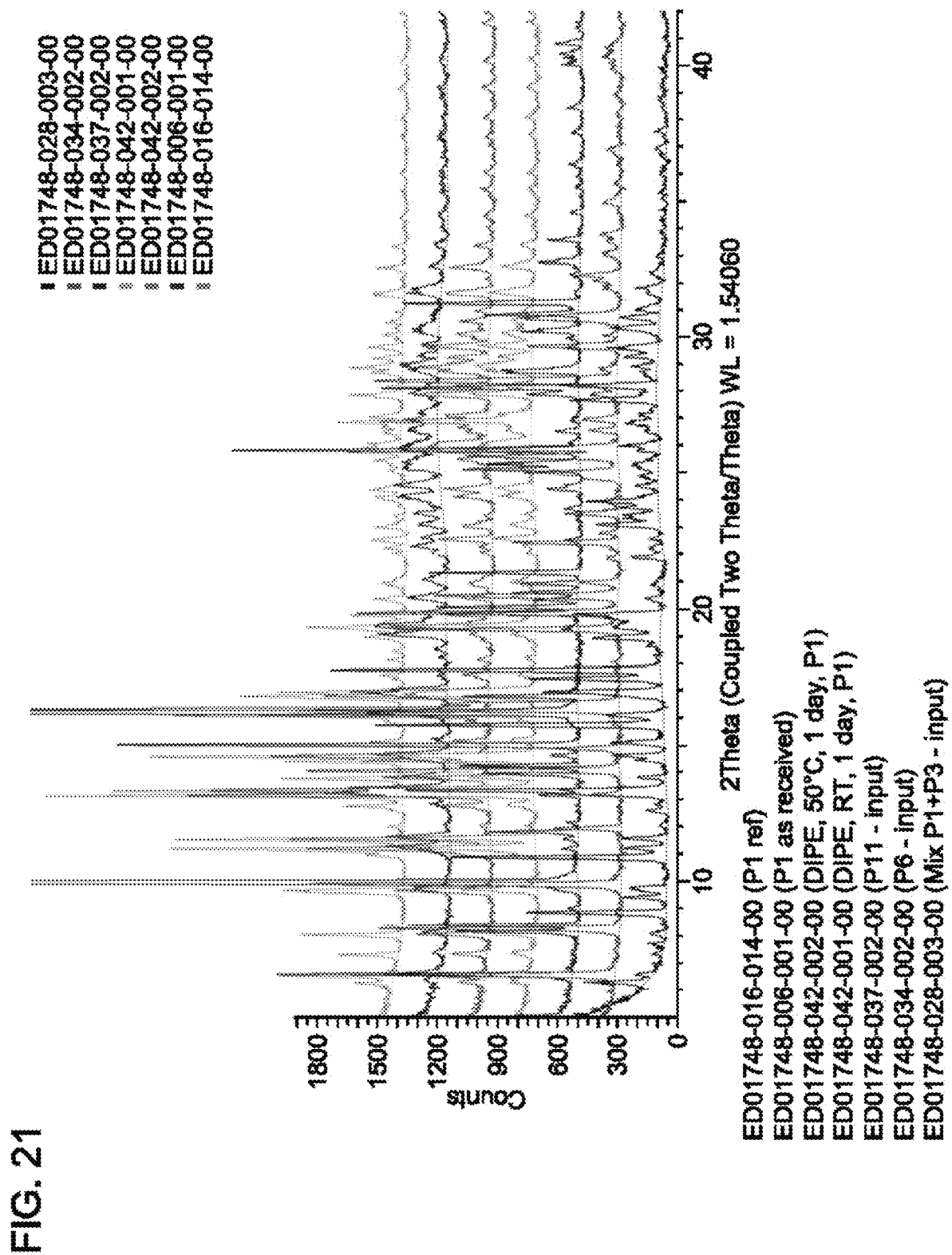
FIG. 21 and FIG. 22 are the results of forming a competitive slurry, obtained by overlaying XRPD patterns for crystalline forms of Pattern 1, Pattern 3, Pattern 6 and Pattern 11 or a mixture thereof after DIPE and heptane treatment.
Figure 22:
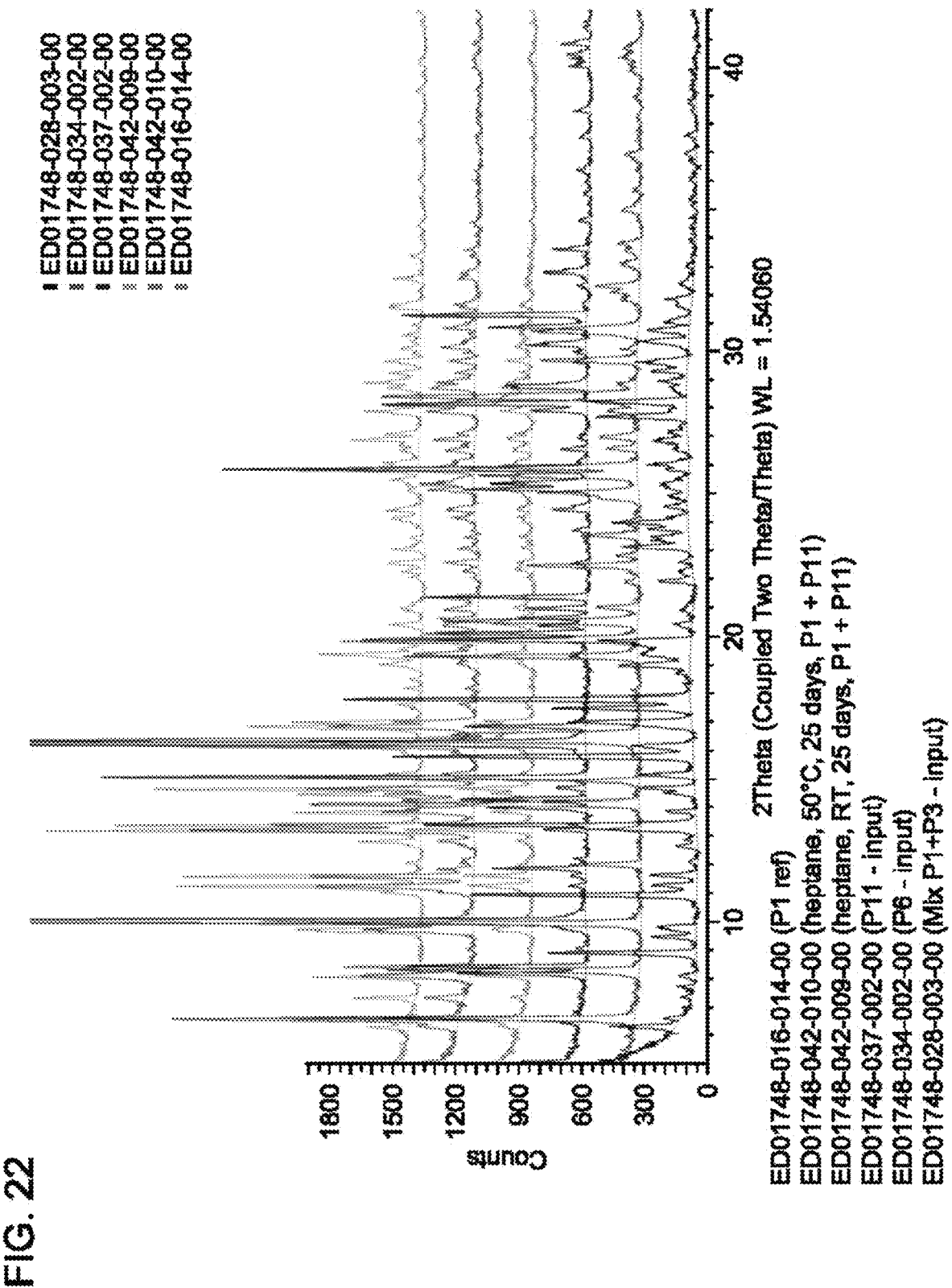

At room temperature and 50° C., after 1 day, all of the competitive slurries of the mixture of Pattern 1, Pattern 3, Pattern 6 and Pattern 11 materials in DIPE were converted to a Pattern 1 material. That is, it was confirmed that Pattern 1 is more thermodynamically stable than Pattern 3, Pattern 6 and Pattern 11 in DIPE at room temperature and 50° C. under the experimental conditions. In heptane, the mixture of Pattern 1 and Pattern 11 was present at room temperature and 50° C. after standing for 25 days, but no Pattern 6 remained. From this result, it was confirmed that Pattern 1 is more thermodynamically stable than Pattern 11 and Pattern 6 (FIGS. 21 and 22).

Example 3

Synthesis and Characterization of Crystalline Form Pattern 2 Crystalline of 1-(2-chlorophenyl)-(S)-1-hydroxypropyl-(S)-2-carbamate A portion of Pattern 1 (300 mg) was dissolved in 1,4-dioxane (4 mL) and filtered through a 0.45 μm syringe filter. The resultant solution was flash frozen in a dry ice/acetone bath and then lyophilized overnight to give Pattern 2 (98.6% UPLC purity).

XRPD analysis showed the material to be crystalline (FIG. 23A and Table 7 below) and consistent with the previous batch of Pattern 2 material prepared by lyophilization (ED01748-009-001-00).

DSC and TGA thermograms were also obtained for Pattern 2 of Formula 1 as shown in FIG. 23B and FIG. 23C, respectively. DSC shows an endothermic peak with an onset at 49° C. TGA shows about 9% weight loss between 58-191° C.

TABLE 7

XRPD Table of Pattern 2 of Formula 1

| Index | Caption | Angle 2 Theta ° | d Value Angstrom | Intensity Count | Net Intensity | Rel. Intensity |
|---|---|---|---|---|---|---|
| 1 | 6.654° | 6.654 | 13.27325 | 585.2 | 503.3 | 34% |
| 2 | 8.232° | 8.232 | 10.73186 | 287.9 | 224.7 | 15% |
| 3 | 8.414° | 8.414 | 10.49984 | 275.6 | 212.2 | 14% |
| 4 | 10.042° | 10.042 | 8.8009 | 556.8 | 495.1 | 33% |
| 5 | 11.884° | 11.884 | 7.44125 | 104.5 | 40.7 | 3% |
| 6 | 12.161° | 12.161 | 7.271871 | 109.6 | 44.1 | 3% |
| 7 | 12.889° | 12.889 | 6.862837 | 94.7 | 24.2 | 2% |
| 8 | 13.218° | 13.218 | 6.692736 | 108.9 | 33.9 | 2% |
| 9 | 14.014° | 14.014 | 6.314321 | 406.9 | 319.0 | 21% |
| 10 | 14.249° | 14.249 | 6.210653 | 635.9 | 545.2 | 37% |
| 11 | 14.609° | 14.609 | 6.058375 | 132.8 | 38.6 | 3% |
| 12 | 15.017° | 15.017 | 5.894737 | 344.1 | 247.2 | 17% |
| 13 | 16.266° | 16.266 | 5.445024 | 1591.6 | 1484.5 | 100% |
| 14 | 16.769° | 16.769 | 5.282761 | 333.8 | 224.9 | 15% |
| 15 | 19.342° | 19.342 | 4.585368 | 1055.6 | 940.9 | 63% |
| 16 | 19.827° | 19.827 | 4.474214 | 751.9 | 635.0 | 43% |

TABLE 7-continued

XRPD Table of Pattern 2 of Formula 1

| Index | Caption | Angle 2 Theta ° | d Value Angstrom | Intensity Count | Net Intensity | Rel. Intensity |
|---|---|---|---|---|---|---|
| 17 | 20.554° | 20.555 | 4.317546 | 839.9 | 723.2 | 49% |
| 18 | 20.931° | 20.931 | 4.240818 | 184.7 | 69.8 | 5% |
| 19 | 21.238° | 21.238 | 4.180117 | 173.1 | 60.4 | 4% |
| 20 | 21.945° | 21.945 | 4.046983 | 183.1 | 68.3 | 5% |
| 21 | 22.431° | 22.431 | 3.96039 | 646.3 | 528.0 | 36% |
| 22 | 23.022° | 23.022 | 3.860039 | 261.1 | 141.0 | 9% |
| 23 | 23.481° | 23.481 | 3.785576 | 257.1 | 137.5 | 9% |
| 24 | 23.683° | 23.683 | 3.753747 | 371.2 | 252.4 | 17% |
| 25 | 24.630° | 24.63 | 3.611599 | 585.2 | 503.3 | 3% |
| 26 | 25.175° | 25.175 | 3.534629 | 167.6 | 45.2 | 36% |
| 27 | 25.486° | 25.486 | 3.492186 | 665.0 | 538.9 | 29% |
| 28 | 25.809° | 25.809 | 3.449146 | 558.9 | 431.8 | 45% |
| 29 | 26.148° | 26.148 | 3.405271 | 789.8 | 662.5 | 11% |
| 30 | 26.500° | 26.5 | 3.360755 | 293.5 | 166.9 | 4% |
| 31 | 27.005° | 27.005 | 3.299082 | 189.4 | 64.5 | 12% |
| 32 | 28.119° | 28.119 | 3.170902 | 292.2 | 171.4 | 30% |
| 33 | 28.617° | 28.617 | 3.116785 | 559.1 | 443.7 | 26% |
| 34 | 28.941° | 28.941 | 3.082644 | 503.8 | 391.1 | 4% |
| 35 | 29.601° | 29.601 | 3.01542 | 166.1 | 56.4 | 13% |
| 36 | 29.894° | 29.894 | 2.986496 | 294.1 | 189.6 | 19% |
| 37 | 30.218° | 30.218 | 2.955187 | 383.4 | 281.7 | 12% |
| 38 | 30.837° | 30.837 | 2.897335 | 280.3 | 182.5 | 4% |
| 39 | 31.063° | 31.063 | 2.876731 | 148.8 | 58.1 | 7% |
| 40 | 31.658° | 31.658 | 2.824047 | 195.6 | 107.2 | 2% |
| 41 | 32.372° | 32.372 | 2.763355 | 118.7 | 33.1 | 11% |
| 42 | 32.931° | 32.931 | 2.717684 | 251.2 | 163.5 | 3% |
| 43 | 33.525° | 33.525 | 2.670933 | 138.2 | 51.9 | 4% |
| 44 | 34.547° | 34.547 | 2.594185 | 135.3 | 53.1 | 5% |
| 45 | 35.591° | 35.591 | 2.520424 | 140.6 | 70.7 | 5% |
| 46 | 36.026° | 36.026 | 2.490971 | 130.4 | 68.2 | 3% |
| 47 | 37.268° | 37.268 | 2.410808 | 114.7 | 49.4 | 2% |
| 48 | 37.636° | 37.636 | 2.388055 | 93.5 | 24.4 | 2% |
| 49 | 38.551° | 38.551 | 2.333475 | 96.9 | 27.7 | 2% |
| 50 | 40.101° | 40.101 | 2.246761 | 92.4 | 23.8 | 7% |

Example 4

Synthesis and Characterization of Crystalline Form Pattern 3 Crystalline of 1-(2-chlorophenyl)-(S)-1-hydroxypropyl-(S)-2-carbamate 300 mg of Pattern 1 was placed into an open topped vial. This was placed in a drying pistol pre-heated to 110° C. and under ambient atmospheric conditions and heated at this temperature for 15 minutes. The molten material was then rapidly quench cooled by plunging into dry ice. The resultant glass was examined by optical microscopy and showed no evidence of crystalline material. This amorphous material was treated with heptane (2 mL). The glassy material did not dissolve. The resultant mixture was shaken at room temperature overnight and then a further 0.5 mL of heptane was added and some solid was gently scraped off the sides of the vial. There was still a small glassy region remaining at the base of the vial. After shaking for a further 4 hours at room temperature this had also crystallized. The solid was isolated by filtration and dried briefly under suction to give Pattern 3 (270 mg, 90%; 98.6% UPLC purity).

The XRPD pattern showed that Pattern 3 was crystalline (FIG. 24A and Table 8). DSC and TGA thermograms were also obtained for Pattern 3 of Formula 1 as shown in FIG. 24B and FIG. 24C, respectively. DSC shows an endothermic peak with an onset at 82° C. TGA shows no significant mass loss until decomposition above about 210° C.

TABLE 8

XRPD Table of Pattern 3 of Formula 1

| Index | Caption | Angle 2 Theta ° | d Value Angstrom | Intensity Count | Net Intensity | Rel. Intensity |
|---|---|---|---|---|---|---|
| 1 | 6.336° | 6.336 | 13.93926 | 744.9 | 636.4 | 14% |
| 2 | 6.621° | 6.621 | 13.33832 | 147.4 | 47.6 | 1% |
| 3 | 7.718° | 7.718 | 11.44593 | 362.6 | 285.4 | 6% |
| 4 | 8.914° | 8.914 | 9.912663 | 2184.1 | 2104.4 | 45% |
| 5 | 9.481° | 9.481 | 9.320601 | 522.5 | 444.9 | 10% |
| 6 | 9.849° | 9.849 | 8.973114 | 350.9 | 277.1 | 6% |
| 7 | 10.079° | 10.079 | 8.769467 | 134.0 | 63.4 | 1% |
| 8 | 10.919° | 10.919 | 8.095963 | 2971.3 | 2902.6 | 62% |
| 9 | 12.104° | 12.104 | 7.306362 | 148.2 | 82.9 | 2% |
| 10 | 12.632° | 12.632 | 7.001914 | 234.0 | 167.8 | 4% |
| 11 | 13.381° | 13.381 | 6.61166 | 2223.3 | 2156.3 | 46% |
| 12 | 14.266° | 14.266 | 6.203578 | 118.5 | 60.3 | 1% |
| 13 | 15.155° | 15.155 | 5.84165 | 918.1 | 846.1 | 18% |
| 14 | 15.800° | 15.8 | 5.604529 | 4749.3 | 4667.6 | 100% |
| 15 | 16.087° | 16.087 | 5.505167 | 286.4 | 202.2 | 4% |
| 16 | 17.022° | 17.022 | 5.204755 | 1397.7 | 1304.8 | 28% |
| 17 | 17.507° | 17.507 | 5.061515 | 1341.5 | 1243.0 | 27% |
| 18 | 17.816° | 17.816 | 4.974424 | 4329.8 | 4229.5 | 91% |
| 19 | 18.346° | 18.346 | 4.831913 | 163.7 | 63.2 | 1% |
| 20 | 18.718° | 18.718 | 4.736824 | 296.0 | 195.3 | 14% |
| 21 | 18.968° | 18.968 | 4.67485 | 648.1 | 547.5 | 12% |
| 22 | 19.290° | 19.29 | 4.597661 | 345.2 | 246.1 | 5% |
| 23 | 19.842° | 19.842 | 4.470953 | 1094.9 | 1001.6 | 21% |
| 24 | 20.903° | 20.903 | 4.246267 | 138.3 | 65.8 | 1% |
| 25 | 21.913° | 21.913 | 4.052833 | 383.1 | 312.5 | 7% |
| 26 | 22.247° | 22.247 | 3.992831 | 132.6 | 57.2 | 1% |
| 27 | 23.162° | 23.162 | 3.837123 | 1128.3 | 1043.7 | 22% |
| 28 | 23.529° | 23.529 | 3.777981 | 444.4 | 358.2 | 8% |
| 29 | 23.800° | 23.8 | 3.735555 | 432.4 | 346.3 | 7% |
| 30 | 24.023° | 24.023 | 3.701461 | 744.9 | 636.4 | 21% |
| 31 | 24.625° | 24.625 | 3.61233 | 1056.7 | 971.4 | 2% |
| 32 | 24.936° | 24.936 | 3.567931 | 184.8 | 104.4 | 4% |
| 33 | 25.309° | 25.309 | 3.516192 | 265.0 | 187.8 | 3% |
| 34 | 26.031° | 26.031 | 3.420315 | 227.5 | 156.0 | 4% |
| 35 | 26.836° | 26.836 | 3.319469 | 276.1 | 208.6 | 7% |
| 36 | 27.154° | 27.154 | 3.281378 | 382.4 | 305.5 | 2% |
| 37 | 27.719° | 27.719 | 3.215742 | 152.6 | 70.2 | 27% |
| 38 | 28.240° | 28.24 | 3.157599 | 1339.2 | 1250.3 | 18% |
| 39 | 28.658° | 28.658 | 3.112448 | 941.9 | 851.0 | 2% |
| 40 | 28.919° | 28.919 | 3.084961 | 200.7 | 110.8 | 1% |
| 41 | 29.296° | 29.296 | 3.046102 | 141.0 | 53.1 | 4% |
| 42 | 29.590° | 29.59 | 3.016512 | 269.3 | 183.6 | 6% |
| 43 | 30.355° | 30.355 | 2.942188 | 382.1 | 296.8 | 17% |
| 44 | 30.753° | 30.753 | 2.905053 | 860.2 | 778.1 | 12% |
| 45 | 31.133° | 31.133 | 2.87042 | 621.2 | 539.9 | 4% |
| 46 | 31.877° | 31.877 | 2.805122 | 256.5 | 178.0 | 4% |
| 47 | 32.417° | 32.417 | 2.759587 | 264.2 | 193.0 | 3% |
| 48 | 32.982° | 32.982 | 2.713599 | 187.8 | 118.6 | 3% |
| 49 | 33.655° | 33.655 | 2.660844 | 201.6 | 138.8 | 1% |
| 50 | 34.350° | 34.35 | 2.608626 | 116.0 | 56.0 | 1% |
| 51 | 35.111° | 35.111 | 2.553829 | 105.9 | 46.0 | 1% |
| 52 | 35.390° | 35.39 | 2.534331 | 105.0 | 46.4 | 1% |
| 53 | 36.918° | 36.918 | 2.43287 | 85.4 | 26.7 | 4% |
| 54 | 37.562° | 37.562 | 2.392611 | 238.8 | 180.3 | 3% |
| 55 | 38.494° | 38.494 | 2.336757 | 186.9 | 127.5 | 2% |
| 56 | 38.734° | 38.734 | 2.322875 | 162.2 | 96.7 | 3% |
| 57 | 39.410° | 39.41 | 2.284549 | 189.8 | 123.3 | 3% |
| 58 | 39.902° | 39.902 | 2.257527 | 195.0 | 129.7 | 1% |
| 59 | 41.017° | 41.017 | 2.198692 | 87.4 | 26.9 | 1% |
| 60 | 41.790° | 41.79 | 2.159796 | 87.8 | 39.9 | 1% |

Example 5

Synthesis and Characterization of Crystalline Form Pattern 4 Crystalline of 1-(2-chlorophenyl)-(S)-1-hydroxypropyl-(S)-2-carbamate 300 mg of Pattern 1 was placed into an open topped vial. This was placed in a drying pistol pre-heated to 110° C. and under ambient atmospheric conditions and heated at this temperature for 12 minutes. The molten material was then rapidly quench cooled by plunging into dry ice. The resultant glass was examined by optical microscopy and showed no evidence of crystalline material. This amorphous material was treated with diethyl ether (1.5 mL) to give a solution and shaken at room temperature overnight. As no crystals were observed the solution was transferred to the refrigerator and left to stand overnight and Pattern 4 formed. The XRPD pattern of Pattern 4 is shown in FIG. 25A and Table 9.

Figure 25B:
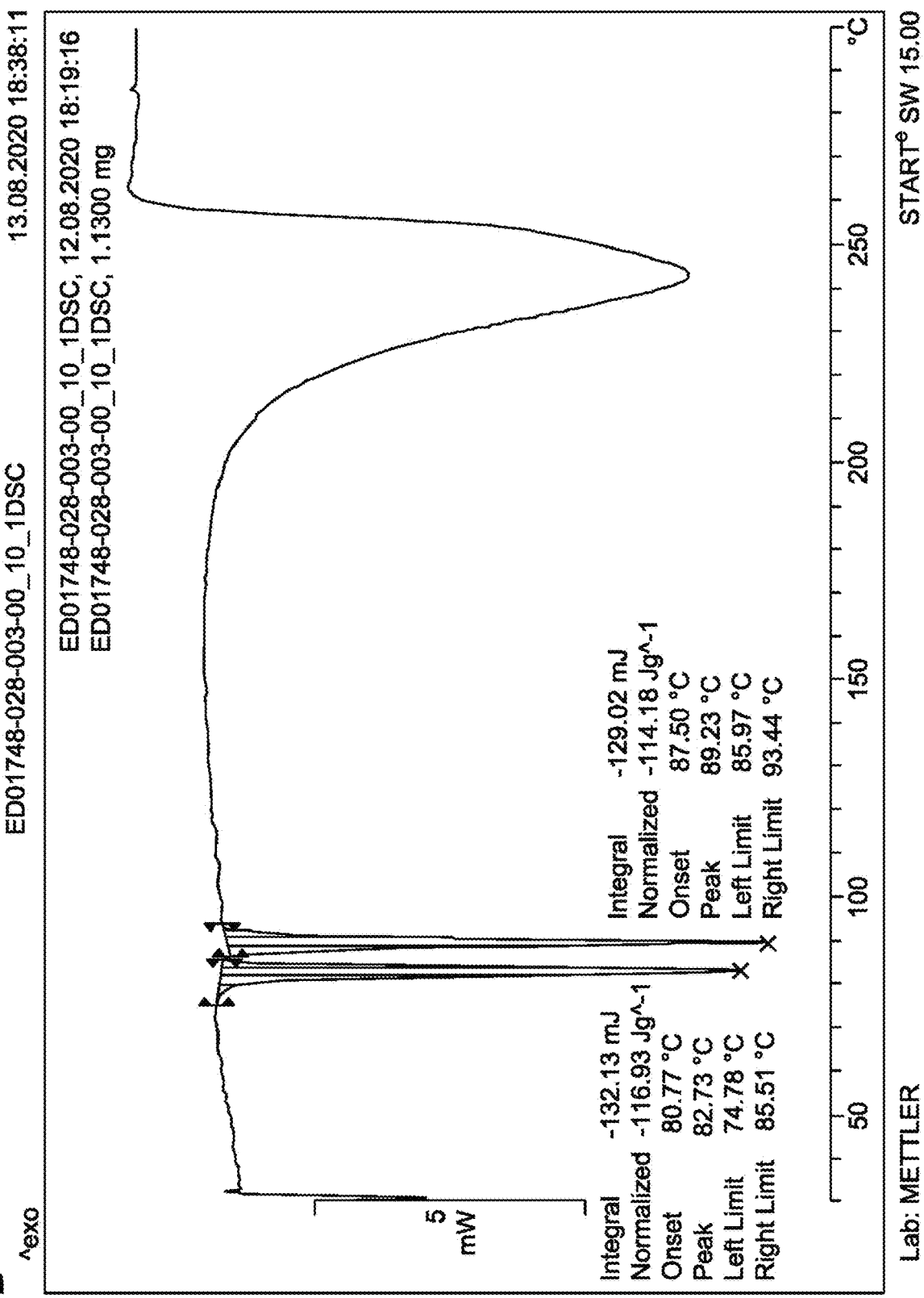
FIG. 25B shows a differential scanning calorimetry (DSC) thermogram of material following isolation of crystalline form Pattern 4 of Formula 1.

The remainder of the material was isolated by brief filtration under a stream of nitrogen. It gave a sticky solid which was consistent by XRPD with Pattern 4. Brief drying of this sticky material whilst standing in the open vial gave less sticky material which showed a change in form by XRPD from Pattern 4 to a mixture of Pattern 1 and Pattern 3 by XRPD (98.3% UPLC purity). DSC thermogram was obtained as shown in FIG. 25B. DSC shows an endothermic peak with an onset at 81° C. and 88° C. consistent with a mixture of Pattern 1+Pattern 3.

TABLE 9

XRPD Table of Pattern 4 of Formula 1

| Index | Caption | Angle 2 Theta ° | d Value Angstrom | Intensity Count | Net Intensity | Rel. Intensity |
|---|---|---|---|---|---|---|
| 1 | 6.904° | 6.904 | 12.79366 | 694.2 | 580.1 | 27% |
| 2 | 8.636° | 8.636 | 10.23091 | 2192.8 | 2118.2 | 100% |
| 3 | 9.969° | 9.969 | 8.865413 | 389.8 | 312.9 | 15% |
| 4 | 11.921° | 11.921 | 7.418169 | 427.1 | 348.4 | 16% |
| 5 | 12.867° | 12.868 | 6.874347 | 568.1 | 477.8 | 23% |
| 6 | 13.428° | 13.428 | 6.588633 | 988.6 | 888.4 | 42% |
| 7 | 13.653° | 13.653 | 6.480419 | 2027.0 | 1923.6 | 91% |
| 8 | 14.717° | 14.717 | 6.014249 | 220.0 | 108.1 | 5% |
| 9 | 15.035° | 15.035 | 5.88803 | 403.8 | 291.3 | 14% |
| 10 | 15.627° | 15.627 | 5.665976 | 357.1 | 246.2 | 12% |
| 11 | 16.949° | 16.949 | 5.226864 | 568.4 | 455.7 | 22% |
| 12 | 17.245° | 17.245 | 5.138061 | 1526.0 | 1413.4 | 67% |
| 13 | 17.391° | 17.391 | 5.09524 | 2004.2 | 1891.9 | 89% |
| 14 | 19.570° | 19.570 | 4.532434 | 582.8 | 473.5 | 22% |
| 15 | 20.117° | 20.117 | 4.410478 | 1007.3 | 895.7 | 42% |
| 16 | 20.428° | 20.428 | 4.344045 | 268.3 | 156.7 | 7% |
| 17 | 20.668° | 20.668 | 4.294188 | 175.1 | 64.1 | 3% |
| 18 | 21.257° | 21.257 | 4.176502 | 445.6 | 335.3 | 16% |
| 19 | 21.690° | 21.690 | 4.09407 | 264.6 | 154.8 | 7% |
| 20 | 22.071° | 22.071 | 4.02422 | 203.5 | 95.4 | 5% |
| 21 | 23.797° | 23.797 | 3.736009 | 252.9 | 136.6 | 6% |
| 22 | 24.161° | 24.161 | 3.680669 | 237.3 | 118.0 | 6% |
| 23 | 25.382° | 25.382 | 3.506276 | 893.6 | 763.1 | 36% |
| 24 | 25.727° | 25.727 | 3.460072 | 350.4 | 216.5 | 10% |
| 25 | 26.137° | 26.137 | 3.406705 | 697.9 | 561.5 | 27% |
| 26 | 26.838° | 26.838 | 3.319255 | 936.0 | 798.7 | 38% |
| 27 | 27.333° | 27.333 | 3.26021 | 219.2 | 84.1 | 4% |
| 28 | 27.986° | 27.986 | 3.185643 | 515.3 | 382.5 | 18% |
| 29 | 28.456° | 28.456 | 3.134095 | 1930.1 | 1800.1 | 85% |
| 30 | 29.089° | 29.089 | 3.067292 | 746.7 | 623.8 | 29% |
| 31 | 29.540° | 29.540 | 3.021475 | 435.6 | 320.0 | 15% |
| 32 | 31.429° | 31.429 | 2.844048 | 157.5 | 65.3 | 3% |
| 33 | 31.574° | 31.574 | 2.831377 | 160.4 | 68.2 | 3% |
| 34 | 32.096° | 32.096 | 2.78644 | 606.7 | 516.1 | 24% |
| 35 | 32.377° | 32.377 | 2.762932 | 457.5 | 368.9 | 17% |
| 36 | 33.797° | 33.797 | 2.65003 | 332.0 | 247.8 | 12% |
| 37 | 34.317° | 34.317 | 2.611056 | 186.6 | 101.7 | 5% |
| 38 | 35.038° | 35.038 | 2.55894 | 155.4 | 73.7 | 3% |
| 39 | 35.400° | 35.400 | 2.533632 | 412.5 | 334.2 | 16% |
| 40 | 36.922° | 36.922 | 2.43257 | 125.4 | 53.5 | 3% |
| 41 | 38.004° | 38.004 | 2.36579 | 153.4 | 84.8 | 4% |
| 42 | 38.989° | 38.989 | 2.308263 | 92.7 | 25.1 | 1% |
| 43 | 40.093° | 40.093 | 2.24719 | 136.1 | 64.8 | 3% |
| 44 | 40.751° | 40.751 | 2.212412 | 185.4 | 112.8 | 5% |
| 45 | 41.250° | 41.250 | 2.186823 | 161.3 | 90.4 | 4% |

Example 6

Synthesis and Characterization of Crystalline Form Pattern 5 Crystalline of 1-(2-chlorophenyl)-(S)-1-hydroxypropyl-(S)-2-carbamate Pattern 5 was obtained from chloroform or propyl acetate. Pattern 5 was assigned as a mixture of Pattern 1 and Pattern 3.

| Experiment | Solvent | Volume/uL | Observations | Notes | Pattern |
|---|---|---|---|---|---|
| 1 | chloroform | 50 | Soluble | Refrigerated, gave solid, which rapidly dissolved at RT, evaporated | Pattern 5 or Mix Pattern 1 + Pattern 3 |
| 2 | propyl acetate | 50 | Soluble | Refrigerated, evaporated | Pattern 5 or Pattern 1 + Pattern 3 mixture. No change on standing overnight |

Figure 26B:
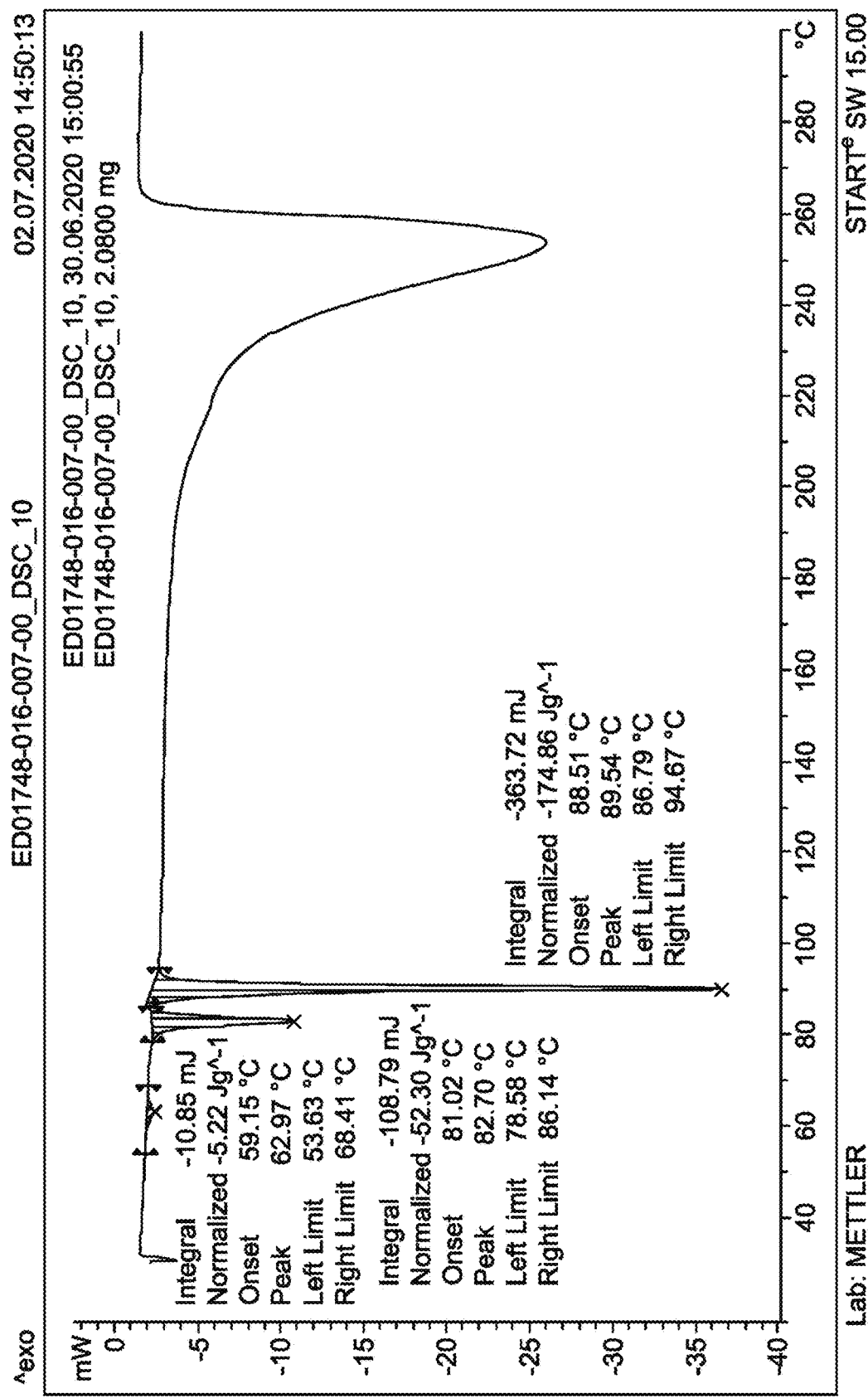
FIG. 26B shows a differential scanning calorimetry (DSC) thermogram of crystalline form Pattern 5 of Formula 1.
Figure 26C:
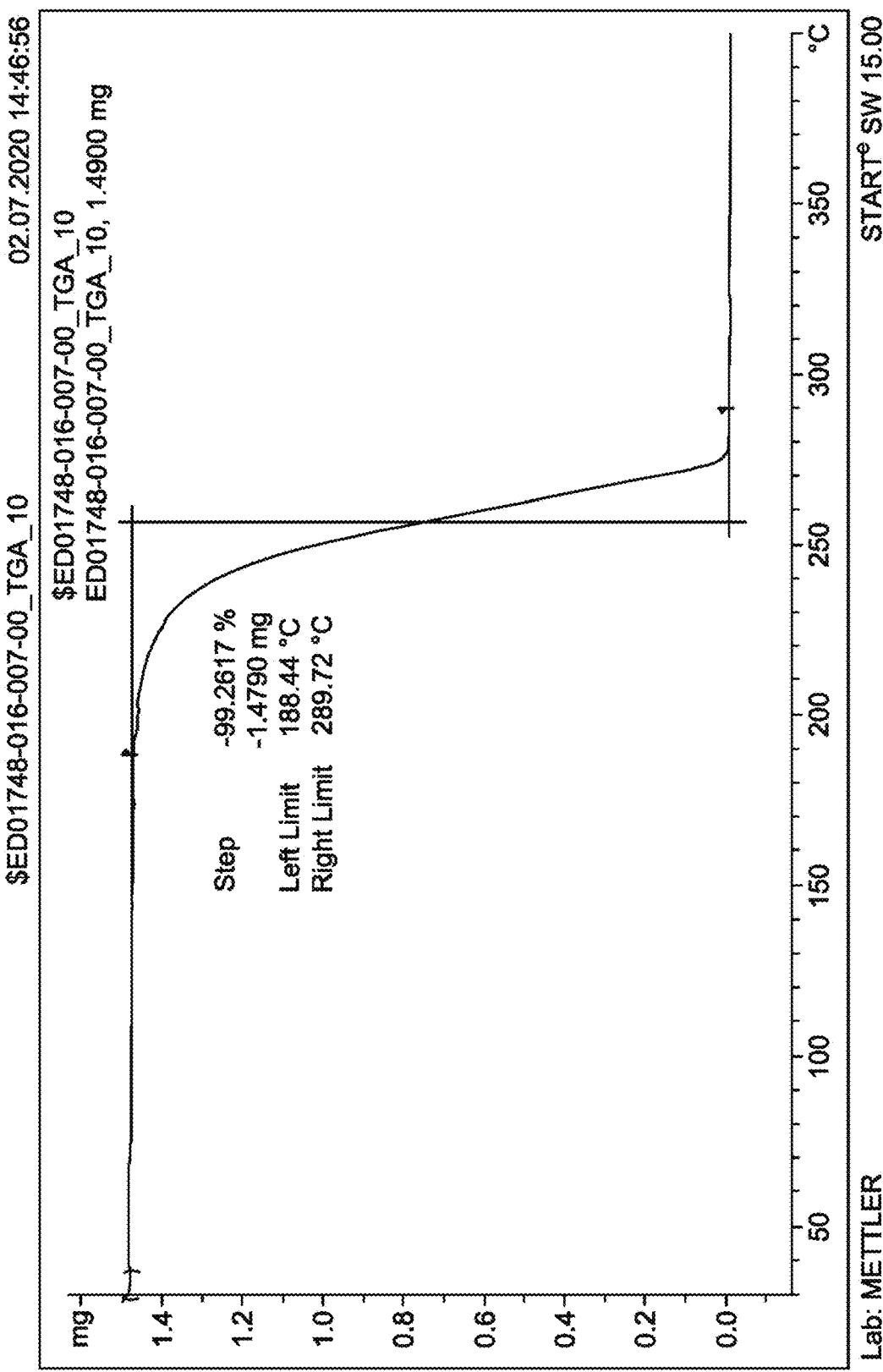
FIG. 26C shows a thermogravimetric analysis (TGA) thermogram of crystalline form Pattern 5 of Formula 1.

The XRPD pattern showed that Pattern 5 was crystalline (FIG. 26A and Table 10). DSC and TGA thermograms were obtained as shown in FIG. 26B and FIG. 26C. DSC shows an endothermic peak with an onset of 59° C. (very small), 81° C. and 89° C. TGA shows no significant mass loss until decomposition.

TABLE 10

XRPD Table of Pattern 5 of Formula 1

| Index | Caption | Angle 2 Theta ° | d Value Angstrom | Intensity Counts | Net Intensity | Rel. Intensity |
|---|---|---|---|---|---|---|
| 1 | 6.288° | 6.288 | 14.04477 | 410.9 | 294.4 | 26% |
| 2 | 6.591° | 6.591 | 13.40072 | 448.3 | 341.2 | 30% |
| 3 | 7.299° | 7.299 | 12.1017 | 173.5 | 84.7 | 8% |
| 4 | 7.669° | 7.669 | 11.5183 | 142.7 | 58.3 | 5% |
| 5 | 8.045° | 8.045 | 10.98169 | 208.1 | 127.0 | 11% |
| 6 | 8.396° | 8.396 | 10.52315 | 146.1 | 67.4 | 6% |
| 7 | 8.858° | 8.858 | 9.975244 | 801.7 | 727.4 | 65% |
| 8 | 9.427° | 9.427 | 9.374208 | 229.8 | 162.6 | 14% |
| 9 | 9.736° | 9.736 | 9.077063 | 281.1 | 218.7 | 19% |
| 10 | 9.972° | 9.972 | 8.863215 | 315.5 | 257.2 | 23% |
| 11 | 10.865° | 10.865 | 8.136434 | 907.7 | 853.5 | 76% |
| 12 | 11.198° | 11.198 | 7.895094 | 313.0 | 258.5 | 23% |
| 13 | 11.564° | 11.564 | 7.646404 | 304.3 | 250.4 | 22% |
| 14 | 12.017° | 12.017 | 7.358904 | 90.3 | 38.5 | 3% |
| 15 | 12.586° | 12.586 | 7.027328 | 129.6 | 76.3 | 7% |
| 16 | 13.178° | 13.178 | 6.713122 | 615.3 | 554.8 | 49% |
| 17 | 13.335° | 13.335 | 6.634624 | 973.3 | 911.3 | 81% |
| 18 | 13.818° | 13.818 | 6.403406 | 210.1 | 144.4 | 13% |
| 19 | 14.626° | 14.626 | 6.051351 | 317.6 | 249.7 | 22% |
| 20 | 15.112° | 15.112 | 5.857883 | 293.5 | 226.1 | 20% |
| 21 | 15.754° | 15.754 | 5.620764 | 1088.1 | 1021.3 | 91% |
| 22 | 16.152° | 16.152 | 5.483039 | 376.9 | 310.8 | 28% |
| 23 | 16.977° | 16.977 | 5.218423 | 464.4 | 394.2 | 35% |
| 24 | 17.462° | 17.462 | 5.074476 | 427.9 | 353.6 | 31% |
| 25 | 17.767° | 17.767 | 4.988079 | 1203.0 | 1126.9 | 100% |
| 26 | 18.970° | 18.970 | 4.674501 | 296.9 | 214.3 | 19% |
| 27 | 19.349° | 19.349 | 4.583826 | 408.7 | 325.5 | 29% |
| 28 | 19.797° | 19.797 | 4.48099 | 842.9 | 760.2 | 67% |
| 29 | 20.354° | 20.354 | 4.359617 | 180.5 | 100.5 | 9% |
| 30 | 20.925° | 20.925 | 4.241933 | 119.6 | 44.6 | 4% |
| 31 | 21.859° | 21.859 | 4.062715 | 151.2 | 83.0 | 7% |
| 32 | 22.232° | 22.232 | 3.995424 | 158.5 | 86.8 | 8% |
| 33 | 22.581° | 22.581 | 3.934432 | 128.7 | 54.8 | 5% |
| 34 | 23.104° | 23.104 | 3.84653 | 342.2 | 265.9 | 24% |
| 35 | 23.460° | 23.460 | 3.789058 | 254.7 | 177.5 | 16% |
| 36 | 23.776° | 23.776 | 3.739354 | 354.2 | 277.0 | 25% |
| 37 | 23.974° | 23.974 | 3.70888 | 352.6 | 275.8 | 24% |
| 38 | 24.573° | 24.573 | 3.619826 | 209.0 | 131.7 | 12% |
| 39 | 24.904° | 24.904 | 3.572441 | 210.4 | 131.1 | 12% |
| 40 | 25.158° | 25.158 | 3.536991 | 204.5 | 124.1 | 11% |
| 41 | 25.979° | 25.979 | 3.427044 | 250.5 | 168.7 | 15% |
| 42 | 26.546° | 26.546 | 3.355137 | 128.8 | 46.7 | 4% |
| 43 | 26.861° | 26.861 | 3.31641 | 161.0 | 79.3 | 7% |
| 44 | 27.092° | 27.092 | 3.288682 | 168.6 | 87.7 | 8% |
| 45 | 27.334° | 27.334 | 3.260165 | 111.3 | 31.7 | 3% |
| 46 | 27.666° | 27.666 | 3.221733 | 322.5 | 243.5 | 22% |
| 47 | 28.197° | 28.197 | 3.162233 | 409.9 | 330.5 | 29% |
| 48 | 28.860° | 28.860 | 3.091091 | 140.6 | 63.5 | 6% |
| 49 | 29.245° | 29.245 | 3.051331 | 229.9 | 155.4 | 14% |
| 50 | 29.532° | 29.532 | 3.022331 | 236.9 | 165.1 | 15% |
| 51 | 30.312° | 30.312 | 2.94627 | 251.0 | 184.4 | 16% |
| 52 | 30.712° | 30.712 | 2.908782 | 186.0 | 117.7 | 10% |
| 53 | 30.993° | 30.993 | 2.883035 | 125.7 | 58.4 | 5% |
| 54 | 31.796° | 31.796 | 2.812095 | 128.8 | 65.4 | 6% |
| 55 | 32.341° | 32.341 | 2.76595 | 99.8 | 40.9 | 4% |
| 56 | 32.971° | 32.971 | 2.71448 | 72.9 | 20.0 | 2% |
| 57 | 33.855° | 33.855 | 2.645633 | 69.3 | 20.7 | 2% |
| 58 | 36.055° | 36.055 | 2.489096 | 65.7 | 22.2 | 2% |
| 59 | 36.620° | 36.620 | 2.45197 | 72.5 | 29.6 | 3% |
| 60 | 38.414° | 38.414 | 2.341442 | 71.0 | 27.7 | 2% |
| 61 | 39.853° | 39.853 | 2.260157 | 62.5 | 22.2 | 2% |

Example 7

Synthesis and Characterization of Crystalline Form Pattern 6 Crystalline of 1-(2-chlorophenyl)-(S)-1-hydroxypropyl-(S)-2-carbamate 200 mg of Pattern 1 was placed into an open topped vial. This was placed in a drying pistol pre-heated to 110° C. and under ambient atmospheric conditions and heated at this temperature for 15 minutes. The molten material was then rapidly quench cooled by plunging into dry ice. The resultant glass was examined by optical microscopy and showed no evidence of crystalline material. This amorphous material was treated with toluene (4 mL) and shaken at room temperature. After 4 days solid had formed on the base of the vial. Pattern 6 was isolated by brief filtration under a stream of nitrogen (90.2% UPLC purity).

The XRPD pattern showed that Pattern 6 was crystalline (FIG. 27A and Table 11). DSC and TGA thermograms were also obtained for Pattern 6 of Formula 1 as shown in FIG. 27B and FIG. 27C, respectively. DSC shows an endothermic peak with an onset at 72° C. TGA shows 4.8% weight percent loss between 70-161° C.

TABLE 11

10.0 XRPD Table of Pattern 6 of Formula 1

| Index | Caption | Angle 2 Theta ° | d Value Angstrom | Intensity Counts | Net Intensity | Rel. Intensity |
|---|---|---|---|---|---|---|
| 1 | 6.629° | 6.629 | 13.32261 | 1734.8 | 1643.9 | 56% |
| 2 | 8.289° | 8.289 | 10.65854 | 1245.4 | 1179.0 | 40% |
| 3 | 8.974° | 8.974 | 9.846114 | 88.9 | 29.8 | 1% |
| 4 | 9.958° | 9.958 | 8.875217 | 1618.7 | 1559.6 | 53% |
| 5 | 11.980° | 11.980 | 7.381588 | 393.6 | 334.1 | 11% |
| 6 | 13.225° | 13.225 | 6.689138 | 219.7 | 158.7 | 5% |
| 7 | 14.131° | 14.131 | 6.262249 | 1632.7 | 1566.0 | 53% |
| 8 | 14.936° | 14.936 | 5.926644 | 397.7 | 331.5 | 11% |
| 9 | 15.982° | 15.982 | 5.540995 | 97.9 | 32.3 | 1% |
| 10 | 16.374° | 16.374 | 5.409378 | 3004.1 | 2935.9 | 100% |
| 11 | 16.576° | 16.576 | 5.343692 | 926.9 | 858.0 | 29% |
| 12 | 19.285° | 19.285 | 4.598821 | 1179.5 | 1104.8 | 38% |
| 13 | 19.882° | 19.882 | 4.462 | 1356.2 | 1279.8 | 44% |
| 14 | 20.529° | 20.529 | 4.32277 | 988.2 | 914.3 | 31% |
| 15 | 21.017° | 21.017 | 4.223648 | 262.5 | 193.6 | 7% |
| 16 | 21.878° | 21.878 | 4.059192 | 124.6 | 56.9 | 2% |
| 17 | 22.482° | 22.482 | 3.951522 | 604.4 | 531.4 | 18% |
| 18 | 22.836° | 22.836 | 3.891081 | 168.8 | 94.7 | 3% |
| 19 | 23.559° | 23.559 | 3.773296 | 349.5 | 277.3 | 9% |
| 20 | 24.023° | 24.023 | 3.701401 | 161.1 | 93.1 | 3% |
| 21 | 24.918° | 24.918 | 3.570469 | 259.2 | 191.7 | 7% |
| 22 | 25.072° | 25.072 | 3.548931 | 536.0 | 466.1 | 16% |
| 23 | 25.623° | 25.623 | 3.473757 | 801.2 | 725.0 | 25% |
| 24 | 25.921° | 25.921 | 3.434617 | 893.8 | 815.5 | 28% |
| 25 | 26.602° | 26.602 | 3.348142 | 225.8 | 145.8 | 5% |
| 26 | 27.003° | 27.003 | 3.299365 | 243.9 | 164.7 | 6% |
| 27 | 27.925° | 27.925 | 3.192473 | 213.0 | 130.8 | 4% |
| 28 | 28.422° | 28.422 | 3.137742 | 1298.1 | 1214.3 | 41% |
| 29 | 28.833° | 28.833 | 3.094014 | 164.6 | 81.6 | 3% |
| 30 | 29.659° | 29.659 | 3.009618 | 527.2 | 447.1 | 15% |
| 31 | 30.055° | 30.055 | 2.970896 | 147.0 | 68.4 | 2% |
| 32 | 30.715° | 30.715 | 2.908536 | 548.7 | 476.4 | 16% |
| 33 | 31.916° | 31.916 | 2.801745 | 151.6 | 86.9 | 3% |
| 34 | 32.328° | 32.328 | 2.767 | 278.5 | 212.6 | 7% |
| 35 | 33.070° | 33.070 | 2.706611 | 133.8 | 69.3 | 2% |
| 36 | 33.525° | 33.525 | 2.670882 | 131.6 | 70.5 | 2% |
| 37 | 33.783° | 33.783 | 2.651092 | 173.2 | 115.1 | 4% |
| 38 | 34.973° | 34.973 | 2.563588 | 145.7 | 84.9 | 3% |
| 39 | 35.716° | 35.716 | 2.511899 | 84.1 | 23.2 | 1% |
| 40 | 36.898° | 36.898 | 2.434115 | 136.8 | 74.1 | 3% |
| 41 | 38.265° | 38.265 | 2.350248 | 78.2 | 24.1 | 1% |
| 42 | 38.935° | 38.935 | 2.311308 | 86.8 | 32.1 | 1% |
| 43 | 39.979° | 39.979 | 2.253317 | 109.1 | 48.9 | 2% |

TABLE 11-continued 10.0 XRPD Table of Pattern 6 of Formula 1

| Index | Caption | Angle 2 Theta ° | d Value Angstrom | Intensity Counts | Net Intensity | Rel. Intensity |
|---|---|---|---|---|---|---|
| 44 | 40.371° | 40.371 | 2.232336 | 135.3 | 75.5 | 3% |
| 45 | 40.644° | 40.644 | 2.217998 | 144.6 | 86.0 | 3% |

Example 8

Solvent/Antisolvent Polymorph Screening for Pattern 1

TABLE A

| Exp. | Solvent | Volume/ul | Anti-Solvent | Volume/ul | Initial result | Notes | Result |
|---|---|---|---|---|---|---|---|
| 1 | 2-propanol | 60 | Toluene | 100 | Soluble | Shaken RT, refrigerated | Soluble |
| 2 | 2-propanol | 60 | Heptane | 200 | Soluble | Shaken RT, refrigerated | Soluble |
| 3 | 2-propanol | 60 | Diethyl ether | 100 | Soluble | Shaken RT, refrigerated | Soluble |
| 4 | 2-propanol | 60 | TBME | 200 | Soluble | Shaken RT, refrigerated, | Soluble |
| 5 | acetone | 60 | Toluene | 100 | Soluble | Shaken RT, refrigerated | Soluble |
| 6 | acetone | 60 | Heptane | 175 | Cloudy | oil | oil |
| 7 | acetone | 60 | Diethyl ether | 100 | Soluble | Shaken RT, refrigerated | Soluble |
| 8 | acetone | 60 | TBME | 100 | Soluble | Shaken RT, refrigerated | Soluble |
| 9 | chloroform | 60 | Toluene | 100 | Precipitate | Shaken RT, solid XRPD | Crystalline Pattern 9 No change on standing o/n |
| 10 | chloroform | 60 | Heptane | 25 | Precipitate | Shaken RT, solid XRPD | Crystalline Pattern 8 No change on standing o/n |
| 11 | chloroform | 60 | Diethyl ether | 100 | Soluble | Shaken RT, refrigerated | Soluble |
| 12 | chloroform | 60 | TBME | 100 | Soluble | Shaken RT, refrigerated | Soluble |
| 13 | DCM | 80 | Toluene | 100 | Precipitate | Shaken RT, solid XRPD | Crystalline Pattern 9 No change on standing o/n |
| 14 | DCM | 80 | Heptane | 50 | Precipitate | Shaken RT, solid XRPD | Crystalline Pattern 8 Small change on standing o/n |
| 14 | DCM | 80 | Diethyl ether | 100 | Soluble | Shaken RT, refrigerated, | Soluble |
| 16 | DCM | 80 | TBME | 100 | Soluble | Shaken RT, refrigerated | Soluble |
| 17 | ethyl acetate | 60 | Toluene | 100 | Soluble | Shaken RT, refrigerated | Soluble |
| 18 | ethyl acetate | 60 | Heptane | 100 | Cloudy | Oil, then solid formed | Crystalline Pattern 11 Change on standing (5 days) to mix P2 + P3 |
| 19 | ethyl acetate | 60 | Diethyl ether | 100 | Soluble | Shaken RT, refrigerated | Soluble |
| 20 | ethyl acetate | 60 | TBME | 100 | Soluble | Shaken RT, refrigerated | Soluble |
| 21 | ethyl acetate | 60 | Pentane | 225 | Cloudy | Oil | Oil |
| 22 | ethyl acetate | 60 | cyclohexane | 350 | Precipitate | Shaken RT, solid XRPD | Crystalline, P1 |

TABLE A-continued

| Exp. | Solvent | Volume/ul | Anti-Solvent | Volume/ul | Initial result | Notes | Result |
|---|---|---|---|---|---|---|---|
| 23 | ethyl acetate | 60 | methyl-cyclohexane | 325 | Precipitate | Shaken RT, solid XRPD | Crystalline, P1 |
| 24 | chloroform | 60 | Pentane | 75 | Precipitate | Shaken RT, solid XRPD | Crystalline P8, change on standing |
| 25 | chloroform | 60 | cyclohexane | 125 | Precipitate | Shaken RT, solid XRPD | Crystalline P7. Change on standing |
| 26 | chloroform | 60 | methyl-cyclohexane | 75 | Precipitate | Shaken RT, solid XRPD | Crystalline P7, No change on standing |
| 27 | DCM | 80 | Pentane | 100 | Precipitate | Shaken RT, solid XRPD | Crystalline P8. Change on standing |
| 28 | DCM | 80 | cyclohexane | 50 | Precipitate | Shaken RT, solid XRPD | Crystalline P7. No change on standing |
| 29 | DCM | 80 | methyl-cyclohexane | 50 | Precipitate | Shaken RT, solid XRPD | Crystalline P7. Change on standing |

Pattern 7 was obtained from DCM/cyclohexane, DCM/methylcyclohexane, CHCl$_3$/cyclohexane and CHCl$_3$/methylcyclohexane in the solvent/anti-solvent screening experiment described in Table A.

Figure 28B:
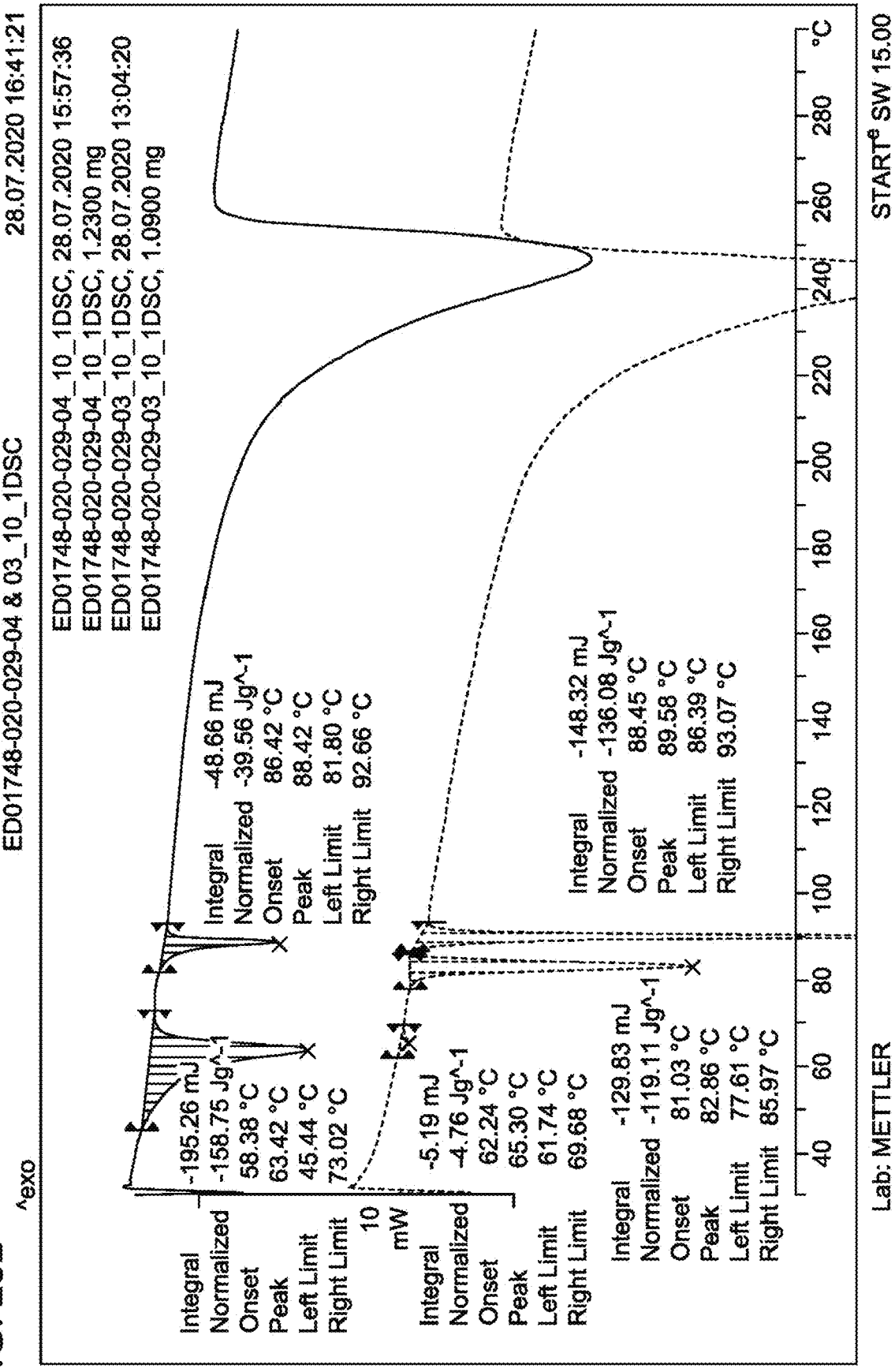
FIG. 28B shows a differential scanning calorimetry (DSC) thermogram of freshly isolated crystalline Pattern 7 of Formula 1 (comprising an endothermic peak with an onset at 58.4° C. and an onset at 86.4° C.) and a DSC overlay after standing for 5 days.
Figure 28C:
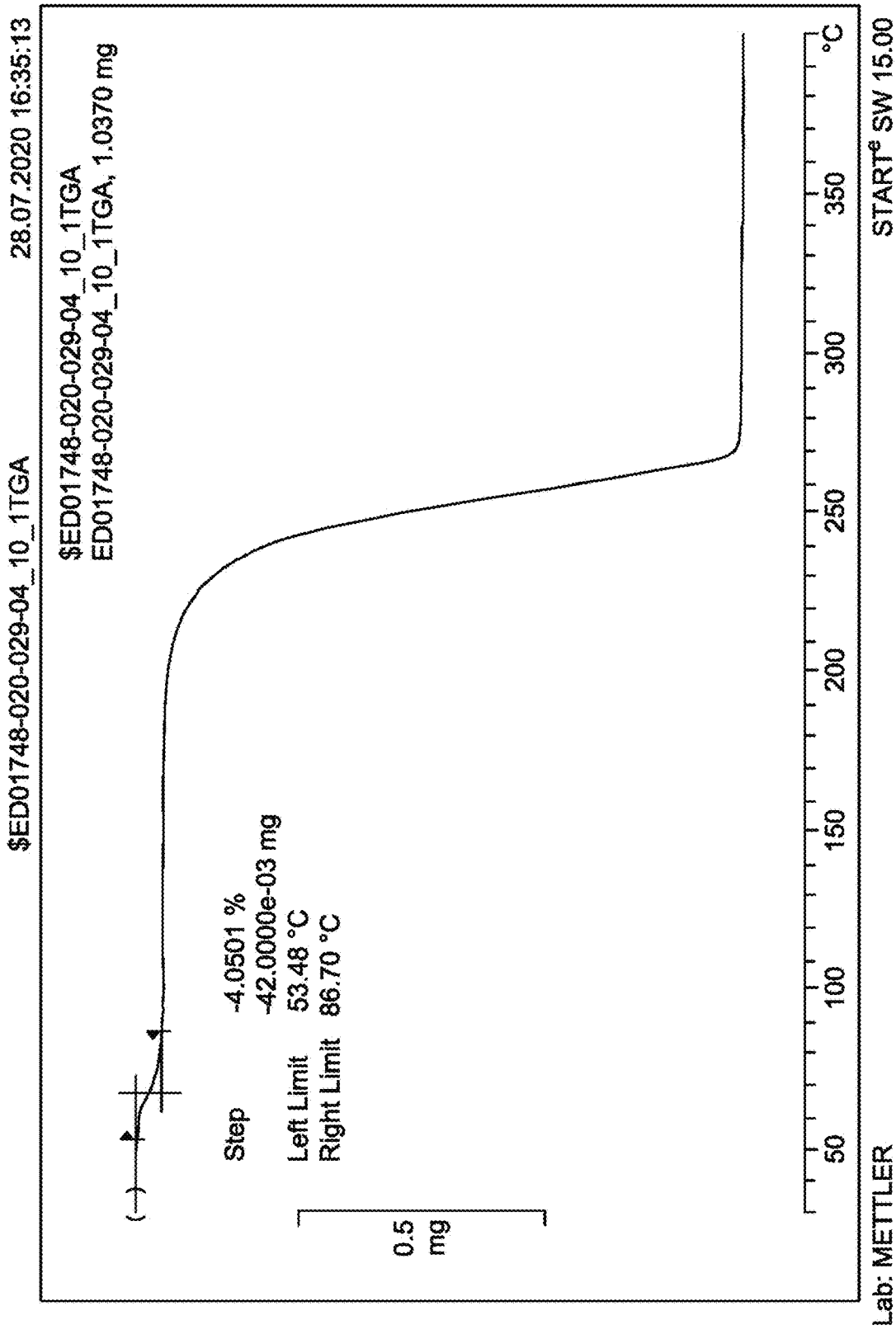
FIG. 28C shows a thermogravimetric analysis (TGA) thermogram of freshly isolated crystalline Pattern 7 of Formula 1.

The XRPD pattern for Pattern 7 is shown in FIG. 28A and Table 12. DSC and TGA thermograms were also obtained for Pattern 7 of Formula 1 as shown in FIG. 28B and FIG. 28C, respectively. DSC of freshly isolated Pattern 7 shows endothermic peaks with an onset at 58° C. and 86° C. The TGA shows about a 4% weight percent loss between about 54 and 87° C.

TABLE 12

XRPD Table of Pattern 7 of Formula 1

| Index | Caption | Angle 2 Theta ° | d Value Angstrom | Intensity Count | Net Intensity | Rel. Intensity |
|---|---|---|---|---|---|---|
| 1 | 6.678° | 6.678 | 13.22453 | 182.7 | 66.5 | 1% |
| 2 | 8.373° | 8.373 | 10.55194 | 119.9 | 55.3 | 1% |
| 3 | 9.048° | 9.048 | 9.765502 | 120.4 | 63.5 | 1% |
| 4 | 10.006° | 10.006 | 8.8328 | 6839.3 | 6771.9 | 100% |
| 5 | 11.869° | 11.869 | 7.450305 | 106.3 | 43.5 | 1% |
| 6 | 12.143° | 12.143 | 7.282938 | 89.9 | 30.1 | 0% |
| 7 | 13.535° | 13.535 | 6.536877 | 91.0 | 35.0 | 1% |
| 8 | 14.321° | 14.321 | 6.179873 | 142.5 | 74.9 | 1% |
| 9 | 14.994° | 14.994 | 5.903751 | 3424.6 | 3349.5 | 49% |
| 10 | 15.838° | 15.838 | 5.59096 | 106.2 | 29.4 | 0% |
| 11 | 16.273° | 16.273 | 5.442454 | 2107.7 | 2032.5 | 30% |
| 12 | 16.814° | 16.814 | 5.268797 | 146.1 | 77.3 | 1% |
| 13 | 19.351° | 19.351 | 4.583279 | 107.0 | 43.5 | 1% |
| 14 | 20.003° | 20.003 | 4.435391 | 1524.3 | 1453.1 | 21% |
| 15 | 20.958° | 20.958 | 4.23527 | 212.9 | 143.2 | 2% |
| 16 | 21.249° | 21.249 | 4.177896 | 494.3 | 428.1 | 6% |
| 17 | 23.005° | 23.005 | 3.862903 | 81.0 | 29.5 | 0% |
| 18 | 23.811° | 23.811 | 3.733878 | 84.2 | 34.3 | 1% |
| 19 | 24.320° | 24.32 | 3.656892 | 78.6 | 26.4 | 0% |
| 20 | 25.077° | 25.077 | 3.548254 | 541.4 | 477.8 | 7% |
| 21 | 25.813° | 25.813 | 3.448667 | 1087.2 | 1015.6 | 15% |
| 22 | 26.097° | 26.097 | 3.411779 | 139.2 | 66.8 | 1% |
| 23 | 26.683° | 26.683 | 3.338122 | 115.8 | 46.2 | 1% |
| 24 | 28.214° | 28.214 | 3.160371 | 310.1 | 243.1 | 4% |
| 25 | 28.742° | 28.742 | 3.103599 | 146.5 | 78.7 | 1% |
| 26 | 29.633° | 29.633 | 3.012272 | 112.5 | 39.8 | 1% |
| 27 | 30.173° | 30.173 | 2.959586 | 475.6 | 396.3 | 6% |
| 28 | 30.780° | 30.78 | 2.90252 | 378.1 | 297.3 | 4% |
| 29 | 31.075° | 31.075 | 2.875691 | 1796.1 | 1716.8 | 25% |
| 30 | 32.762° | 32.762 | 2.731355 | 106.3 | 38.9 | 1% |
| 31 | 33.382° | 33.382 | 2.682026 | 166.0 | 100.2 | 1% |

TABLE 12-continued

XRPD Table of Pattern 7 of Formula 1

| Index | Caption | Angle 2 Theta ° | d Value Angstrom | Intensity Count | Net Intensity | Rel. Intensity |
|---|---|---|---|---|---|---|
| 32 | 36.132° | 36.132 | 2.483912 | 98.8 | 48.0 | 1% |
| 33 | 37.587° | 37.587 | 2.391073 | 69.9 | 25.7 | 0% |
| 34 | 38.199° | 38.199 | 2.354154 | 98.4 | 52.7 | 1% |
| 35 | 40.267° | 40.267 | 2.237886 | 89.2 | 39.8 | 1% |
| 36 | 40.582° | 40.582 | 2.221247 | 238.9 | 189.0 | 3% |

Pattern 8 was obtained from DCM/heptane, DCM/pentane, CHCl$_3$/heptane and CHCl$_3$/pentane in the solvent/anti-solvent screening experiment described in Table A.

Figure 29B:
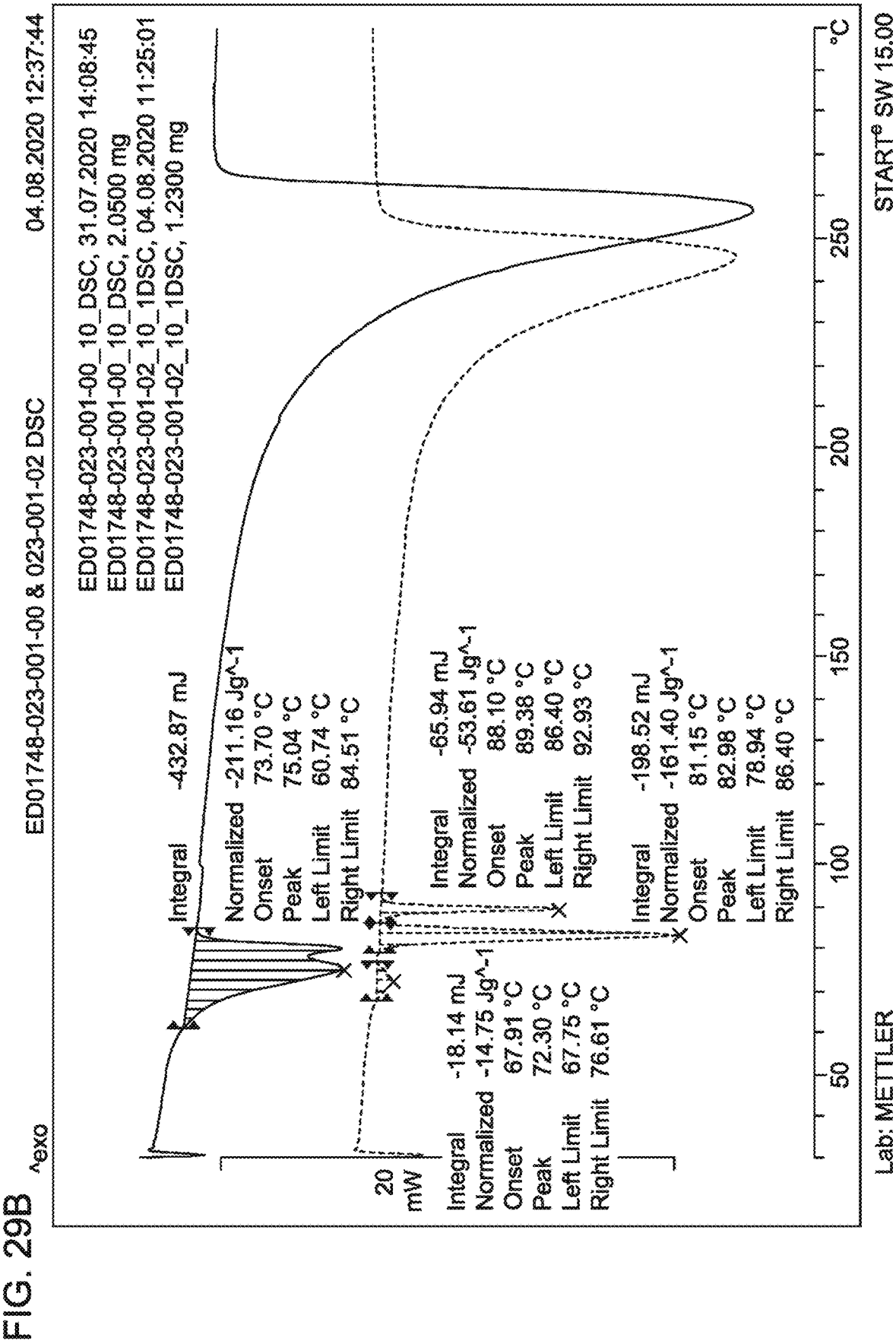
FIG. 29B shows a differential scanning calorimetry (DSC) thermogram of freshly isolated crystalline Pattern 8 of Formula 1 (comprising an endothermic peak with an onset at 74° C.) and a DSC overlay after standing for 4 days.
Figure 29C:
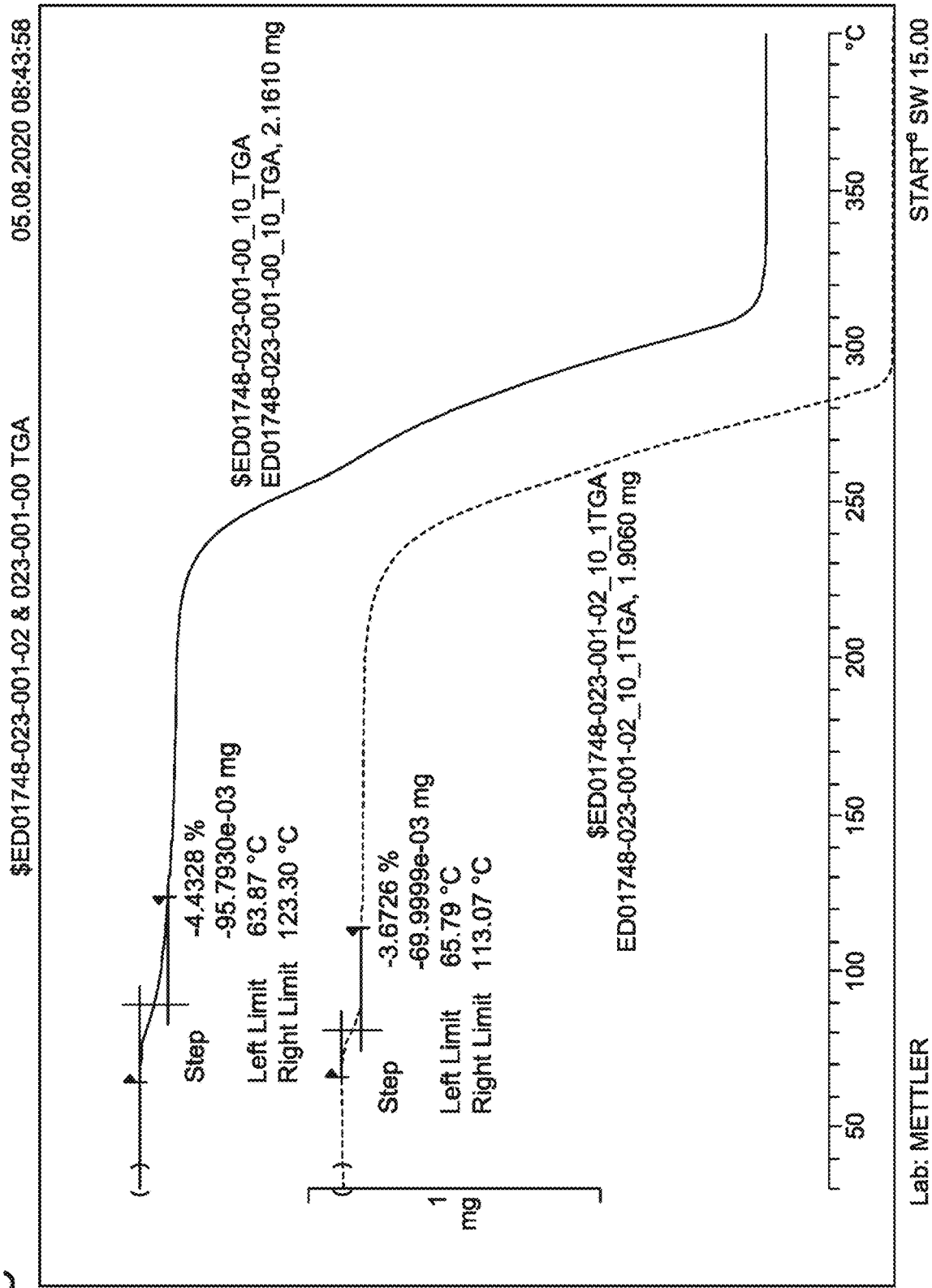
FIG. 29C shows a thermogravimetric analysis (TGA) thermogram of freshly isolated crystalline Pattern 8 of Formula 1 (exhibits an about 4.4% (wt %) loss between about 64° C. to about 123° C.) and a TGA overlay after standing for 4 days.

The XRPD pattern for Pattern 8 is shown in FIG. 29A and Table 13. Pattern 8 from chloroform and heptane was observed to change on standing. The thermal behaviour in the DSC was observed to change as shown in the DSC overlay in FIG. 29B. The material after standing for 4 days showed endothermic events of onset 68° C., 82° C. and 88° C. This is consistent with a mixture containing some Pattern 3. There seems to be some conversion to Pattern 1 in the DSC. The freshly isolated sample showed broader unresolved and overlapping endothermic events of onset 74° C. (between 61-85° C.) The TGA thermogram as seen in FIG. 29C of this freshly isolated material shows a 4.4% mass loss between 64-123° C. and the sample after standing shows a mass loss of 3.7% between 66-113° C. suggesting both are solvated or hydrated forms with some solvent being lost during the conversion.

TABLE 13

XRPD Table of Pattern 8 of Formula 1

| Index | Caption | Angle 2 Theta ° | d Value Angstrom | Intensity count | Net Intensity | Rel. Intensity |
|---|---|---|---|---|---|---|
| 1 | 6.610° | 6.61 | 13.36227 | 545.6 | 434.2 | 8% |
| 2 | 8.216° | 8.216 | 10.7535 | 208.5 | 142.6 | 3% |
| 3 | 8.450° | 8.45 | 10.45576 | 295.2 | 231.8 | 4% |
| 4 | 9.045° | 9.045 | 9.76876 | 111.2 | 54.4 | 1% |
| 5 | 10.005° | 10.005 | 8.833625 | 5412.0 | 5348.1 | 100% |
| 6 | 11.826° | 11.826 | 7.477503 | 149.6 | 85.1 | 2% |

TABLE 13-continued

XRPD Table of Pattern 8 of Formula 1

| Index | Caption | Angle 2 Theta ° | d Value Angstrom | Intensity count | Net Intensity | Rel. Intensity |
|---|---|---|---|---|---|---|
| 7 | 12.172° | 12.172 | 7.26558 | 119.6 | 60.5 | 1% |
| 8 | 13.262° | 13.262 | 6.670907 | 72.4 | 22.8 | 0% |
| 9 | 13.515° | 13.515 | 6.546331 | 79.6 | 28.6 | 1% |
| 10 | 14.039° | 14.039 | 6.303211 | 159.5 | 103.9 | 2% |
| 11 | 14.316° | 14.316 | 6.181698 | 269.1 | 209.6 | 4% |
| 12 | 14.990° | 14.99 | 5.905528 | 2329.1 | 2264.9 | 42% |
| 13 | 15.754° | 15.754 | 5.620678 | 126.3 | 60.9 | 1% |
| 14 | 16.235° | 16.235 | 5.455233 | 2573.6 | 2507.5 | 47% |
| 15 | 16.853° | 16.853 | 5.256468 | 263.7 | 201.7 | 4% |
| 16 | 19.307° | 19.307 | 4.593502 | 224.0 | 166.2 | 3% |
| 17 | 20.008° | 20.008 | 4.434152 | 955.7 | 889.5 | 17% |
| 18 | 20.476° | 20.476 | 4.334008 | 207.3 | 139.5 | 3% |
| 19 | 20.675° | 20.675 | 4.292601 | 177.8 | 110.4 | 2% |
| 20 | 20.927° | 20.927 | 4.241448 | 198.4 | 132.1 | 2% |
| 21 | 21.291° | 21.291 | 4.169857 | 508.5 | 445.7 | 8% |
| 22 | 22.460° | 22.46 | 3.955396 | 143.2 | 91.4 | 2% |
| 23 | 22.965° | 22.965 | 3.869515 | 98.6 | 48.6 | 1% |
| 24 | 23.714° | 23.714 | 3.749011 | 128.7 | 80.0 | 1% |
| 25 | 24.396° | 24.396 | 3.645681 | 110.6 | 55.7 | 1% |
| 26 | 25.107° | 25.107 | 3.544069 | 466.4 | 403.6 | 8% |
| 27 | 25.427° | 25.427 | 3.500138 | 212.6 | 146.6 | 3% |
| 28 | 25.787° | 25.787 | 3.452086 | 909.4 | 841.5 | 16% |
| 29 | 26.147° | 26.147 | 3.405425 | 150.6 | 82.8 | 2% |
| 30 | 26.603° | 26.603 | 3.348019 | 150.5 | 85.0 | 2% |
| 31 | 28.116° | 28.116 | 3.171172 | 449.8 | 387.6 | 7% |
| 32 | 28.783° | 28.783 | 3.099194 | 292.1 | 227.9 | 4% |
| 33 | 29.562° | 29.562 | 3.019279 | 152.5 | 84.9 | 2% |
| 34 | 29.934° | 29.934 | 2.982634 | 117.2 | 45.9 | 1% |
| 35 | 30.215° | 30.215 | 2.95548 | 267.6 | 194.9 | 4% |
| 36 | 30.766° | 30.766 | 2.903811 | 283.8 | 211.8 | 4% |
| 37 | 31.132° | 31.132 | 2.870564 | 1201.0 | 1131.8 | 21% |
| 38 | 32.199° | 32.199 | 2.777786 | 86.2 | 30.3 | 1% |
| 39 | 32.708° | 32.708 | 2.735745 | 181.7 | 123.1 | 2% |
| 40 | 33.088° | 33.088 | 2.705182 | 96.9 | 38.7 | 1% |
| 41 | 33.467° | 33.467 | 2.675392 | 166.3 | 109.7 | 2% |
| 42 | 33.978° | 33.978 | 2.636339 | 79.9 | 27.9 | 1% |
| 43 | 36.208° | 36.208 | 2.47891 | 107.5 | 60.1 | 1% |
| 44 | 37.547° | 37.547 | 2.393519 | 77.7 | 33.3 | 1% |
| 45 | 38.297° | 38.297 | 2.34836 | 102.0 | 57.4 | 1% |
| 46 | 40.070° | 40.07 | 2.248458 | 69.9 | 21.7 | 0% |
| 47 | 40.385° | 40.385 | 2.231636 | 141.0 | 92.0 | 2% |
| 48 | 40.623° | 40.623 | 2.219077 | 175.1 | 126.5 | 2% |

Pattern 9 was obtained from DCM/toluene, CHCl$_3$/toluene in the solvent/anti-solvent screening experiment described in Table A.

The XRPD pattern for Pattern 9 is shown in FIG. 30A. and Table 14. As shown in FIG. 30B DSC of Pattern 9 shows endothermic peaks with an onset at about 63° C., 81° C. and 88° C.

TABLE 14

XRPD Table of Pattern 9 of Formula 1

| Index | Caption | Angle 2 Theta ° | d Value Angstrom | Intensity Count | Net Intensity | Rel. Intensity |
|---|---|---|---|---|---|---|
| 1 | 6.690° | 6.690 | 13.20243 | 447.0 | 336.9 | 3% |
| 2 | 8.359° | 8.359 | 10.56867 | 561.9 | 495.3 | 4% |
| 3 | 9.078° | 9.078 | 9.733361 | 113.2 | 50.0 | 0% |
| 4 | 10.043° | 10.043 | 8.80074 | 5895.8 | 5816.4 | 51% |
| 5 | 12.013° | 12.013 | 7.361348 | 631.8 | 562.7 | 5% |
| 6 | 13.581° | 13.581 | 6.514763 | 88.8 | 32.7 | 0% |
| 7 | 14.219° | 14.219 | 6.223952 | 510.6 | 448.8 | 4% |
| 8 | 15.023° | 15.023 | 5.892425 | 1782.2 | 1712.4 | 15% |
| 9 | 16.413° | 16.413 | 5.396596 | 11448.0 | 11358.9 | 100% |
| 10 | 19.384° | 19.384 | 4.575548 | 122.6 | 49.8 | 0% |
| 11 | 20.015° | 20.015 | 4.432676 | 1098.1 | 1020.8 | 9% |
| 12 | 20.592° | 20.592 | 4.309692 | 261.1 | 187.0 | 2% |
| 13 | 21.104° | 21.104 | 4.206413 | 840.4 | 775.2 | 7% |
| 14 | 22.538° | 22.538 | 3.941785 | 101.1 | 48.7 | 0% |

TABLE 14-continued

XRPD Table of Pattern 9 of Formula 1

| Index | Caption | Angle 2 Theta ° | d Value Angstrom | Intensity Count | Net Intensity | Rel. Intensity |
|---|---|---|---|---|---|---|
| 15 | 23.370° | 23.370 | 3.803311 | 100.2 | 50.2 | 0% |
| 16 | 24.040° | 24.040 | 3.698828 | 308.1 | 259.4 | 2% |
| 17 | 25.083° | 25.083 | 3.547366 | 477.5 | 408.7 | 4% |
| 18 | 25.940° | 25.940 | 3.432096 | 4235.7 | 4151.4 | 37% |
| 19 | 26.663° | 26.663 | 3.340634 | 131.9 | 46.9 | 0% |
| 20 | 27.095° | 27.095 | 3.288367 | 107.4 | 27.2 | 0% |
| 21 | 28.406° | 28.406 | 3.139458 | 2206.7 | 2123.6 | 19% |
| 22 | 29.004° | 29.004 | 3.076145 | 110.6 | 34.7 | 0% |
| 23 | 29.727° | 29.727 | 3.002909 | 164.5 | 84.5 | 1% |
| 24 | 30.173° | 30.173 | 2.959532 | 461.7 | 379.1 | 3% |
| 25 | 30.917° | 30.917 | 2.889966 | 1522.0 | 1444.7 | 13% |
| 26 | 32.296° | 32.296 | 2.769679 | 101.4 | 35.7 | 0% |
| 27 | 33.041° | 33.041 | 2.708896 | 461.8 | 397.1 | 3% |
| 28 | 33.493° | 33.493 | 2.67334 | 171.6 | 108.0 | 1% |
| 29 | 33.908° | 33.908 | 2.641598 | 104.5 | 45.9 | 0% |
| 30 | 35.034° | 35.034 | 2.559219 | 106.5 | 51.0 | 0% |
| 31 | 36.364° | 36.364 | 2.468625 | 134.9 | 81.3 | 1% |
| 32 | 36.819° | 36.819 | 2.439171 | 147.1 | 94.6 | 1% |
| 33 | 37.862° | 37.862 | 2.374294 | 103.1 | 52.3 | 0% |
| 34 | 40.625° | 40.625 | 2.219007 | 331.5 | 274.1 | 2% |
| 35 | 40.793° | 40.793 | 2.210219 | 289.1 | 232.0 | 2% |

Pattern 8 was obtained from DCM/heptane, DCM/pentane, CHCl$_3$/heptane and CHCl$_3$/pentane in the solvent/anti-solvent screening experiment described in Table A.

Pattern 7 and Pattern 8 are similar in showing variable behaviour on standing.

The XRPD pattern for Pattern 8 is shown in FIG. 29A. As shown in FIG. 29B DSC of freshly isolated crystalline Pattern 8 of Formula 1 exhibits an endothermic peak with an onset at 74° C.). As shown in the TGA of freshly isolated crystalline Pattern 8 of Formula 1 exhibits an about 4.4% (wt %) loss between about 64° C. to about 123° C.

Example 9

Synthesis and Characterization of Crystalline Form Pattern 10 Crystalline of 1-(2-chlorophenyl)-(S)-1-hydroxypropyl-(S)-2-carbamate 300 mg of Pattern 1 was placed into an open topped vial. This was placed in a drying pistol pre-heated to 110° C. and under ambient atmospheric conditions and heated at this temperature for 15 minutes. The molten material was then rapidly quench cooled by plunging into dry ice. The resultant glass was examined by optical microscopy and showed no evidence of crystalline material. This amorphous material was treated with acetonitrile (1.5 mL) to give a solution, shaken at room temperature for 30 minutes, refrigerated for 3 days and then allowed to evaporate at room temperature overnight under ambient conditions. XRPD analysis of the resulting crystalline form was consistent with Pattern 1 together with some extra peaks. These extra peaks were no longer evident upon reanalysis of the sample after standing overnight on the XRPD disc. This behavior is indicative of the presence of another albeit transient Pattern which is potentially an acetonitrile solvate.

The remainder of the material was treated with acetonitrile (1 mL) and the slurry shaken at room temperature overnight. A portion of this material was removed and analyzed rapidly by XRPD (FIG. 31A and Table 15). It showed the formation of a new Pattern, designated Pattern 10, which corresponds to the extra peaks observed in the initial scale up sample, together with some Pattern 1.

TABLE 15

XRPD Table of Pattern 10 of Formula 1

| Index | Caption | Angle 2 Theta ° | d Value Angstrom | Intensity Count | Net Intensity | Rel. Intensity |
|---|---|---|---|---|---|---|
| 1 | 7.389° | 7.389 | 11.95375 | 184.4 | 114.6 | 4% |
| 2 | 11.906° | 11.906 | 7.427009 | 1394.0 | 1335.8 | 52% |
| 3 | 12.623° | 12.623 | 7.007071 | 144.7 | 79.9 | 3% |
| 4 | 13.441° | 13.441 | 6.582259 | 1202.3 | 1128.0 | 44% |
| 5 | 14.140° | 14.140 | 6.258653 | 722.6 | 642.0 | 25% |
| 6 | 14.657° | 14.657 | 6.038925 | 1494.0 | 1410.5 | 55% |
| 7 | 15.760° | 15.760 | 5.618697 | 221.7 | 139.2 | 5% |
| 8 | 16.554° | 16.554 | 5.350962 | 821.4 | 741.0 | 29% |
| 9 | 16.885° | 16.885 | 5.246759 | 220.8 | 142.6 | 6% |
| 10 | 18.493° | 18.493 | 4.793934 | 283.5 | 208.7 | 8% |
| 11 | 18.979° | 18.979 | 4.672309 | 154.1 | 75.9 | 3% |
| 12 | 19.826° | 19.826 | 4.474541 | 155.6 | 74.5 | 3% |
| 13 | 21.512° | 21.512 | 4.127553 | 157.9 | 75.3 | 3% |
| 14 | 22.118° | 22.118 | 4.01574 | 490.1 | 401.1 | 16% |
| 15 | 22.549° | 22.549 | 3.940006 | 691.3 | 596.8 | 23% |
| 16 | 22.801° | 22.801 | 3.897017 | 338.4 | 241.5 | 9% |
| 17 | 23.734° | 23.734 | 3.74581 | 261.9 | 150.4 | 6% |
| 18 | 24.445° | 24.445 | 3.638554 | 398.4 | 277.0 | 11% |
| 19 | 24.706° | 24.706 | 3.600659 | 2625.0 | 2501.3 | 98% |
| 20 | 25.135° | 25.135 | 3.540104 | 492.8 | 366.8 | 14% |
| 21 | 25.877° | 25.877 | 3.440297 | 227.2 | 101.9 | 4% |
| 22 | 26.587° | 26.587 | 3.349975 | 261.7 | 140.7 | 6% |
| 23 | 26.909° | 26.909 | 3.310645 | 2665.4 | 2547.2 | 100% |
| 24 | 28.049° | 28.049 | 3.178655 | 141.4 | 33.8 | 1% |
| 25 | 28.362° | 28.362 | 3.144217 | 285.3 | 179.2 | 7% |
| 26 | 29.105° | 29.105 | 3.065613 | 211.5 | 112.0 | 4% |
| 27 | 29.416° | 29.416 | 3.034005 | 1207.0 | 1111.4 | 44% |
| 28 | 31.619° | 31.619 | 2.827397 | 232.2 | 158.3 | 6% |
| 29 | 33.924° | 33.924 | 2.64037 | 119.6 | 55.8 | 2% |
| 30 | 35.423° | 35.423 | 2.532039 | 100.6 | 36.5 | 1% |
| 31 | 35.799° | 35.799 | 2.506281 | 197.6 | 134.5 | 5% |
| 32 | 36.939° | 36.939 | 2.431494 | 298.0 | 235.8 | 9% |
| 33 | 37.329° | 37.329 | 2.407008 | 122.7 | 61.9 | 2% |
| 34 | 38.836° | 38.836 | 2.316971 | 389.7 | 324.1 | 13% |
| 35 | 40.400° | 40.400 | 2.230819 | 184.8 | 118.4 | 5% |

Example 10

Synthesis and Characterization of Crystalline Form Pattern 11 Crystalline of 1-(2-chlorophenyl)-(S)-1-hydroxypropyl-(S)-2-carbamate A portion of Pattern 1 (300 mg) was dissolved in ethyl acetate (1 mL) and then heptane (1.75 mL) was added portion wise until the mixture remained cloudy. An oily layer formed at the base of the vial. The mixture was shaken overnight at room temperature and then transferred to the fridge. A solid formed after refrigeration overnight, this partially converted to an oil on warming to room temperature. The mixture was shaken for a further 4 days at room temperature and then a small portion was removed. The material was isolated by filtration and dried very briefly under suction under a stream of nitrogen to give Pattern 11 (129 mg, 43%, 98.2% UPLC purity) (FIG. 32A and Table 16). As seen in FIG. 32B DSC shows a broad endothermic event of onset 70° C. and a sharper endothermic event of onset 89° C., followed by decomposition above ca. 200° C. and the TGA as seen in FIG. 32C shows 3.2% mass loss between 73-112° C. and decomposition above ca. 210° C.

TABLE 16

XRPD Table of Pattern 11 of Formula 1

| Index | Caption | Angle 2 Theta ° | d Value Angstrom | Intensity Count | Net Intensity | Rel. Intensity |
|---|---|---|---|---|---|---|
| 1 | 6.620° | 6.620 | 13.34176 | 1016.6 | 925.4 | 13% |
| 2 | 8.177° | 8.177 | 10.80347 | 665.7 | 602.0 | 8% |
| 3 | 8.425° | 8.425 | 10.48684 | 890.6 | 829.2 | 11% |
| 4 | 9.027° | 9.027 | 9.788087 | 105.0 | 50.0 | 1% |
| 5 | 10.035° | 10.035 | 8.807858 | 7395.6 | 7331.0 | 100% |
| 6 | 11.223° | 11.223 | 7.877846 | 123.2 | 57.9 | 1% |
| 7 | 11.582° | 11.582 | 7.634374 | 126.1 | 62.6 | 1% |
| 8 | 11.844° | 11.844 | 7.466004 | 484.6 | 422.1 | 6% |
| 9 | 12.184° | 12.184 | 7.258508 | 121.0 | 61.6 | 1% |
| 10 | 13.245° | 13.245 | 6.679463 | 221.8 | 165.3 | 2% |
| 11 | 13.988° | 13.988 | 6.325925 | 523.4 | 463.7 | 6% |
| 12 | 14.278° | 14.278 | 6.19823 | 648.2 | 585.8 | 8% |
| 13 | 14.667° | 14.667 | 6.034783 | 194.4 | 130.8 | 2% |
| 14 | 15.058° | 15.058 | 5.878963 | 2336.2 | 2274.0 | 31% |
| 15 | 16.037° | 16.037 | 5.522059 | 114.7 | 51.7 | 1% |
| 16 | 16.255° | 16.255 | 5.448413 | 6312.3 | 6247.8 | 85% |
| 17 | 16.856° | 16.856 | 5.255625 | 623.8 | 559.3 | 8% |
| 18 | 19.299° | 19.299 | 4.595383 | 132.5 | 71.7 | 1% |
| 19 | 19.858° | 19.858 | 4.467473 | 744.0 | 677.6 | 9% |
| 20 | 20.104° | 20.104 | 4.413284 | 755.5 | 688.1 | 9% |
| 21 | 20.380° | 20.380 | 4.354177 | 258.6 | 191.3 | 3% |
| 22 | 20.640° | 20.640 | 4.299832 | 354.9 | 289.0 | 4% |
| 23 | 20.975° | 20.975 | 4.231889 | 334.6 | 272.2 | 4% |
| 24 | 21.373° | 21.373 | 4.153932 | 774.4 | 718.7 | 10% |
| 25 | 22.565° | 22.565 | 3.937201 | 125.1 | 76.6 | 1% |
| 26 | 23.364° | 23.364 | 3.804388 | 69.2 | 19.6 | 0% |
| 27 | 23.755° | 23.755 | 3.742612 | 127.0 | 78.6 | 1% |
| 28 | 24.474° | 24.474 | 3.634304 | 216.8 | 169.1 | 2% |
| 29 | 25.259° | 25.259 | 3.522996 | 315.4 | 261.7 | 4% |
| 30 | 25.376° | 25.376 | 3.507006 | 500.1 | 444.9 | 6% |
| 31 | 25.856° | 25.856 | 3.443025 | 1772.6 | 1714.0 | 23% |
| 32 | 26.567° | 26.567 | 3.352454 | 173.8 | 115.6 | 2% |
| 33 | 26.976° | 26.976 | 3.302539 | 89.8 | 33.3 | 0% |
| 34 | 27.918° | 27.918 | 3.193248 | 288.2 | 230.5 | 3% |
| 35 | 28.150° | 28.150 | 3.167504 | 995.6 | 936.2 | 13% |
| 36 | 28.802° | 28.802 | 3.09726 | 433.8 | 374.7 | 5% |
| 37 | 29.633° | 29.633 | 3.012211 | 114.1 | 58.5 | 1% |
| 38 | 29.949° | 29.949 | 2.981133 | 114.7 | 54.9 | 1% |
| 39 | 30.224° | 30.224 | 2.954659 | 340.1 | 278.1 | 4% |
| 40 | 30.852° | 30.852 | 2.895901 | 513.9 | 451.7 | 6% |
| 41 | 31.270° | 31.270 | 2.858193 | 926.8 | 868.2 | 12% |
| 42 | 31.666° | 31.666 | 2.823337 | 75.1 | 22.8 | 0% |
| 43 | 32.347° | 32.347 | 2.765421 | 104.7 | 53.9 | 1% |
| 44 | 32.793° | 32.793 | 2.728863 | 250.1 | 197.1 | 3% |
| 45 | 33.581° | 33.581 | 2.666601 | 216.7 | 166.3 | 2% |
| 46 | 34.603° | 34.603 | 2.590146 | 93.9 | 55.8 | 1% |
| 47 | 35.553° | 35.553 | 2.523069 | 64.7 | 26.0 | 0% |
| 48 | 36.372° | 36.372 | 2.468097 | 105.3 | 64.0 | 1% |
| 49 | 37.502° | 37.502 | 2.396295 | 91.9 | 51.8 | 1% |
| 50 | 38.431° | 38.431 | 2.340469 | 99.6 | 58.0 | 1% |
| 51 | 40.116° | 40.116 | 2.24595 | 84.7 | 41.1 | 1% |
| 52 | 40.426° | 40.426 | 2.229457 | 156.8 | 112.5 | 2% |
| 53 | 40.800° | 40.800 | 2.209896 | 176.4 | 133.4 | 2% |
| 54 | 41.377° | 41.377 | 2.180372 | 76.1 | 34.7 | 0% |

In the above, the present invention was described with reference to examples. It will be understood by those of ordinary skill in the art that the present invention can be implemented in modified forms without departing from the essential features of the present invention. Therefore, the disclosed embodiments should be considered in a descriptive sense, rather than a limiting sense. The scope of the present invention is shown in the claims rather than the foregoing description, and all differences within the equivalent range thereto will be construed as being included in the present invention.

EMBODIMENTS

Embodiment 1

A crystalline form of (1-(2-chlorophenyl)-(S)-1-hydroxypropyl-(S)-2-carbamate having peaks of a X-ray powder diffraction pattern at a diffraction angle (2θ) of 6.662°, 8.153°, 9.801°, 11.303°, 11.660°, 13.280°, 13.435°, 14.703°, 16.243°, 16.948°, 19.091°, 19.419°, 20.443°, 21.124°, 24.202°, 24.619°, 28.998° and 31.697°.

Embodiment 2

The crystalline form of embodiment 1, which has additional peak(s) of the X-ray powder diffraction pattern at one or more diffraction angles (2θ) of 7.392°, 12.068°, 12.874°, 13.913°, 15.256°, 17.796°, 18.266°, 18.572°, 19.895°, 22.076°, 22.354°, 22.673°, 23.174°, 23.582°, 25.260°, 25.435°, 25.932°, 26.138°, 26.614°, 26.983°, 27.965°, 28.256°, 28.805°, 29.319°, 29.690°, 30.247°, 30.483°, 32.668° and 33.414°.

Embodiment 3

The crystalline form of embodiment 1, wherein the (1-(2-chlorophenyl)-(S)-1-hydroxypropyl-(S)-2-carbamate is a compound represented by Formula 1 below.

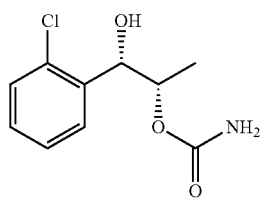

[Formula 1]

Embodiment 4

The crystalline form of embodiment 1, which has an endothermic peak at 89 to 90° C. in measurement by differential scanning calorimetry (DSC).

Embodiment 5

A method of preparing the crystalline form of (1-(2-chlorophenyl)-(S)-1-hydroxypropyl-(S)-2-carbamate of embodiment 1, comprising:
  forming an amorphous form by treating (1-(2-chlorophenyl)-(S)-1-hydroxypropyl-(S)-2-carbamate with one or more solvents selected from the group consisting of 1,4-dioxane, t-butanol, dichloromethane, water, and a mixed solvent thereof; and
  treating the resulting amorphous form with a solvent or a mixed solvent thereof, selected from the group consisting of acetone, chloroform, methanol (MeOH), tetrahydrofuran, diisopropyl ether, ethanol (EtOH), methyl ethyl ketone, acetonitrile, 2-propanol, tert-butanol, 1,2-dimethoxyethane (DME), 1-propanol, 2-butanol, water, 1,4-dioxane, 2-methyl-1-propanol, 2-methoxyethanol, butyl acetate, methyl butyl ketone, 3-methyl-1-butanol, 1-pentanol, cumene and anisole.

Embodiment 6

The method of embodiment 5, wherein the forming of an amorphous form comprises removing a solvent by rapid cooling, freeze drying or vacuum after (1-(2-chlorophenyl)-(S)-1-hydroxypropyl-(S)-2-carbamate is dissolved in the solvent.

Embodiment 7

A pharmaceutical composition comprising the crystalline form of (1-(2-chlorophenyl)-(S)-1-hydroxypropyl-(S)-2-carbamate of embodiment 1, for preventing or treating a disease selected from the group consisting of muscle relaxation, spasticity, spasms, central nervous system disorders, Lou Gehrig's disease, multiple sclerosis, pain, stroke, epilepsy, epilepsy-related syndrome, pediatric epilepsy, pediatric epilepsy-related syndrome, memory loss-related disease, nerve gas-induced disease, psychiatric disorder, movement disorder and neurological injury disease.

Embodiment 8

A pharmaceutical composition of embodiment 7, wherein the memory loss-related disease comprising senile dementia or Alzheimer's disease;
  wherein the nerve gas-induced disease comprising spasm, gastrointestinal distress, emesis, rhinorrhea, miosis, bronchoconstriction, fasciculation, floppy paralysis, apnea, diaphoresis and diarrhea;
  wherein the psychiatric disorder comprising depressive, bipolar disorders, anxiety disorder and seizures;
  wherein the movement disorder comprising ataxia, corticobasal ganglionic degeneration (CBGD), dyskinesia, dystonia, tremors, essential tremor, Parkinsonian tremor, hereditary spastic paraplegia, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), hemibalismus, hemi-facial spasm, Wilson's disease, stiff man syndrome, akinetic mutism, psychomotor retardation, painful legs moving toes syndrome, a gait disorder, and a drug-induced movement disorder;
  wherein the neurological injury disease comprising neurodegenerative disease, autism spectrum disease and prion diseases;
  the neurodegenerative disease is selected from the group consisting of Huntington's disease, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease, spinocerebellar ataxia, olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy and familial dysautonomia;
  the autism spectrum disease is selected from the group consisting of autism, Asperger syndrome and pervasive developmental disorder not otherwise specified (PDD-NOS); and the prion diseases is selected from the group consisting of Creutzfeldt-Jakob disease, Gerstmann-Straussler-Scheinker disease, Kuru disease and fatal familial insomnia.

Embodiment 9

A pharmaceutical composition comprising the crystalline form of (1-(2-chlorophenyl)-(S)-1-hydroxypropyl-(S)-2-carbamate of embodiment 1, for preventing or treating a disease selected from the group consisting of muscle relaxation, movement disorder, spasticity, spasms, epilepsy, epilepsy-related syndrome, central nervous system disorders, Lou Gehring's disease, multiple sclerosis, chronic pain, anxiety disorder, seizures, autism, depression, bipolar disorder, senile dementia or Alzheimer's and stroke.

Embodiments

1. A crystalline form of the compound of Formula 1:

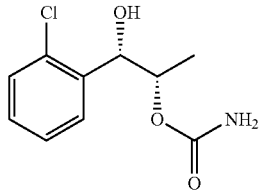

(1)

having an X-ray powder diffraction (XRPD) pattern comprising peaks at 13.3±0.2, 13.4±0.2, and 16.2±0.2 °2θ.

2. The crystalline form of embodiment 1, wherein the XRPD pattern further comprises peaks at 11.7±0.2 and 14.7±0.2 °2θ.

3. The crystalline form of embodiment 1 or 2, wherein the XRPD pattern further comprises peaks at 11.3±0.2 and 17.0±0.2 °2θ.

4. The crystalline form of any one of embodiments 1-3, wherein the XRPD pattern further comprises at least one peak at 6.7±0.2, 8.2±0.2, 9.8±0.2, 13.9±0.2, 19.1±0.2, 19.4±0.2, 24.6±0.2, or 27.0±0.2 °2θ.

5. The crystalline form of any one of embodiments 1-4, wherein the XRPD pattern is substantially similar to the XRPD pattern of FIG. 10.

6. The crystalline form of any one of embodiments 1-5, wherein the crystalline form exhibits an about 5% (wt %) loss between about 39° C. to about 237° C. as determined by thermogravimetric analysis (TGA).

7. The crystalline form of any one of embodiments 1-6, wherein the crystalline form exhibits:
   a) a DSC thermogram that is substantially similar to the DSC thermogram of FIG. 14; or
   b) a TGA thermogram that is substantially similar to the TGA thermogram of FIG. 15.

8. A crystalline form of the compound of Formula 1:

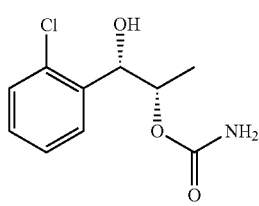

(1)

having an X-ray powder diffraction (XRPD) pattern comprising peaks at 16.3±0.2, 19.3±0.2, and 20.6±0.2 °2θ.

9. The crystalline form of embodiment 8, wherein the XRPD pattern further comprises peaks at 19.8±0.2 or 25.8±0.2 °2θ.

10. The crystalline form of embodiment 8 or 9, wherein the XRPD pattern further comprises peaks at 14.3±0.2 and 25.5±0.2 °2θ.

11. The crystalline form of any one of embodiments 8-10, wherein the XRPD pattern further comprises at least one peak at 6.7±0.2, 10.0±0.2, 14.0±0.2, 22.4±0.2, 25.2±0.2, 28.1±0.2, or 28.6±0.2 °2θ.

12. The crystalline form of any one of embodiments 8-11, wherein the XRPD pattern further comprises at least one peak at 8.2±0.2, 8.4±0.2, 12.9±0.2, 13.2±0.2, 14.6±0.2, 16.8±0.2, 22.0±0.2, 23.0±0.2, 23.7±0.2, 26.2±0.2, 27.0±0.2, 31.7±0.2, 34.6±0.2, 35.6±0.2, 36.0±0.2, 37.3±0.2, 38.6±0.2, or 40.1±0.2 °2θ.

13. The crystalline form of any one of embodiments 8-12, wherein the crystalline form exhibits an XRPD pattern comprising the peaks listed in Table 7.

14. The crystalline form of any one of embodiments 8-13, which exhibits an XRPD that is substantially similar to FIG. 23A.

15. The crystalline form of any one of embodiments 8-14, wherein the crystalline form exhibits a differential scanning calorimetry (DSC) thermogram comprising an endothermic peak with an onset at about 49° C.

16. The crystalline form of any one of embodiments 8-15, wherein the crystalline form exhibits an about 9% (wt %) loss between about 58° C. to about 191° C. as determined by thermogravimetric analysis (TGA).

17. The crystalline form of any one of embodiments 8-16, wherein the crystalline form exhibits:
   a) a DSC thermogram that is substantially similar to the DSC thermogram of FIG. 23B; or
   b) a TGA thermogram that is substantially similar to the TGA thermogram of FIG. 23C.

18. A crystalline form of the compound of Formula 1:

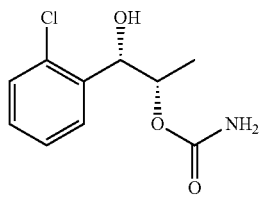

(1)

having an X-ray powder diffraction (XRPD) pattern comprising peaks at 10.9±0.2, 15.8±0.2, and 17.8±0.2 °2θ.

19. The crystalline form of embodiment 18, wherein the XRPD pattern further comprises peaks at 8.9±0.2 and 13.4±0.2 °2θ.

20. The crystalline form of embodiment 18 or 19, wherein the XRPD pattern further comprises peaks at 17.0±0.2 and 17.5±0.2 °2θ.

21. The crystalline form of any one of embodiments 18-20, wherein the XRPD pattern further comprises at least one peak at 15.2±0.2, 19.8±0.2, 23.2±0.2, 24.0±0.2, 28.2±0.2, 30.4±0.2, or 30.8±0.2 °2θ.

22. The crystalline form of any one of embodiments 18-21, wherein the crystalline form exhibits an XRPD pattern comprising the peaks listed in Table 8.

23. The crystalline form of any one of embodiments 18-22, wherein the crystalline form exhibits an XRPD pattern that is substantially similar to the XRPD pattern of FIG. 24A.

24. The crystalline form of any one of embodiments 18-23, wherein the crystalline form exhibits a differential scanning calorimetry (DSC) thermogram comprising an endothermic peak with an onset at about 82° C.

25. The crystalline form of any one of embodiments 18-24, wherein the crystalline form exhibits:
  a) a DSC thermogram that is substantially similar to the DSC thermogram of FIG. 24B; or
  b) a TGA thermogram that is substantially similar to the TGA thermogram of FIG. 24C.

26. A crystalline form of the compound of Formula 1:

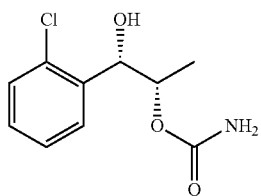

(1)

having an X-ray powder diffraction (XRPD) pattern comprising peaks at 8.6±0.2, 17.3±0.2, and 17.4±0.2 °2θ.

27. The crystalline form of embodiment 26, wherein the XRPD pattern further comprises peaks at 13.7±0.2 or 28.5±0.2 °2θ.

28. The crystalline form of embodiment 26 or 27, wherein the XRPD pattern further comprises peaks at 13.4±0.2 or 20.1±0.2 °2θ.

29. The crystalline form of any one of embodiments 26-28, wherein the XRPD pattern further comprises at least one peak at 6.9±0.2, 17.0±0.2, 19.6±0.2, 25.4±0.2, 26.1±0.2, 26.8±0.2, or 32.1±0.2 °2θ.

30. The crystalline form of any one of embodiments 26-29, wherein the crystalline form exhibits an XRPD pattern comprising the peaks listed in Table 9.

31. The crystalline form of any one of embodiments 26-30, wherein the crystalline form exhibits an XRPD pattern that is substantially similar to the XRPD pattern of FIG. 25A.

32. A crystalline form of the compound of Formula 1:

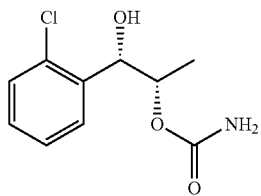

(1)

having an X-ray powder diffraction (XRPD) pattern comprising peaks at 14.7±0.2, 16.6±0.2, 22.1±0.2, 24.7±0.2, and 26.9±0.2 °2θ.

33. The crystalline form of embodiment 32, wherein the XRPD pattern further comprises peaks at 11.9±0.2 and 13.4±0.2 °2θ.

34. The crystalline form of any one of embodiments 32 or 33, wherein the XRPD pattern further comprises at least one peak at 12.6±0.2, 15.8±0.2, 18.5±0.2, 21.5±0.2, 22.6±0.2, 22.8±0.2, 24.5±0.2, 25.1±0.2, and 29.4±0.2, or 38.8±0.2 °2θ.

35. The crystalline form of any one of embodiments 32-34, wherein the crystalline form exhibits an XRPD pattern comprising the peaks listed in Table 15.

36. The crystalline form of any one of embodiments 32-35, wherein the crystalline form exhibits an XRPD pattern that is substantially similar to the XRPD pattern of FIG. 31A.

37. A crystalline form of the compound of Formula 1:

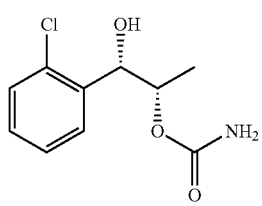

(1)

having an X-ray powder diffraction (XRPD) pattern comprising peaks at 10.0±0.2, 14.3±0.2, 16.3±0.2, 19.9±0.2 and 20.1±0.2 °2θ.

38. The crystalline form of embodiment 37, wherein the XRPD pattern further comprises peaks at 27.9±0.2 and 28.2±0.2 °2θ.

39. The crystalline form of any one of embodiments 37-38, wherein the XRPD pattern further comprises at least one peak at 6.6±0.2, 8.2±0.2, 8.4±0.2, 14.3±0.2, 21.4±0.2, or 25.9±0.2 °2θ.

40. The crystalline form of any one of embodiments 37-39, wherein the crystalline form exhibits an XRPD pattern comprising the peaks listed in Table 16.

41. The crystalline form of any one of embodiments 37-40, wherein the crystalline form exhibits an XRPD pattern that is substantially similar to the XRPD pattern of FIG. 32A.

42. The crystalline form of any one of embodiments 37-41, wherein the crystalline form exhibits a differential scanning calorimetry (DSC) thermogram comprising endothermic peaks with an onset at about 70° C. and about 89° C.

43. The crystalline form of any one of embodiments 37-42, wherein the crystalline form exhibits an about 3% (wt %) loss between about 73° C. to about 112° C. as determined by thermogravimetric analysis (TGA).

44. The crystalline form of any one of embodiments 37-43, wherein the crystalline form exhibits:
  a) a DSC thermogram that is substantially similar to the DSC thermogram of FIG. 32B; or
  b) a TGA thermogram that is substantially similar to the TGA thermogram of FIG. 32C.

45. A pharmaceutical composition comprising a crystalline form of any one of embodiments 1-44 and a pharmaceutically acceptable carrier.

46. A method for treating dyskinesia, muscle stiffness, convulsions, epilepsy, central nervous system disorders, Lou Gehrig's disease, multiple sclerosis, chronic pain, anxiety, seizures, autism, depression, bipolar disorder, senile dementia, Alzheimer's disease, or stroke in a subject in need thereof, comprising administering to the subject a therapeutically effective amount of a crystalline form of any one of embodiments 1-44.

47. A method for treating dyskinesia, muscle stiffness, convulsions, epilepsy, central nervous system disorders, Lou Gehrig's disease, multiple sclerosis, chronic pain, anxiety, seizures, autism, depression, bipolar disorder, senile dementia, Alzheimer's disease, or stroke in a subject in need thereof, comprising administering to the subject a therapeutically effective amount of a pharmaceutical composition of embodiment 44.

What is claimed:

1. A crystalline form of the compound of Formula 1:

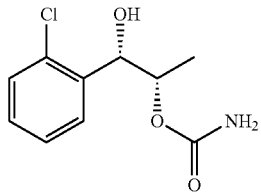

having an X-ray powder diffraction (XRPD) pattern comprising peaks at 10.9±0.2, 15.8±0.2, and 17.8±0.2 °2θ.

2. The crystalline form of claim 1, wherein the XRPD pattern further comprises peaks at 8.9±0.2 and 13.4±0.2 °2θ.

3. The crystalline form of claim 1, wherein the XRPD pattern further comprises peaks at 17.0±0.2 and 17.5±0.2 °2θ.

4. The crystalline form of claim 1, wherein the XRPD pattern further comprises at least one peak at 15.2±0.2, 19.8±0.2, 23.2±0.2, 24.0±0.2, 28.2±0.2, 30.4±0.2, or 30.8±0.2 °2θ.

5. The crystalline form of claim 1, wherein the crystalline form exhibits an XRPD pattern comprising the peaks listed in Table 8.

6. The crystalline form of claim 1, wherein the crystalline form exhibits an XRPD pattern that is substantially similar to the XRPD pattern of FIG. 24A.

7. The crystalline form of claim 1, wherein the crystalline form exhibits a differential scanning calorimetry (DSC) thermogram comprising an endothermic peak with an onset at about 82° C.

8. The crystalline form of claim 1, wherein the crystalline form exhibits:
 a) a DSC thermogram that is substantially similar to the DSC thermogram of FIG. 24B; or
 b) a TGA thermogram that is substantially similar to the TGA thermogram of FIG. 24C.

9. The crystalline form of claim 1, wherein the crystalline form has a chemical purity of greater than about 95% as determined by HPLC analysis.

10. A pharmaceutical composition comprising the crystalline form of claim 1 and a pharmaceutically acceptable carrier.

11. A method for treating dyskinesia, muscle stiffness, convulsions, epilepsy, central nervous system disorders, Lou Gehrig's disease, multiple sclerosis, chronic pain, anxiety, seizures, autism, depression, bipolar disorder, senile dementia, Alzheimer's disease, or stroke in a subject in need thereof, comprising administering to the subject a therapeutically effective amount of the crystalline form of claim 1.

12. A method for treating dyskinesia, muscle stiffness, convulsions, epilepsy, central nervous system disorders, Lou Gehrig's disease, multiple sclerosis, chronic pain, anxiety, seizures, autism, depression, bipolar disorder, senile dementia, Alzheimer's disease, or stroke in a subject in need thereof, comprising administering to the subject a therapeutically effective amount of the pharmaceutical composition of claim 10.

* * * * *